(12) United States Patent
Zipory et al.

(10) Patent No.: US 10,548,729 B2
(45) Date of Patent: Feb. 4, 2020

(54) DEPLOYMENT TECHNIQUES FOR ANNULOPLASTY RING AND OVER-WIRE ROTATION TOOL

(71) Applicant: VALTECH CARDIO, LTD., Or Yehuda (IL)

(72) Inventors: Yuval Zipory, Modi'in (IL); Oz Cabiri, Hod Hashsaron (IL); Yossi Gross, Moshav Mazor (IL); Tal Hammer, Ramat Gan (IL); Amir Gross, Moshav Mazor (IL); Francesco Maisano, Zürich (CH); Eran Miller, Moshav Beit Elazari (IL); Yoseph Weitzman, Tel Aviv (IL); Aram Ayvazian, Petah Tikva (IL)

(73) Assignee: Valtech Cardio, Ltd., Or Yehuda (IL)

(*) Notice: Subject to any disclaimer, the term of this patent is extended or adjusted under 35 U.S.C. 154(b) by 475 days.

(21) Appl. No.: 15/474,632

(22) Filed: Mar. 30, 2017

(65) Prior Publication Data
US 2017/0258588 A1    Sep. 14, 2017

Related U.S. Application Data

(63) Continuation of application No. 13/319,030, filed as application No. PCT/IL2010/000358 on May 4, 2010, (Continued)

(51) Int. Cl.
*A61F 2/24*    (2006.01)
*A61B 17/04*    (2006.01)
(Continued)

(52) U.S. Cl.
CPC ........ *A61F 2/2436* (2013.01); *A61B 17/0401* (2013.01); *A61B 17/064* (2013.01); (Continued)

(58) Field of Classification Search
CPC .... A61F 2/2409; A61F 2/2412; A61F 2/2442; A61F 2/2445; A61F 2/2448; A61F 2/2451; A61F 2/2454; A61F 2/2457
(Continued)

(56) References Cited

U.S. PATENT DOCUMENTS

| | | |
|---|---|---|
| 3,604,488 A | 9/1971 | Wishart |
| 3,656,185 A | 4/1972 | Carpentier |

(Continued)

FOREIGN PATENT DOCUMENTS

| | | |
|---|---|---|
| CA | 2671966 | 6/2008 |
| CN | 101653365 | 2/2010 |

(Continued)

OTHER PUBLICATIONS

O'Reilly S et al., "Heart valve surgery pushes the envelope," Medtech Insight 8(3):73, 99-108 (2006).
(Continued)

*Primary Examiner* — Martin T Ton
(74) *Attorney, Agent, or Firm* — Thomas C. Richardson

(57) ABSTRACT

An implant structure includes a contracting mechanism, including a rotatable structure for contracting the implant structure, and a locking mechanism. A rotation tool is configured to engage and rotate the rotatable structure. A longitudinal guide member is removably coupled to the contracting mechanism, configured to guide the rotation tool to the rotatable structure, and includes a distal force applicator. The rotation tool is axially moveable with respect to the guide member. The contracting mechanism is arranged such that the locking mechanism is (a) unlocked when the guide member is coupled to the contracting mechanism in a first state, thereby allowing the rotatable structure to rotate, and (b) locked when (i) the guide member is coupled to the contracting mechanism in a second state, thereby restricting (Continued)

the rotation of the rotatable structure, and (ii) the guide member is not coupled to the contracting mechanism, thereby restricting the rotation of the rotatable structure.

36 Claims, 34 Drawing Sheets

Related U.S. Application Data now Pat. No. 9,636,224, which is a continuation-in-part of application No. 12/435,291, filed on May 4, 2009, now Pat. No. 8,147,542, and a continuation-in-part of application No. 12/437,103, filed on May 7, 2009, now Pat. No. 8,715,342, and a continuation-in-part of application No. 12/548,991, filed on Aug. 27, 2009, now Pat. No. 8,808,368, and a continuation-in-part of application No. 12/689,635, filed on Jan. 19, 2010, now Pat. No. 8,545,553, and a continuation-in-part of application No. 12/689,693, filed on Jan. 19, 2010, now Pat. No. 8,911,494.

(51) Int. Cl.
*A61B 17/064* (2006.01)
*A61B 17/068* (2006.01)
*A61B 17/072* (2006.01)
*A61B 17/00* (2006.01)
*A61B 17/12* (2006.01)
*A61B 17/29* (2006.01)
*A61F 2/30* (2006.01)

(52) U.S. Cl.
CPC .......... *A61B 17/068* (2013.01); *A61B 17/072* (2013.01); *A61F 2/2445* (2013.01); *A61F 2/2451* (2013.01); *A61F 2/2457* (2013.01); *A61F 2/2466* (2013.01); *A61B 17/00234* (2013.01); *A61B 2017/00243* (2013.01); *A61B 2017/0409* (2013.01); *A61B 2017/0414* (2013.01); *A61B 2017/0441* (2013.01); *A61B 2017/0443* (2013.01); *A61B 2017/0464* (2013.01); *A61B 2017/0496* (2013.01); *A61B 2017/0647* (2013.01); *A61B 2017/0648* (2013.01); *A61B 2017/0649* (2013.01); *A61B 2017/12095* (2013.01); *A61B 2017/2923* (2013.01); *A61F 2/2409* (2013.01); *A61F 2/2412* (2013.01); *A61F 2002/30537* (2013.01); *A61F 2220/0016* (2013.01); *A61F 2250/0004* (2013.01)

(58) Field of Classification Search
USPC ...................................... 623/2.11, 2.36–2.41
See application file for complete search history.

(56) References Cited

U.S. PATENT DOCUMENTS

| | | | |
|---|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,961,738 A | 10/1990 | Mackin |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright |
| 5,258,008 A | 11/1993 | Wilk |
| 5,300,034 A | 4/1994 | Behnke |
| 5,306,296 A | 4/1994 | Wright et al. |
| 5,325,845 A | 7/1994 | Adair |
| 5,346,498 A | 9/1994 | Greelis et al. |
| 5,450,860 A | 9/1995 | O'Connor |
| 5,474,518 A | 12/1995 | Farrer-Velazquez |
| 5,477,856 A | 12/1995 | Lundquist |
| 5,593,424 A | 1/1997 | Northrup, III |
| 5,601,572 A | 2/1997 | Middleman |
| 5,626,609 A | 5/1997 | Zvenyatsky et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,810,882 A | 9/1998 | Bolduc |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell |
| 5,957,953 A | 9/1999 | DiPoto |
| 5,961,440 A | 10/1999 | Schweich et al. |
| 5,961,539 A | 10/1999 | Northrup, III et al. |
| 5,984,959 A | 11/1999 | Robertson |
| 6,042,554 A | 3/2000 | Rosenman |
| 6,045,497 A | 4/2000 | Schweich et al. |
| 6,050,936 A | 4/2000 | Schweich et al. |
| 6,059,715 A | 5/2000 | Schweich et al. |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern |
| 6,110,200 A | 8/2000 | Hinnenkamp |
| 6,143,024 A | 11/2000 | Campbell |
| 6,159,240 A | 12/2000 | Sparer |
| 6,165,119 A | 12/2000 | Schweich et al. |
| 6,174,332 B1 | 1/2001 | Loch |
| 6,183,411 B1 | 2/2001 | Mortier |
| 6,187,040 B1 | 2/2001 | Wright |
| 6,217,610 B1 | 4/2001 | Carpentier |
| 6,231,602 B1 | 5/2001 | Carpentier |
| 6,251,092 B1 | 6/2001 | Qin et al. |
| 6,296,656 B1 | 10/2001 | Bodluc et al. |
| 6,315,784 B1 | 11/2001 | Djurovic |
| 6,319,281 B1 | 11/2001 | Patel |
| 6,332,893 B1 | 12/2001 | Mortier et al. |
| 6,355,030 B1 | 3/2002 | Aldrich et al. |
| 6,368,348 B1 | 4/2002 | Gabbay |
| 6,402,780 B2 | 6/2002 | Williamson, IV |
| 6,406,420 B1 | 6/2002 | McCarthy et al. |
| 6,406,493 B1 | 6/2002 | Tu |
| 6,419,696 B1 | 7/2002 | Ortiz et al. |
| 6,451,054 B1 | 9/2002 | Stevens |
| 6,461,366 B1 | 10/2002 | Seguin |
| 6,470,892 B1 | 10/2002 | Forsell |
| 6,503,274 B1 | 1/2003 | Howanec |
| 6,524,338 B1 | 2/2003 | Gundry |
| 6,533,772 B1 | 3/2003 | Sherts et al. |
| 6,537,314 B2 | 3/2003 | Langberg et al. |
| 6,547,801 B1 | 4/2003 | Dargent |
| 6,554,845 B1 | 4/2003 | Fleenor |
| 6,564,805 B2 | 5/2003 | Garrison et al. |
| 6,565,603 B2 | 5/2003 | Cox |

(56) References Cited

U.S. PATENT DOCUMENTS

| | | |
|---|---|---|
| 6,569,198 B1 | 5/2003 | Wilson et al. |
| 6,579,297 B2 | 6/2003 | Bicek et al. |
| 6,589,160 B2 | 7/2003 | Schweich et al. |
| 6,602,288 B1 | 8/2003 | Cosgrove |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,652,556 B1 | 11/2003 | VanTasel |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg |
| 6,709,385 B2 | 3/2004 | Forsell |
| 6,709,456 B2 | 3/2004 | Langberg et al. |
| 6,711,444 B2 | 3/2004 | Koblish |
| 6,718,985 B2 | 4/2004 | Hlavka et al. |
| 6,719,786 B2 | 4/2004 | Ryan |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon |
| 6,790,231 B2 | 9/2004 | Liddicoat |
| 6,797,001 B2 | 9/2004 | Mathis |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz |
| 6,964,686 B2 | 11/2005 | Gordon |
| 6,976,995 B2 | 12/2005 | Mathis |
| 6,986,775 B2 | 1/2006 | Morales et al. |
| 6,989,028 B2 | 1/2006 | Lashinski et al. |
| 6,997,951 B2 | 2/2006 | Solem |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,850 B2 | 7/2006 | Kortenbach |
| 7,077,862 B2 | 7/2006 | Vidlund |
| 7,087,064 B1 | 8/2006 | Hyde |
| 7,101,395 B2 | 9/2006 | Tremulis |
| 7,101,396 B2 | 9/2006 | Artof et al. |
| 7,112,207 B2 | 9/2006 | Allen et al. |
| 7,118,595 B2 | 10/2006 | Ryan |
| 7,125,421 B2 | 10/2006 | Tremulis et al. |
| 7,150,737 B2 | 12/2006 | Purdy et al. |
| 7,159,593 B2 | 1/2007 | McCarthy |
| 7,166,127 B2 | 1/2007 | Spence |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat |
| 7,189,199 B2 | 3/2007 | McCarthy et al. |
| 7,192,443 B2 | 3/2007 | Solem |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shoulian |
| 7,364,588 B2 | 4/2008 | Mathis |
| 7,377,941 B2 | 5/2008 | Rhee |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb |
| 7,527,647 B2 | 5/2009 | Spence |
| 7,530,995 B2 | 5/2009 | Quijano |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn |
| 7,588,582 B2 | 9/2009 | Starksen et al. |
| 7,591,826 B2 | 9/2009 | Alferness |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton |
| 7,682,319 B2 | 3/2010 | Martin |
| 7,682,369 B2 | 3/2010 | Seguin |
| 7,686,822 B2 | 3/2010 | Shayani |
| 7,699,892 B2 | 4/2010 | Rafiee |
| 7,704,269 B2 | 4/2010 | Goar |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,927,370 B2 | 4/2011 | Webler et al. |
| 7,927,371 B2 | 4/2011 | Navia |
| 7,942,927 B2 | 5/2011 | Kaye et al. |
| 7,947,056 B2 | 5/2011 | Griego et al. |
| 7,955,377 B2 | 6/2011 | Melsheimer |
| 7,988,725 B2 | 8/2011 | Gross |

(56) References Cited

U.S. PATENT DOCUMENTS

| | | |
|---|---|---|
| 7,992,567 B2 | 8/2011 | Hirotsuka |
| 7,993,368 B2 | 8/2011 | Gambale et al. |
| 7,993,397 B2 | 8/2011 | Lashinski |
| 8,012,201 B2 | 9/2011 | Lashinski et al. |
| 8,034,103 B2 | 10/2011 | Burriesci |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde |
| 8,070,805 B2 | 12/2011 | Vidlund |
| 8,075,616 B2 | 12/2011 | Solem |
| 8,100,964 B2 | 1/2012 | Spence |
| 8,123,800 B2 | 2/2012 | McCarthy |
| 8,123,801 B2 | 2/2012 | Milo |
| 8,142,493 B2 | 3/2012 | Spence et al. |
| 8,142,495 B2 | 3/2012 | Hasenkam |
| 8,142,496 B2 | 3/2012 | Berreklouw |
| 8,147,542 B2 | 4/2012 | Maisano et al. |
| 8,152,844 B2 | 4/2012 | Rao |
| 8,163,013 B2 | 4/2012 | Machold |
| 8,187,299 B2 | 5/2012 | Goldfarb et al. |
| 8,187,324 B2 | 5/2012 | Webler |
| 8,202,315 B2 | 6/2012 | Hlavka |
| 8,206,439 B2 | 6/2012 | Gomez-Duran |
| 8,216,302 B2 | 7/2012 | Wilson et al. |
| 8,226,711 B2 | 7/2012 | Mortier |
| 8,231,671 B2 | 7/2012 | Kim |
| 8,241,351 B2 * | 8/2012 | Cabiri ............... A61F 2/2445 623/2.37 |
| 8,252,050 B2 | 8/2012 | Maisano et al. |
| 8,262,725 B2 | 9/2012 | Subramanian |
| 8,277,502 B2 | 10/2012 | Miller |
| 8,287,584 B2 | 10/2012 | Salahieh |
| 8,287,591 B2 | 10/2012 | Keidar |
| 8,303,608 B2 | 11/2012 | Goldfarb et al. |
| 8,323,334 B2 | 12/2012 | Deem |
| 8,328,868 B2 | 12/2012 | Paul |
| 8,333,777 B2 | 12/2012 | Schaller |
| 8,343,173 B2 | 1/2013 | Starksen et al. |
| 8,343,174 B2 | 1/2013 | Goldfarb |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,430,926 B2 | 4/2013 | Kirson |
| 8,449,599 B2 | 5/2013 | Chau et al. |
| 8,454,686 B2 | 6/2013 | Alkhatib |
| 8,460,370 B2 | 6/2013 | Zakay et al. |
| 8,460,371 B2 | 6/2013 | Hlavka et al. |
| 8,475,491 B2 | 7/2013 | Milo |
| 8,480,732 B2 | 7/2013 | Subramanian |
| 8,500,800 B2 | 8/2013 | Maisano et al. |
| 8,518,107 B2 | 8/2013 | Tsukashima et al. |
| 8,523,881 B2 | 9/2013 | Cabiri |
| 8,523,940 B2 | 9/2013 | Richardson |
| 8,545,553 B2 | 10/2013 | Zipory |
| 8,551,161 B2 | 10/2013 | Dolan |
| 8,585,755 B2 | 11/2013 | Chau et al. |
| 8,591,576 B2 | 11/2013 | Hasenkam |
| 8,608,797 B2 | 12/2013 | Gross |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,808,371 B2 | 8/2014 | Cartledge |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,226,825 B2 | 1/2016 | Starksen et al. |
| 9,241,702 B2 | 1/2016 | Maisano et al. |
| 9,265,608 B2 | 2/2016 | Miller et al. |
| 9,326,857 B2 | 5/2016 | Cartledge et al. |
| 9,351,830 B2 | 5/2016 | Gross et al. |
| 9,414,921 B2 | 8/2016 | Miller et al. |
| 9,427,316 B2 | 8/2016 | Schweich et al. |
| 9,474,606 B2 | 10/2016 | Zipory et al. |
| 9,526,613 B2 | 12/2016 | Gross et al. |
| 9,561,104 B2 | 2/2017 | Miller et al. |
| 2001/0021874 A1 | 9/2001 | Carpentier |
| 2001/0044656 A1 | 11/2001 | Williamson |
| 2002/0022862 A1 | 2/2002 | Grafton et al. |
| 2002/0029080 A1 | 3/2002 | Mortier |
| 2002/0042621 A1 | 4/2002 | Liddicoat |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0133180 A1 | 9/2002 | Ryan et al. |
| 2002/0151916 A1 | 10/2002 | Muramatsu |
| 2002/0151961 A1 | 10/2002 | Lashinski |
| 2002/0151970 A1 | 10/2002 | Garrison |
| 2002/0169358 A1 | 11/2002 | Mortier et al. |
| 2002/0173841 A1 | 11/2002 | Ortiz et al. |
| 2002/0177904 A1 | 11/2002 | Huxel et al. |
| 2002/0188301 A1 | 12/2002 | Dallara et al. |

(56) References Cited

U.S. PATENT DOCUMENTS

| | | |
|---|---|---|
| 2002/0198586 A1 | 12/2002 | Inoue |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely |
| 2003/0083742 A1 | 5/2003 | Spence |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidiund |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane |
| 2003/0229350 A1 | 12/2003 | Kay |
| 2003/0229395 A1 | 12/2003 | Cox |
| 2003/0233142 A1 | 12/2003 | Morales et al. |
| 2004/0010287 A1 | 1/2004 | Bonutti |
| 2004/0019359 A1 | 1/2004 | Worley et al. |
| 2004/0019377 A1 | 1/2004 | Taylor |
| 2004/0024451 A1 | 2/2004 | Johnson et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0122448 A1 | 6/2004 | Levine |
| 2004/0122514 A1 | 6/2004 | Forgarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133274 A1 | 7/2004 | Webler |
| 2004/0133374 A1 | 7/2004 | Kattan |
| 2004/0133744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka |
| 2004/0176788 A1 | 9/2004 | Opolski |
| 2004/0181287 A1 | 9/2004 | Gellman |
| 2004/0186566 A1 | 9/2004 | Hindrichs |
| 2004/0193191 A1 | 9/2004 | Starksen et al. |
| 2004/0236419 A1 | 11/2004 | Milo |
| 2004/0243227 A1 | 12/2004 | Starsken et al. |
| 2004/0249453 A1 | 12/2004 | Cartledge |
| 2004/0260317 A1 | 12/2004 | Bloom et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0055038 A1 | 3/2005 | Kelleher et al. |
| 2005/0055087 A1 | 3/2005 | Statksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107812 A1 | 5/2005 | Starksen et al. |
| 2005/0107871 A1 | 5/2005 | Realyvasquez et al. |
| 2005/0119734 A1 | 6/2005 | Spence |
| 2005/0125002 A1 | 6/2005 | Baran et al. |
| 2005/0125011 A1 | 6/2005 | Spence et al. |
| 2005/0131533 A1 | 6/2005 | Alfieri |
| 2005/0137686 A1 | 6/2005 | Salahieh et al. |
| 2005/0137688 A1 | 6/2005 | Salahieh et al. |
| 2005/0137695 A1 | 6/2005 | Salahieh |
| 2005/0159728 A1 | 7/2005 | Armour et al. |
| 2005/0171601 A1 | 8/2005 | Cosgrove et al. |
| 2005/0177180 A1 | 8/2005 | Kaganov |
| 2005/0177228 A1 | 8/2005 | Solem et al. |
| 2005/0187613 A1 | 8/2005 | Bolduc et al. |
| 2005/0192596 A1 | 9/2005 | Jugenheimer et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288776 A1 | 12/2005 | Shaoulian et al. |
| 2005/0288778 A1 | 12/2005 | Shaoulian |
| 2005/0288781 A1 | 12/2005 | Moaddeb et al. |
| 2006/0004442 A1 | 1/2006 | Spenser et al. |
| 2006/0004443 A1 | 1/2006 | Liddicoat |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat |
| 2006/0085012 A1 | 4/2006 | Dolan |
| 2006/0095009 A1 | 5/2006 | Lampropoulos |
| 2006/0106423 A1 | 5/2006 | Weisel |
| 2006/0116757 A1 | 6/2006 | Lashinski et al. |
| 2006/0122633 A1 | 6/2006 | To |
| 2006/0129166 A1 | 6/2006 | Lavelle |
| 2006/0149280 A1 | 7/2006 | Harvine et al. |
| 2006/0149368 A1 | 7/2006 | Spence |
| 2006/0161265 A1 | 7/2006 | Levine et al. |
| 2006/0184240 A1 | 8/2006 | Jiminez |
| 2006/0184242 A1 | 8/2006 | Lichtenstein |
| 2006/0195134 A1 | 8/2006 | Crittenden |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia |
| 2006/0271175 A1 | 11/2006 | Woolfson |
| 2006/0282161 A1 | 12/2006 | Huyn et al. |
| 2006/0287661 A1 | 12/2006 | Bolduc |
| 2006/0287716 A1 | 12/2006 | Banbury et al. |
| 2007/0001627 A1 | 1/2007 | Lin et al. |
| 2007/0016287 A1 | 1/2007 | Cartledge et al. |
| 2007/0016288 A1 | 1/2007 | Gurskis |
| 2007/0021781 A1 | 1/2007 | Jervis |
| 2007/0027533 A1 | 2/2007 | Douk |
| 2007/0027536 A1 | 2/2007 | Mihaljevic et al. |
| 2007/0038221 A1 | 2/2007 | Fine |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |

(56) References Cited

U.S. PATENT DOCUMENTS

| | | |
|---|---|---|
| 2007/0118213 A1 | 5/2007 | Loulmet |
| 2007/0118215 A1 | 5/2007 | Moaddeb |
| 2007/0142907 A1 | 6/2007 | Moaddeb |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0233239 A1 | 10/2007 | Navia et al. |
| 2007/0239208 A1 | 10/2007 | Crawford |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge |
| 2008/0027555 A1 | 1/2008 | Hawkins |
| 2008/0035160 A1 | 2/2008 | Woodson et al. |
| 2008/0039935 A1 | 2/2008 | Buch |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak |
| 2008/0071366 A1 | 3/2008 | Tuval |
| 2008/0086138 A1 | 4/2008 | Stone et al. |
| 2008/0086203 A1 | 4/2008 | Roberts |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0125861 A1 | 5/2008 | Webler et al. |
| 2008/0140116 A1 | 6/2008 | Bonutti |
| 2008/0167714 A1 | 7/2008 | St. Goar |
| 2008/0177382 A1 | 7/2008 | Hyde et al. |
| 2008/0195126 A1 | 8/2008 | Solem |
| 2008/0195200 A1 | 8/2008 | Vidlund |
| 2008/0208265 A1 | 8/2008 | Frazier et al. |
| 2008/0221672 A1 | 9/2008 | Lamphere |
| 2008/0243245 A1 | 10/2008 | Thambar |
| 2008/0262480 A1 | 10/2008 | Stahler et al. |
| 2008/0262609 A1 | 10/2008 | Gross et al. |
| 2008/0275300 A1 | 11/2008 | Rothe |
| 2008/0275469 A1 | 11/2008 | Fanton |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043153 A1 | 2/2009 | Zollinger et al. |
| 2009/0043381 A1 | 2/2009 | Macoviak |
| 2009/0054969 A1 | 2/2009 | Salahieh |
| 2009/0062866 A1 | 3/2009 | Jackson |
| 2009/0076586 A1 | 3/2009 | Hauser |
| 2009/0076600 A1 | 3/2009 | Quinn |
| 2009/0088837 A1 | 4/2009 | Gillinov |
| 2009/0093877 A1 | 4/2009 | Keidar et al. |
| 2009/0099650 A1 | 4/2009 | Bolduc |
| 2009/0105816 A1 | 4/2009 | Olsen et al. |
| 2009/0125102 A1 | 5/2009 | Cartledge |
| 2009/0149872 A1 | 6/2009 | Gross et al. |
| 2009/0171439 A1 | 7/2009 | Nissl |
| 2009/0177266 A1 | 7/2009 | Powell et al. |
| 2009/0177274 A1 | 7/2009 | Scorsin |
| 2009/0177277 A1 | 7/2009 | Milo |
| 2009/0222083 A1 | 9/2009 | Nguyen et al. |
| 2009/0248148 A1 | 10/2009 | Shaolian |
| 2009/0254103 A1 | 10/2009 | Deustch |
| 2009/0259307 A1 | 10/2009 | Gross et al. |
| 2009/0264994 A1 | 10/2009 | Saadat |
| 2009/0264995 A1 | 10/2009 | Subramanian |
| 2009/0287231 A1 | 11/2009 | Brooks et al. |
| 2009/0287304 A1 | 11/2009 | Dahlgren |
| 2009/0299409 A1 | 12/2009 | Coe |
| 2009/0326648 A1 | 12/2009 | Machold et al. |
| 2010/0001038 A1 | 1/2010 | Levin |
| 2010/0010538 A1 | 1/2010 | Juravic |
| 2010/0023117 A1 | 1/2010 | Yoganathan |
| 2010/0023118 A1 | 1/2010 | Medlock et al. |
| 2010/0030014 A1 | 2/2010 | Ferrazzi |
| 2010/0030328 A1 | 2/2010 | Seguin |
| 2010/0042147 A1 | 2/2010 | Janovsky et al. |
| 2010/0049313 A1 | 2/2010 | Alon et al. |
| 2010/0063542 A1 | 3/2010 | Van der Burg |
| 2010/0063550 A1 | 3/2010 | Felix |
| 2010/0063586 A1 | 3/2010 | Hasenkam |
| 2010/0076499 A1 | 3/2010 | McNamara et al. |
| 2010/0094248 A1 | 4/2010 | Nguyen et al. |
| 2010/0114180 A1 | 5/2010 | Rock |
| 2010/0121349 A1 | 5/2010 | Meier |
| 2010/0121435 A1 | 5/2010 | Subratnanian et al. |
| 2010/0121437 A1 | 5/2010 | Subratnanian et al. |
| 2010/0130992 A1 | 5/2010 | Machold et al. |
| 2010/0152845 A1 | 6/2010 | Bloom |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0179574 A1 | 7/2010 | Longoria |
| 2010/0198347 A1 | 8/2010 | Zakay et al. |
| 2010/0211166 A1 | 8/2010 | Miller et al. |
| 2010/0217184 A1 | 8/2010 | Koblish et al. |
| 2010/0217382 A1 | 8/2010 | Chau |
| 2010/0234935 A1 | 9/2010 | Bashiri et al. |
| 2010/0249915 A1 | 9/2010 | Zhang |
| 2010/0249920 A1 | 9/2010 | Bolling |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory |
| 2010/0280605 A1 | 11/2010 | Hammer |
| 2010/0286628 A1 | 11/2010 | Gross |
| 2010/0286767 A1 | 11/2010 | Zipory |
| 2010/0305475 A1 | 12/2010 | Hinchliffe et al. |
| 2010/0324598 A1 | 12/2010 | Anderson |
| 2011/0004210 A1 | 1/2011 | Johnson |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Otsuro et al. |
| 2011/0029066 A1 | 2/2011 | Gilad |
| 2011/0035000 A1 | 2/2011 | Nieminen et al. |
| 2011/0066231 A1 | 3/2011 | Cartledge |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller |
| 2011/0118832 A1 | 5/2011 | Punjabi |
| 2011/0137410 A1 | 6/2011 | Hacohen |
| 2011/0144703 A1 | 6/2011 | Krause |
| 2011/0166649 A1 | 7/2011 | Gross |
| 2011/0184510 A1 | 7/2011 | Maisano et al. |
| 2011/0190879 A1 | 8/2011 | Bobo et al. |
| 2011/0202130 A1 | 8/2011 | Cartledge |
| 2011/0208283 A1 | 8/2011 | Rust |
| 2011/0224785 A1 | 9/2011 | Hacohen |
| 2011/0230941 A1 | 9/2011 | Markus |
| 2011/0230961 A1 | 9/2011 | Langer |
| 2011/0238088 A1 | 9/2011 | Bolduc et al. |
| 2011/0257433 A1 | 10/2011 | Walker |
| 2011/0257633 A1 | 10/2011 | Cartledge |

(56) References Cited

U.S. PATENT DOCUMENTS

| | | |
|---|---|---|
| 2011/0257728 A1 | 10/2011 | Kuehn |
| 2011/0264208 A1 | 10/2011 | Duffy |
| 2011/0276062 A1 | 11/2011 | Bolduc |
| 2011/0282361 A1 | 11/2011 | Miller et al. |
| 2011/0288435 A1 | 11/2011 | Christy et al. |
| 2011/0288635 A1 | 11/2011 | Miller |
| 2011/0301498 A1 | 12/2011 | Maenhout et al. |
| 2011/0301698 A1 | 12/2011 | Miller et al. |
| 2012/0022557 A1 | 1/2012 | Cabiri |
| 2012/0022639 A1 | 1/2012 | Hacohen et al. |
| 2012/0022640 A1 | 1/2012 | Gross et al. |
| 2012/0022644 A1 | 1/2012 | Reich |
| 2012/0035712 A1 | 2/2012 | Maisano et al. |
| 2012/0078355 A1 | 3/2012 | Zipory |
| 2012/0078359 A1 | 3/2012 | Li et al. |
| 2012/0089022 A1 | 4/2012 | House et al. |
| 2012/0095552 A1 | 4/2012 | Spence |
| 2012/0109155 A1 | 5/2012 | Robinson et al. |
| 2012/0123531 A1 | 5/2012 | Tsukashima et al. |
| 2012/0136436 A1 | 5/2012 | Cabiri |
| 2012/0143323 A1 | 6/2012 | Hasenkam |
| 2012/0150290 A1 | 6/2012 | Gabbay |
| 2012/0158021 A1 | 6/2012 | Morrill |
| 2012/0179086 A1 | 7/2012 | Shank |
| 2012/0191182 A1 | 7/2012 | Hauser et al. |
| 2012/0197388 A1 | 8/2012 | Khairkhahan et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller |
| 2012/0296349 A1 | 11/2012 | Smith et al. |
| 2012/0296417 A1 | 11/2012 | Hill et al. |
| 2012/0296419 A1 | 11/2012 | Richardson |
| 2012/0310330 A1 | 12/2012 | Buchbinder et al. |
| 2012/0323313 A1 | 12/2012 | Seguin |
| 2012/0330410 A1 | 12/2012 | Hammer |
| 2012/0330411 A1 | 12/2012 | Gross |
| 2013/0023758 A1 | 1/2013 | Fabro |
| 2013/0030522 A1 | 1/2013 | Rowe et al. |
| 2013/0035759 A1 | 2/2013 | Gross et al. |
| 2013/0046373 A1 | 2/2013 | Cartledge et al. |
| 2013/0079873 A1 | 3/2013 | Migliazza |
| 2013/0297013 A1 | 3/2013 | Klima et al. |
| 2013/0085529 A1 | 4/2013 | Housman |
| 2013/0090724 A1 | 4/2013 | Subramanian |
| 2013/0096672 A1 | 4/2013 | Reich |
| 2013/0096673 A1 | 4/2013 | Hill |
| 2013/0116776 A1 | 5/2013 | Gross et al. |
| 2013/0116780 A1 | 5/2013 | Miller |
| 2013/0123910 A1 | 5/2013 | Cartledge |
| 2013/0131791 A1 | 5/2013 | Hlavka et al. |
| 2013/0131792 A1 | 5/2013 | Miller |
| 2013/0166017 A1 | 6/2013 | Cartledge et al. |
| 2013/0172992 A1 | 7/2013 | Gross et al. |
| 2013/0190863 A1 | 7/2013 | Call et al. |
| 2013/0190866 A1 | 7/2013 | Zipory |
| 2013/0197632 A1 | 8/2013 | Kovach |
| 2013/0204361 A1 | 8/2013 | Adams |
| 2013/0226289 A1 | 8/2013 | Shaolian |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0304093 A1 | 11/2013 | Serina et al. |
| 2013/0325118 A1 | 12/2013 | Cartledge |
| 2014/0018914 A1 | 1/2014 | Zipory et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0148898 A1 | 5/2014 | Gross et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0222137 A1 | 8/2014 | Miller et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0257475 A1 | 9/2014 | Gross et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon |
| 2014/0324164 A1 | 10/2014 | Gross et al. |
| 2014/0343668 A1 | 11/2014 | Zipory et al. |
| 2014/0379006 A1 | 12/2014 | Sutherland et al. |
| 2015/0012087 A1 | 1/2015 | Miller et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0105855 A1 | 4/2015 | Cabiri et al. |
| 2015/0112432 A1 | 4/2015 | Reich et al. |
| 2015/0127097 A1 | 5/2015 | Neumann et al. |
| 2015/0182336 A1 | 7/2015 | Zipory et al. |
| 2015/0230924 A1 | 8/2015 | Miller |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0297212 A1 | 10/2015 | Reich et al. |
| 2015/0351906 A1 | 12/2015 | Hammer et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0324633 A1 | 11/2016 | Gross et al. |
| 2016/0361168 A1 | 12/2016 | Gross et al. |
| 2016/0361169 A1 | 12/2016 | Gross et al. |
| 2017/0000609 A1 | 1/2017 | Gross et al. |

FOREIGN PATENT DOCUMENTS

| | | |
|---|---|---|
| EP | 0611561 | 8/1994 |
| EP | 06/14342 | 9/1994 |
| EP | 10/06905 | 6/2000 |
| EP | 0954257 | 8/2000 |
| EP | 1258437 | 11/2002 |
| EP | 0871417 | 10/2003 |
| EP | 1266641 | 10/2004 |
| EP | 1034753 | 2/2005 |
| EP | 1258232 | 1/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 1861045 | 3/2015 |
| EP | 1465555 | 5/2015 |
| IL | 223448 | 12/2012 |
| WO | 92/05093 | 4/1992 |
| WO | 1993/015690 | 8/1993 |
| WO | 96/39963 | 12/1996 |
| WO | 96/40344 | 12/1996 |
| WO | 97/01369 | 1/1997 |
| WO | 98/46149 | 10/1998 |
| WO | 1999/030647 | 6/1999 |

(56) References Cited

FOREIGN PATENT DOCUMENTS

| | | |
|---|---|---|
| WO | 99/033414 | 7/1999 |
| WO | 99/063907 | 12/1999 |
| WO | 99/063910 | 12/1999 |
| WO | 2000/009048 | 2/2000 |
| WO | 00/22981 | 4/2000 |
| WO | 01/26586 | 4/2001 |
| WO | 01/56457 | 8/2001 |
| WO | 2001/087191 | 11/2001 |
| WO | 02/085250 | 10/2002 |
| WO | 02/085251 | 10/2002 |
| WO | 02/085252 | 10/2002 |
| WO | 03/028558 | 4/2003 |
| WO | 03/047467 | 6/2003 |
| WO | 2003/049647 | 6/2003 |
| WO | 2003/105667 | 12/2003 |
| WO | 2004/012583 | 2/2004 |
| WO | 2004/019816 | 3/2004 |
| WO | 2004/019826 | 3/2004 |
| WO | 04/103434 | 12/2004 |
| WO | 05/021063 | 3/2005 |
| WO | 05/046488 | 5/2005 |
| WO | 2005/062931 | 7/2005 |
| WO | 06/012013 | 2/2006 |
| WO | 06/012038 | 2/2006 |
| WO | 06/086434 | 8/2006 |
| WO | 06/097931 | 9/2006 |
| WO | 06/105084 | 10/2006 |
| WO | 06/116558 | 11/2006 |
| WO | 07/011799 | 1/2007 |
| WO | 2007/080595 | 7/2007 |
| WO | 07/121314 | 10/2007 |
| WO | 07/136783 | 11/2007 |
| WO | 07/136981 | 11/2007 |
| WO | 2008/014144 | 1/2008 |
| WO | 2008/031103 | 3/2008 |
| WO | 08/068756 | 6/2008 |
| WO | 2009/160631 | 10/2009 |
| WO | 10/004546 | 1/2010 |
| WO | 2010/000454 | 1/2010 |
| WO | 2010/006905 | 1/2010 |
| WO | 2010/044851 | 4/2010 |
| WO | 2010/065274 | 6/2010 |
| WO | 10/073246 | 7/2010 |
| WO | 2010/085649 | 7/2010 |
| WO | 2010/128502 | 11/2010 |
| WO | 2010/128503 | 11/2010 |
| WO | 2010/150178 | 12/2010 |
| WO | 2011/051942 | 5/2011 |
| WO | 11/067770 | 6/2011 |
| WO | 2011/089401 | 7/2011 |
| WO | 2011/089601 | 7/2011 |
| WO | 2011/111047 | 9/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 93/10714 | 3/2012 |
| WO | 2012/068541 | 5/2012 |
| WO | 2012/106346 | 8/2012 |
| WO | 2012/176195 | 12/2012 |
| WO | 2013/021374 | 2/2013 |
| WO | 2013/021375 | 2/2013 |
| WO | 2013/069019 | 5/2013 |
| WO | 2013/078497 | 6/2013 |
| WO | 2013/088327 | 6/2013 |
| WO | 2014/064694 | 5/2014 |
| WO | 2014/064695 | 5/2014 |
| WO | 2014/064964 | 5/2014 |
| WO | 2014/076696 | 5/2014 |
| WO | 2014/087402 | 6/2014 |
| WO | 2014/108903 | 7/2014 |
| WO | 2014/115149 | 7/2014 |
| WO | 2014/195786 | 12/2014 |
| WO | 2015/059699 | 4/2015 |
| WO | 2015/193728 | 12/2015 |
| WO | 2016/059639 | 4/2016 |
| WO | 2016/087934 | 6/2016 |
| WO | 2016/174669 | 11/2016 |

OTHER PUBLICATIONS

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Swain CP et al., "An endoscopically deliverable tissue-transfixing device for securing biosensors in the gastrointestinal tract," Gastrointestinal Endoscopy 40(6): 730-734 (1994).

Odell JA et al., "Early Results o4yf a Simplified Method of Mitral Valve Annuloplasty," Circulation 92:150-154 (1995).

U.S. Appl. No. 60/873,075, filed Dec. 5, 2006.

An International Preliminary Report on Patentability dated Nov. 9, 2011, which issued during the prosecution of Applicant's PCT/IL2010/000357.

U.S. Appl. No. 60/902,146, filed Feb. 16, 2007.

An International Preliminary Report on Patentability dated Jun. 5, 2012, which issued during the prosecution of Applicant's PCT/IL2010/001024.

U.S. Appl. No. 61/001,013, filed Oct. 9, 2007.

An International Preliminary Report on Patentability dated Nov. 27, 2012 which issued during the prosecution of Applicant's PCT/IL2011/000404.

U.S. Appl. No. 61/132,295, filed Jun. 16, 2008.

Notice of Allowance dated Apr. 27, 2012, which issued during the prosecution of U.S. Appl. No. 12/341,960.

"Two dimensional real-time ultrasonic imaging of the heart and great vessels", Mayo Clin Proc. vol. 53:271-303, 1978.

An Office Action dated Mar. 29, 2011, which issued during the prosecution of U.S. Appl. No. 12/341,960.

An Office Action dated Aug. 2, 2011, which issued during the prosecution of U.S. Appl. No. 12/435,291.

A Restriction Requirement dated Mar. 30, 2012, which issued during the prosecution of U.S. Appl. No. 12/785,717.

An International Search Report and a Written Opinion both dated Jun. 10, 2010, which issued during the prosecution of Applicant's PCT/IL09/01209.

An Office Action dated Jan. 27, 2012 which issued during the prosecution of U.S. Appl. No. 12/548,991.

An Office Action dated Apr. 6, 2010, which issued during the prosecution of Applicant's U.S. Appl. No. 12/484,512.

An Office Action dated Nov. 5, 2012, which issued during, the prosecution of U.S. Appl. No. 12/795,026.

Notice of Allowance dated Feb. 19, 2014, which issued during the prosecution of U.S. Appl. No. 12/795,192.

An International Search Report and a Written Opinion both dated Aug. 17, 2010, which issued during the prosecution of Applicant's PCT/IL10/00357.

An Office Action dated Sep. 16, 2009 which issued during the prosecution of U.S. Appl. No. 11/950,930.

Alfieri et al., "An effective technique to correct anterior mitral leaflet prolapse," J Card 14(6):468-470 (1999).

A Restriction Requirement dated Nov. 19, 2012, which issued during the prosecution of U.S. Appl. No. 12/926,673.

Alfieri et al., "The double orifice technique in mitral valve repair: a simple solution for complex problems," Journal of Thoracic Cardiovascular Surgery 122:674-681 (2001).

A Supplementary European Search Report dated Jan. 20, 2015, which issued during the prosecution of European Patent Application No. 12803037.6.

An International Preliminary Report on Patentability dated Jun. 29, 2011, which issued during the prosecution of Applicant's PCT/IL2009/001209.

Alfieri, "The edge-to-edge repair of the mitral valve," [Abstract] 6th Annual NewEra Cardiac Care: Innovation & Technology, Heart Surgery Forum pp. 103. (2000).

Dang NC et al. "Simplified Placement of Multiple Artificial Mitral Valve Chords," The Heart Surgery Forum #2005-1005, 8 (3) (2005).

(56) References Cited

OTHER PUBLICATIONS

An International Search Report and a Written Opinion both dated Feb. 10, 2011, which issued during the prosecution of Applicant's PCT/IL10/00890.
Alfieri et al."Novel Suture Device for Beating-Heart Mitral Leaflet Approximation", Ann Thorac Surg. 2002, 74:1488-1493.
A Notice of Allowance dated Jun. 26, 2012, which issued during the prosecution of U.S. Appl. No. 12/608,316.
An International Search Report and a Written Opinion both dated Sep. 12, 2008, which issued during the prosecution of Applicant's PCT/IL07/01503.
An Office Action dated Jan. 23, 2012, which issued during the prosecution of U.S. Appl. No. 12/692,061.
An International Search Report dated May 19, 2011, which issued during the prosecution of Applicant's PCT/IL2011/00064.
A Supplementary European Search Report dated Feb. 1, 2011, which issued during the prosecution of European Patent Application No. EP 07849540.
An International Search Report together with Written Opinion both dated Mar. 30, 2011, which issued during the prosecution of Applicant's PCT/IL2010/001024.
An Office Action dated Aug. 6, 2012, which issued during the prosecution of U.S. Appl. No. 12/548,991.
An Office Action dated Jul. 20, 2012, which issued during the prosecution of U.S. Appl. No. 12/843,412.
Notice of Allowance dated Mar. 25, 2015, which issued during the prosecution of U.S. Appl. No. 13/749,153.
An Office Action dated Aug. 24, 2012, which issued during the prosecution of U.S. Appl. No. 12/563,930.
An Office Action dated May 10, 2012, which issued during the prosecution of U.S. Appl. No. 12/795,026.
An Office Action dated Mar. 9, 2012, which issued during the prosecution of U.S. Appl. No. 12/689,635.
A Restriction Requirement dated Sep. 14, 2012, which issued during the prosecution of U.S. Appl. No. 12/795,192.
Notice of Allowance dated Dec. 24, 2014, which issued during the prosecution of U.S. Appl. No. 12/795,026.
An Office Action dated Sep. 28, 2011, which issued during the prosecution of U.S. Appl. No. 12/437,103.
An International Search Report and Written Opinion dated Nov. 8, 2010, which issued during the prosecution of Applicant's PCT/IL2010/000358.
An Office Action dated Dec. 29, 2011, which issued during the prosecution of U.S. Appl. No. 12/563,952.
An International Search Report and a Written Opinion both dated Nov. 23, 2011, which issued during the prosecution of Applicant's PCT/IL2011/000446.
An International Search Report with Written Opinion both dated Feb. 2, 2012, which issued during the prosecution of Applicant's PCT/IL2011/000600.
An International Preliminary Report on Patentability dated Nov. 9, 2011 which issued during the prosecution of Applicant's PCT/IL/2010/000358.
An Office Action dated Aug. 4, 2010, which issued during the prosecution of U.S. Appl. No. 12/341,960.
An Office Action dated Nov. 14, 2011, which issued during the prosecution of U.S. Appl. No. 12/608,316.
An Office Action dated Aug. 15, 2013, which issued during the prosecution of U.S. Appl. No. 12/795,192.
An Office Action dated Jan. 17, 2013, which issued during the prosecution of U.S. Appl. No. 12/795,192.
An Office Action dated Feb. 12, 2013, which issued during the prosecution of U.S. Appl. No. 12/926,673.
Notice of Allowance dated Dec. 7, 2011, which issued during the prosecution of U.S. Appl. No. 12/435,291.
A Restriction Requirement dated Oct. 27, 2011, which issued during the prosecution of U.S. Appl. No. 12/563,952.
A Notice of Allowance dated May 24, 2012, which issued during the prosecution of U.S. Appl. No. 12/563,952.
A Restriction Requirement dated Jul. 5, 2012, which issued during the prosecution of U.S. Appl. No. 12/563,930.
A Notice of Allowance dated Apr. 3, 2013, which issued during the prosecution of U.S. Appl. No. 12/563,930.
An Office Action dated Apr. 2, 2013, which issued during the prosecution of U.S. Appl. No. 12/785,717.
An Advisory Action dated Sep. 6, 2012 which issued during the prosecution of U.S. Appl. No. 12/548,991.
A Restriction Requirement dated Feb. 4, 2013 which issued during the prosecution of U.S. Appl. No. 13/141,606.
An Office Action dated Feb. 14, 2013 which issued during the prosecution of U.S. Appl. No. 13/167,492.
An International Search Report and a Written Opinion both dated Feb. 22, 2013, which issued during the prosecution of Applicant's PCT/IL201/050451.
An Office dated Apr. 1, 2013 which issued during the prosecution of U.S. Appl. No. 13/167,476.
A Restriction Requirement dated Jun. 7, 2013 which issued during the prosecution of U.S. Appl. No. 13/141,606.
An Office Action dated Aug. 23, 2013 which issued during the prosecution of U.S. Appl. No. 13/167,444.
U.S. Appl. No. 61/265,936, filed Dec. 2, 2009.
U.S. Appl. No. 61/283,445, filed Dec. 2, 2009.
U.S. Appl. No. 61/207,908, filed Feb. 17, 2009.
Amplatzer Cardiac Plug brochure (English pages), AGA Medical Corporation (Plymouth, MN) (copyright 2008-2010, downloaded Jan. 11, 2011).
An Office Action dated Dec. 16, 2013, which issued during the prosecution of U.S. Appl. No. 13/666,262.
Notce of Allowance dated Nov. 19, 2013, which issued during the prosecution of U.S. Appl. No. 12/795,192.
An Office Action dated Oct. 2, 2013, which issued during the prosecution of U.S. Appl. No. 13/167.492.
An Office Action dated Nov. 21, 2013, which issued during the prosecution of U.S. Appl. No. 13/167,476.
An Office Action dated Dec. 18, 2013. which issued during the prosecution of U.S. Appl. No. 13/666,141.
A Restriction Requirement dated Apr. 19, 2010 which issued during the prosecution of U.S. Appl. No. 12/341,960.
An Office Action dated Jun. 13, 2012, which issued during the prosecution of U.S. Appl. No. 12/437,103.
An Office Action dated Nov. 30, 2012, which issued during the prosecution of U.S. Appl. No. 12/689,635.
An Office Action dated Oct. 22, 2013, which issued during the prosecution of U.S. Appl. No. 12/926,673.
A Restriction Requirement dated Oct. 25, 2012 which issued during the prosecution of U.S. Appl. No. 13/167,444.
An Office Action dated Jan. 17, 2013, which issued during the prosecution of U.S. Appl. No. 13/167,444.
A Restriction Requirement dated Nov. 2, 2012, which issued during the prosecution of U.S. Appl. No. 13/167,492.
An International Preliminary Report on Patentability dated Feb. 4, 2014, which issued during the prosecution of Applicant's PCT/IL2011/000446.
A Supplementary European Search Report dated Dec. 4, 2012, which issued during the prosecution of European Patent Application No. EP 09834225.6.
A Supplementary European Search Report dated Mar. 28, 2013, which issued during the prosecution of European Patent Application No. EP 1077 2091.4.
U.S. Appl. No. 61/713,979, filed Dec. 6, 2012.
U.S. Appl. No. 61/717,303, filed Oct. 23, 2012.
U.S. Appl. No. 61/820,979, filed May 8, 2013.
U.S. Appl. No. 61/745,848, filed Dec. 6, 2012.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated Dec. 27, 2013, which issued during the prosecution of U.S. Appl. No. 12/785,717.
An Office Action dated May 30, 2012, which issued during the prosecution of U.S. Appl. No. 12/706,868.

(56) References Cited

OTHER PUBLICATIONS

An Office Action dated Apr. 7, 2015, which issued during the prosecution of U.S. Appl. No. 13/319,007.
An International Preliminary Report on Patentability dated Jan. 29, 2013, which issued during the prosecution of Applicant's PCT/IL2011/000600.
An International Search Report and a Written Opinion both dated Dec. 6, 2012 which issued during the prosecution of Applicant's PCT/IL2012/000250.
Notice of Allowance dated Nov. 13, 2014, which issued during the prosecution of U.S. Appl. No. 12/795,026.
U.S. Appl. No. 61/557,082, filed Nov. 8, 2011.
A Restriction Requirement dated Jul. 12, 2011, which issued during the prosecution of U.S. Appl. No. 12/437,103.
An Office Action dated Mar. 27, 2013, which issued during the prosecution of U.S. Appl. No. 12/843,412.
An Office Action dated May 6, 2013, which issued during the prosecution of U.S. Appl. No. 12/689,693.
A Restriction Requirement dated May 1, 2012, which issued during the prosecution of U.S. Appl. No. 12/843,412.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
U.S. Appl. No. 61/555,570, filed Nov. 4, 2011.
A Notice of Allowance dated Sep. 18, 2012, which issued during the prosecution of U.S. Appl. No. 12/706,868.
An Office Action dated, Aug. 13, 2012, which issued during the prosecution of U.S. Appl. No. 13/044,694.
An Office Action dated, Dec. 31, 2012, which issued during the prosecution of U.S. Appl. No. 13/044,694.
A Restriction Requirement dated Apr. 1, 2011, which issued during the prosecution of U.S. Appl. No. 12/608,316.
Agarwal et al. International Cardiology Perspective Functional Tricuspid Regurgitation, Circ Cardiovasc Interv 2009;2;2;565-573 (2009).
An Office Action dated Oct. 6, 2010, which issued during the prosecution of Applicant's U.S. Appl. No. 12/484,512.
An Office Action dated Jul. 6, 2012, which issued during the prosecution of U.S. Appl. No. 12/692,061.
An Interview Summary dated Jul. 27, 2011, which issued during the prosecution of U.S. Appl. No. 12/341,960.
A Notice of Allowance dated May 2, 2013, which issued during the prosecution of U.S. Appl. No. 12/843,412.
An Office Action dated Jul. 18, 2013, which issued during the prosecution of U.S. Appl. No. 13/044,694.
Search Report in European Patent Application 10772090.6 dated Jan. 17, 2014.
An Office Action dated Feb. 3, 2014, which issued during the prosecution of U.S. Appl. No. 12/689,693.
Communication regarding amended claims filed dated Dec. 27, 2012, regarding European App No. 11792047.0.
Notice of Allowance dated Mar. 6, 2014, which issued during the prosecution of U.S. Appl. No. 12/437,103.
An Office Action dated Oct. 9, 2013, which issued during the prosecution of U.S. Appl. No. 12/996,954.
AMPLATZER® Septal Occluder. A patient guide to the Non-Surgical Closuer of the Atrial Septal Defect Using the AMPLATZER Septal Occluder System, AGA Medical Corporation, Apr. 2008.
Notice of Allowance dated Sep. 12, 2014, which issued during the prosecution of U.S. Appl. No. 11/950,930.
An Office Action dated Dec. 19, 2013, which issued during the prosecution of U.S. Appl. No. 14/027,934.
An International Preliminary Report on Patentability dated Dec. 18, 2010, which issued during the prosecution of Applicant's PCT/IL09/00593.
An English translation of an Office Action dated Apr. 23, 2014 which issued during the prosecution of Chinese Patent Application No. 201080059948.4.
Notice of Allowance dated Jun. 23, 2014, which issued during the prosecution of U.S. Appl. No. 12/548,991.
Notice of Allowance dated Jun. 11, 2014, which issued during the prosecution of U.S. Appl. No. 12/689,693.
Notice of Allowance dated Jun. 25, 2014, which issued during the prosecution of U.S. Appl. No. 13/666,262.
An International Search Report and Written Opinion both dated Apr. 9, 2014, which issued during the prosecution of Applicant's PCT/IL13/50860.
Notice of Allowance dated Nov. 7, 2014, which issued during the prosecution of U.S. Appl. No. 13/167,492.
An Office Action dated Jun. 11, 2014, which issued during the prosecution of U.S. Appl. No. 14/027,934.
A Restriction Requirement dated Jun. 2, 2014, which issued during the prosecution of U.S. Appl. No. 13/319,030.
Brennan, Jennifer, 510(k) Summary of safety and effectiveness, Jan. 2008.
A communication from the European Patent Office dated Sep. 28, 2011 which issued during the prosecution of European Application No. 09834225.6.
A Restriction Requirement dated Sep. 17, 2012, which issued during the prosecution of U.S. Appl. No. 12/689,693.
An Office Action dated Aug. 22, 2014, which issued during the prosecution of U.S. Appl. No. 14/027,934.
An Office Action dated Aug. 26, 2014 which issued during the prosecution the prosecution of U.S. Appl. No. 13/167,444.
Communication dated Jul. 25, 2014, issued by the State Intellectual Property Office of the P.R. of China in counterpart Application No. 200980157331.3.
An Office Action dated Oct. 14, 2014, which issued during the prosecution of U.S. Appl. No. 13/319,030.
Supplementary European Search Report dated Oct. 23, 2014 which issued during the prosecution of Applicant's European App No. 10826224.7.
An International Search Report & Written Opinion both dated Mar. 21, 2014, which issued during the prosecution of Applicant's PCT/IL13/50992.
An Office Action dated Sep. 29, 2014, which issued during the prosecution of U.S. Appl. No. 13/504,870.
An Office Action dated Oct. 3, 2014, which issued during the prosecution of U.S. Appl. No. 13/749,153.
An International Search Report & Written Opinion both dated Sep. 8, 2009, which issued during the prosecution of Applicant's PCT/IL09/00593.
An International Preliminary Report on Patentability dated Jun. 10, 2009, which issued during the prosecution of Applicant's PCT/IL07/01503.
Notice of Allowance dated Jan. 22, 2015, which issued during the prosecution of U.S. Appl. No. 13/167,444.
Notice of Allowance dated Dec. 9, 2014, which issued during the prosecution of U.S. Appl. No. 13/167,476.
An English translation of an Office Action dated Dec. 12, 2013 which issued during the prosecution of Chinese Patent Application No. 200980157331.3.
An International Search Report and a Written Opinion both dated Nov. 14, 2011, which issued during the prosecution of Applicant's PCT/IL2011/000404.
Dictionary.com definition of "lock", Jul. 29, 2013.
A Restriction Requirement dated Jan. 6, 2012, which issued during the prosecution of U.S. Appl. No. 12/795,026.
A Restriction Requirement dated Nov. 14, 2011 which issued during the prosecution of U.S. Appl. No. 12/548,991.
An Office Action dated Jan. 13, 2015, which issued during the prosecution of U.S. Appl. No. 13/707,013.
A Notice of Allowance dated May 22, 2013, which issued during the prosecution of U.S. Appl. No. 12/689,635.
An International Preliminary Report on Patentability dated May 1, 2012, which issued during the prosecution of Applicant's PCT/IL2010/000890.

(56) References Cited

OTHER PUBLICATIONS

A Notice of Allowance dated Jan. 7, 2014, which issued during the prosecution of U.S. Appl. No. 12/926,673.
Restriction Requirement dated May 5, 2011, which issued during the prosecution of U.S. Appl. No. 12/706,868.
Supplementary European Search Report dated Aug. 4, 2014 which issued during the prosecution of Applicant's European App No. 11 81 1934.6.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
Restriction Requirement dated Nov. 14. 2011, which issued during the prosecution of U.S. Appl. No. 12/689,635.
Supplementary European Search Report dated Jan. 21, 2014 which issued during the prosecution of Applicant's European App No. 11 78 6226.
An Office Action dated Jun. 4, 2014, which issued during the prosecution of U.S. Appl. No. 12/840,463.
Maisano, The double-orifice technique as a standardized approach to treat mitral . . . European Journal of Cardio-thoracic Surgery 17 (2000) 201-205.
AMPLATZER® Cribriform Occluder. A patient Guide to Percutaneous, Transcatheter, Atrial Septal Defect Ciosuer, AGA Medical Corporation, Apr. 2008.
An Office Action dated Jun. 10, 2014, which issued during the prosecution of U.S. Appl. No. 13/167,492.
Supplementary European Search Report dated Sep. 25, 2015, which issued during the prosecution of Applicant's European App No. 09794095.1.
An Office Action dated Apr. 2, 2015, which issued during the prosecution of U.S. Appl. No. 14/027,934.
An Office Action dated Mar. 23, 2015, which issued during the prosecution of U.S. Appl. No. 13/707,013.
Supplementary European Search Report dated Dec. 23, 2014 which issued during the prosecution of Applicant's European App No. 10834311.
An Office Action dated Mar. 24, 2015, which issued during the prosecution of U.S. Appl. No. 12/996,954.
Notice of Allowance dated Dec. 20, 2013, which issued during the prosecution of U.S. Appl. No. 12/437,103.
An International Preliminary Report on Patentability dated Dec. 23, 2014, which issued during the prosecution of Applicant's PCT/IL2012/050451.
An International Preliminary Report on Patentability dated Dec. 23, 2013, which issued during the prosecution of Applicant's PCT/IL2012/000250.
An Office Action dated Oct. 5, 2015, which issued during the prosecution of U.S. Appl. No. 14/246,417.
An Office Action dated Aug. 7, 2015, which issued during the prosecution of U.S. Appl. No. 14/128,756.
An Invitation to pay additional fees dated Jan. 31, 2014, which issued during the prosecution of Applicant's PCT/IL2013/050861.
An Invitation to pay additional fees dated Jan. 31, 2014, which issued during the prosecution of Applicant's PCT/IL2013/050860.
An Office Action dated Sep. 19, 2014, which issued during the prosecution of U.S. Appl. No. 13/044,694.
A communication from the European Patent Office dated Oct. 19, 2012 which issued during the prosecution of European Application No. 11792047.0.
An Office Action dated. Oct. 5, 2012, which issued during the prosecution of U.S. Appl. No. 12/996,954.
An Office Action dated Oct. 1, 2015, which issued during the prosecution of U.S. Appl. No. 14/141,228.
Notice of Allowance dated May 6, 2016, which issued during the prosecution of U.S. Appl. No. 14/667,090.
Notice of Allowance dated Apr. 12, 2016, which issued during the prosecution of U.S. Appl. No. 14/667,090.

Amendment, Terminal Disclaimer and Extension dated Jun. 27, 2012, which issued during the prosecution of U.S. Appl. No. 12/548,991.
An Office Action dated Jun. 18, 2015, which issued during the prosecution of U.S. Appl. No. 14/551,951.
A Notice of Allowance dated Feb. 2, 2015, which issued during the prosecution of U.S. Appl. No. 13/504,870.
An Office Action dated Jan. 5, 2016, which issued during the prosecution of U.S. Appl. No. 14/027,934.
An Office Action dated Mar. 16, 2015, which issued during the prosecution of U.S. Appl. No. 14/084,426.
European Search Report dated Jun. 24, 2016, which issued during the prosecution of European Patent Application No. EP 12847363.
An Office Action dated Mar. 24, 2015, which issued during the prosecution of U.S. Appl. No. 14/486,226.
An Office Action dated Jul. 20, 2016, which issued during the prosecution of U.S. Appl. No. 14/246,417.
Notice of Allowance dated May 22, 2015, which issued during the prosecution of U.S. Appl. No. 13/749,153.
An Office Action dated Jun. 18, 2015, which issued during the prosecution of U.S. Appl. No. 13/319,030.
An Office Action dated Jun. 13, 2014, which issued during the prosecution of U.S. Appl. No. 13/141,606.
An English translation of an Office Action dated Jul. 17, 2015 which issued during the prosecution of Chinese Patent Application No. 201080059948.4.
Notice of Allowance dated Sep. 29, 2014, which issued during the prosecution of U.S. Appl. No. 13/141,606.
An International Search Report and a Written Opinion both dated Oct. 27, 2016, which issued during the prosecution of Applicant's PCT/IL2015/050792.
An International Preliminary Report on Patentability dated Jun. 9, 2015, which issued during the prosecution of Applicant's PCT/IL2013/050992.
An Office Action dated May 3, 2016, which issued during the prosecution of U.S. Appl. No. 13/319,030.
A Notice of Allowance dated. Sep. 2, 2016, which issued during the prosecution of U.S. Appl. No. 14/027,934.
An Office Action dated Feb. 3, 2015, which issued during the prosecution of U.S. Appl. No. 14/084,426.
Search Report in European Patent Application 10826224.7 dated Nov. 16, 2015.
An International Preliminary Report on Patentability dated Apr. 28, 2015, which issued during the prosecution of Applicant's PCT/IL2013/050861.
An English Translation of an Office Action dated Nov. 24, 2015, which issued during the prosecution of Israel Patent Application No. 223448. (the relevant part only).
Notice of Allowance dated Nov. 12, 2015, which issued during the prosecution of U.S. Appl. No. 13/319,007.
Notice of Allowance dated Jan. 7, 2016, which issued during the prosecution of U.S. Appl. No. 13/319,007.
Notice of Allowance dated Apr. 20, 2011, which issued during the prosecution of U.S. Appl. No. 12/484,512.
Notice of Allowance dated Mar. 23, 2011, which issued during the prosecution of U.S. Appl. No. 12/484,512.
An Office Action dated May 23, 2016, which issued during the prosecution of U.S. Appl. No. 14/209,171.
European Search Report dated Jul. 8, 2016, which issued during the prosecution of Applicant's European App No. 13849843.1.
Notice of Allowance dated Nov. 23, 2016, which issued during the prosecution of U.S. Appl. No. 14/141,228.
Supplementary European Search Report dated Mar. 23, 2015, which issued during the prosecution of Applicant's European App No. 11792047.0.
Supplementary European Search Report dated Apr. 29, 2015, which issued during the prosecution of Applicant's European App No. 14200202.
An International Search Report and a Written Opinion both dated Apr. 15, 2014, which issued during the prosecution of Applicant's PCT/IL2013/050861.
Notice of Allowance dated Nov. 17, 2015, which issued during the prosecution of U.S. Appl. No. 14/486,226.

(56) References Cited

OTHER PUBLICATIONS

European Search Report dated Nov. 4, 2015, which issued during the prosecution of European Patent Application No. EP 1077 2091.4.
Notice of Allowance dated Dec. 19, 2016, which issued during the prosecution of U.S. Appl. No. 14/242,151.
European Search Report dated Jul. 15, 2016, which issued during the prosecution of Applicant's European App No. 13849947.0.
An Office Action dated Jun. 17, 2016, which issued during the prosecution of U.S. Appl. No. 14/357,040.
Notice Notice of Allowance dated Dec. 30, 2016, which issued during the prosecution of U.S. Appl. No. 13/319,030.
An Office Action dated Mar. 23, 2015, which issued during the prosecution of European Patent Application No. EP 09834225.6.
Notice of Allowance dated Aug. 3, 2015, which issued during the prosecution of U.S. Appl. No. 13/749,153.
A Notice of Allowance dated Sep. 16, 2016, which issued during the prosecution of U.S. Appl. No. 14/027,934.
A Notice of Allowance dated Jul. 30, 2015, which issued during the prosecution of U.S. Appl. No. 13/319,007.
A Notice of Allowance dated Sep. 3, 2014, which issued during the prosecution of U.S. Appl. No. 12/689,693.
An International Preliminary Report on Patentability dated Apr. 28 2015, which issued during the prosecution of Applicant's PCT/IL2013/050860.
An Office Action dated Jan. 6, 2016, which issued during the prosecution of U.S. Appl. No. 14/128,756.
An Office Action dated Apr. 8, 2016, which issued during the prosecution of U.S. Appl. No. 14/141,228.
An Office Action dated Apr. 7, 2016, which issued during the prosecution of U.S. Appl. No. 14/242,151.
An Office Action dated Jan. 4, 2016, which issued during the prosecution of U.S. Appl. No. 14/589,100.
Communication from the European Patent Office dated Jun. 11, 2015, which issued during the prosecution of European Patent Application No. 11811934.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.
An Office Action dated Dec. 21, 2013, which issued during the prosecution of U.S. Appl. No. 11/908,906.
A Restriction Requirement dated Aug. 5, 2011, which issued during the prosecution of U.S. Appl. No. 11/908,906.
An Office Action dated Oct. 23, 2012, which issued during the prosecution of Japanese Patent Application No. 2009-539871.
U.S. Appl. No. 60/662,616, filed Mar. 17, 2005.
U.S. Appl. No. 60/700,542, filed Jul. 18, 2005.
An Office Action dated May 4, 2016, which issued during the prosecution of U.S. Appl. No. 14/589,100.
An Office Action dated Jun. 14, 2016, which issued during the prosecution of U.S. Appl. No. 14/273,155.
An International Search Report and a Written Opinion both dated Jan. 25, 2016, which issued during the prosecution of Applicant's PCT/IL2015/051027.
An Office Action dated Jan. 5, 2016, which issued during the prosecution of U.S. Appl. No. 14/084,426.
An International Preliminary Report on Patentability dated Apr. 26, 2016, which issued during the prosecution of Applicant's PCT/IL2014/050914.
An Office Action dated May 11, 2016, which issued during the prosecution of U.S. Appl. No. 14/128,756.
An English Translation of an Office Action dated Sep. 15, 2016, which issued during the prosecution of Israel Patent Application No. 243837. (the relevant part only).
Notice of Allowance dated Sep. 14, 2015, which issued during the prosecution of U.S. Appl. No. 13/707,013.
Notice of Allowance dated Jul. 24, 2015, which issued during the prosecution of U.S. Appl. No. 13/707,013.
Notice of Allowance dated Jul. 8, 2015. which issued during the prosecution of U.S. Appl. No. 13/707,013.
Ahmadi, Ali, et al. "Percutaneously adjustable pulmonary artery band." *The Annals of thoracic surgery* 60 (1995): S520-S522.
Assad. Renato S. "Adjustable Pulmonary Artery Banding." (2014).
Ahmadi A., G. Spllner, and Th Johannesson. "Heodynamic changes following experimental production and correction of acute mitral regurgitation with an adjustable ring prosthesis." *The Thoracic and cardiovascular surgeon*36.06 (1988): 313-319.
Swenson, Orvar. "Internal device for control of urinary incontinence." *Journal of pediatric surgery* 7.5 (1972): 542-545.
Park, Sang C., et al. "A percutaneously adjustable device for banding of the pulmonary trunk." *International journal of cardiology* 9.4 (1985): 477-484.
Elliott, Daniel S., Gerald W. Timm, and David M. Barrett. "An implantable mechanical urinary sphincter: a new nonhydraulic design concept." *Urology*52.6 (1998): 1151-1154.
An Invitation to pay additional fees dated Aug. 18, 2016, which issued during the prosecution of Applicant's PCT/IL2016/050433.
Daebritz, S., et al. "Experience with an adjustable pulmonary artery banding device in two cases: initial success-midterm failure." *The Thoracic and cardiovascular surgeon* 47.01 (1999): 51-52.
Notice of Allowance dated Mar. 1, 2017, which issued during the prosecution of U.S. Appl. No. 14/357,040.
An Office Action dated Sep. 6, 2016, which issued during the prosecution of U.S. Appl. No. 14/141,228.
An International Search Report and a Written Opinion both dated Oct. 17, 2016, which issued during the prosecution of Applicant's PCT/IL2016/050433.
An Office Action dated Oct. 21, 2016, which issued during the prosecution of U.S. Appl. No. 14/567,472.
Notice of Allowance dated Jul. 7, 2015, which issued during the prosecution of U.S. Appl. No. 12/996,954.
Notice Notice of Allowance dated Nov. 18, 2016, which issued during the prosecution of U.S. Appl. No. 13/740,582.
Notice of Allowance dated Oct. 20, 2015, which issued during the prosecution of U.S. Appl. No. 12/996,954.
Amendment and Extension dated Apr. 11, 2012, which issued during the prosecution of U.S. Appl. No. 12/563,952.
Notice of Allowance dated Dec. 8, 2016, which issued during the prosecution of U.S. Appl. No. 14/246,417.
Notice of Allowance dated Dec. 21, 2016, which issued during the prosecution of U.S. Appl. No. 14/246,417.
Notice of Allowance dated Dec. 29, 2016, which issued during prosecution of U.S. Appl. No. 14/246,417.
Notice of Allowance dated Jan. 3, 2017, which issued during the prosecution of U.S. Appl. No. 14/128,756.
Swenson, O. and Malinin, T.I., 1978. An improved mechanical device for control of urinary incontinence. *Investigative urology*, 15(5), pp. 389-391.
Swenson, O. An experimental implantable urinary sphincter. *Invest Urol*. Sep. 1976;14(2):100-3.
An International Preliminary which issued during the prosecution Report on Patentability dated Sep. 18, 2007, which issued during the prosecution of Applicant's PCT/IL2006/000342.
An International Search Report and a Written Opinion both dated May 30, 2007, which issued during the prosecution of Applicant's PCT/IL2006/000342.
An Advisory Action dated Feb. 4, 2014, which issued during the prosecution of U.S. Appl. No. 13/167,476.
An English Translation of an Office Action dated May 31, 2012, which issued during the prosecution of Israel Patent Application No. 209946. (the relevant part only).
A Restriction Requirement dated Jul. 8, 2015, which issued during the prosecution of U.S. Appl. No. 14/141,228.
Notice of Allowance dated Sep. 22, 2016, which issued during the prosecution of U.S. Appl. No. 13/740,582.
A Restriction Requirement dated Sep. 4, 2015, which issued during the prosecution of U.S. Appl. No. 14/589,100.
Notice of Allowance dated Jan. 29, 2016, which issued during the prosecution of U.S. Appl. No. 14/551,951.

(56) References Cited

OTHER PUBLICATIONS

An International Search Report and a Written Opinion both dated May 28, 2014, which issued during the prosecution of Applicant's PCT/IL14/050027.
An Office Action dated Aug. 22, 2016, which issued during the prosecution of U.S. Appl. No. 14/084,426.
An Office Action dated Dec. 20, 2016, which issued during the prosecution of UK Patent Application No. 1611910.9.
Notice of Allowance dated Aug. 7, 2015, which issued during the prosecution of Chinese Patent Application No. 200980157331.3.
An Office Action dated Jan. 20, 2017, which issued during the prosecution of U.S. Appl. No. 14/650,114.
An Office Action dated Feb. 27, 2017, which issued during the prosecution of U.S. Appl. No. 15/249,957.
An Office Action dated Feb. 2, 2017, which issued during the prosecution of U.S. Appl. No. 14/209,171.
An Office Action dated Jan. 25, 2017, which issued during the prosecution of Chinese Patent Application No. 201510681407.X.
An Office Action dated. Dec. 13, 2016, which issued during the prosecution of Applicant's European App No. 11786226.8.
An Interview Summary dated Apr. 4, 2012, which issued during the prosecution of U.S. Appl. No. 12/563,952.
An Office Action dated Mar. 3, 2017, which issued during the prosecution of Applicant's European App No. 11792047.0.
An Office Action dated May 28, 2015, which issued during the prosecution of U.S. Appl. No. 14/128,756.
An International Search Report & Written Opinion both dated May 12, 2015, which issued during the prosecution of Applicant's PCT/IL2014/050914.
Alfieri et al., "The edge to edge technique," The European Association for Cardio-Thoracic Surgery $14^{th}$ Annual Meeting Oct. 7-11, Book of Procees. (2000).
An Office Action dated Feb. 10, 2017, which issued during the prosecution of U.S. Appl. No. 14/990,172.
An Office Action dated Apr. 6, 2017, which issued during the prosecution of U.S. Appl. No. 14/437,062.
Notice of Allowance dated Apr. 13. 2017, which issued during the prosecution of U.S. Appl. No. 14/650,114.
An Office Action dated Mar. 24, 2017, which issued during the prosecution of U.S. Appl. No. 14/273,155.

\* cited by examiner

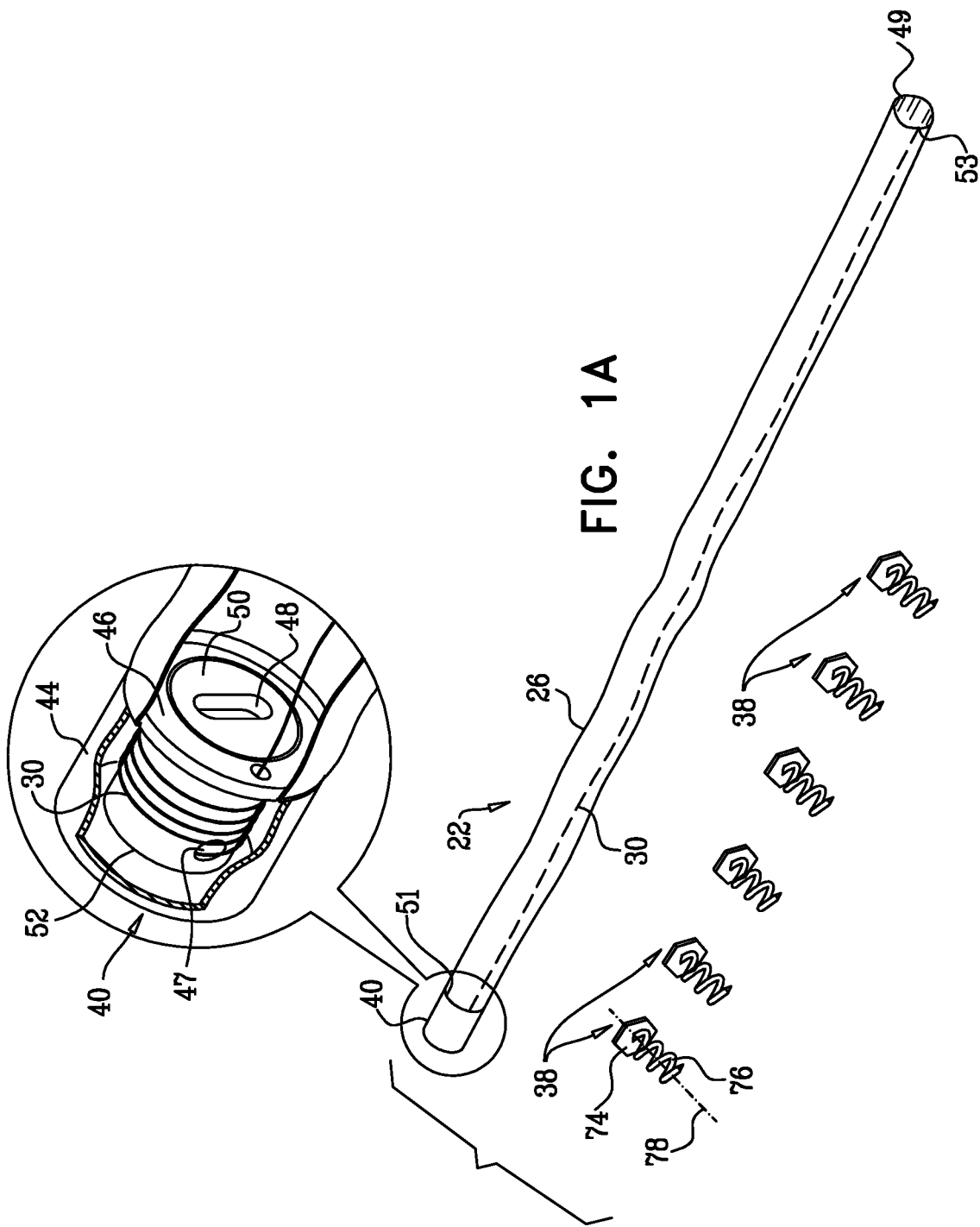

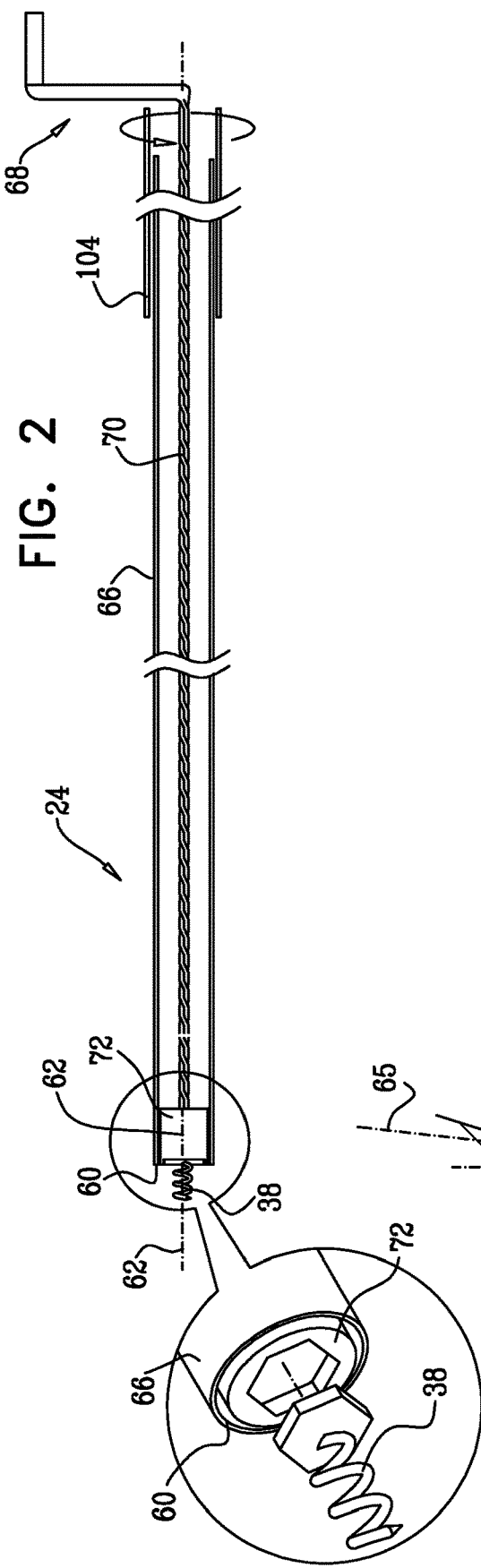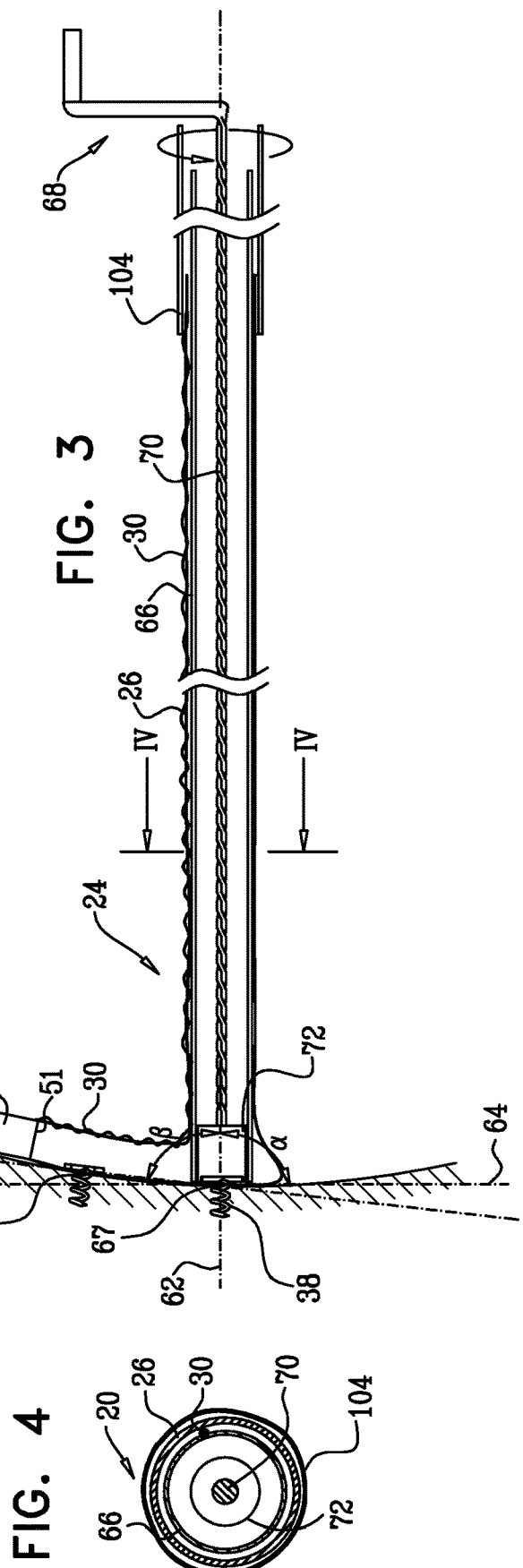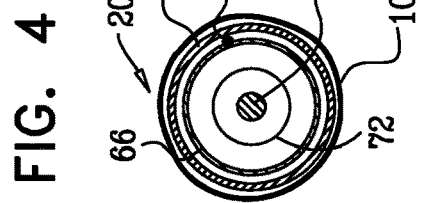

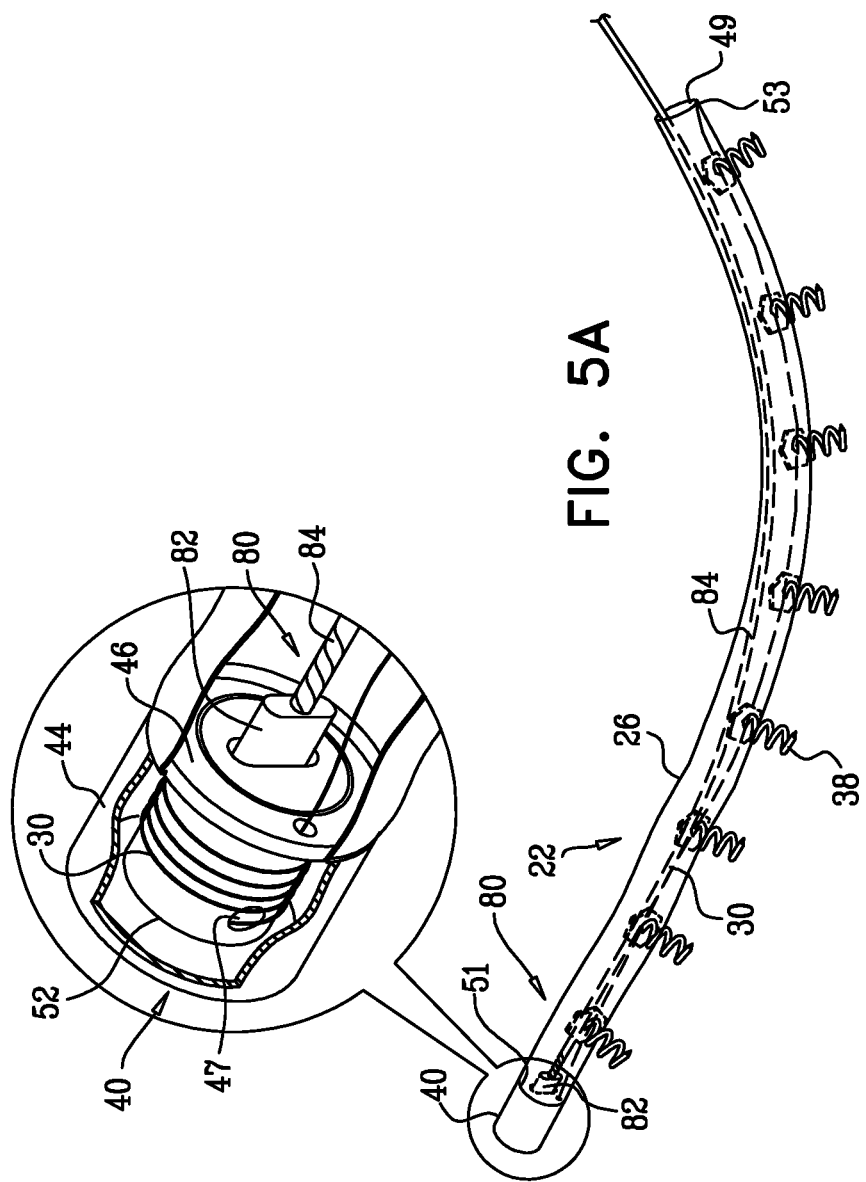

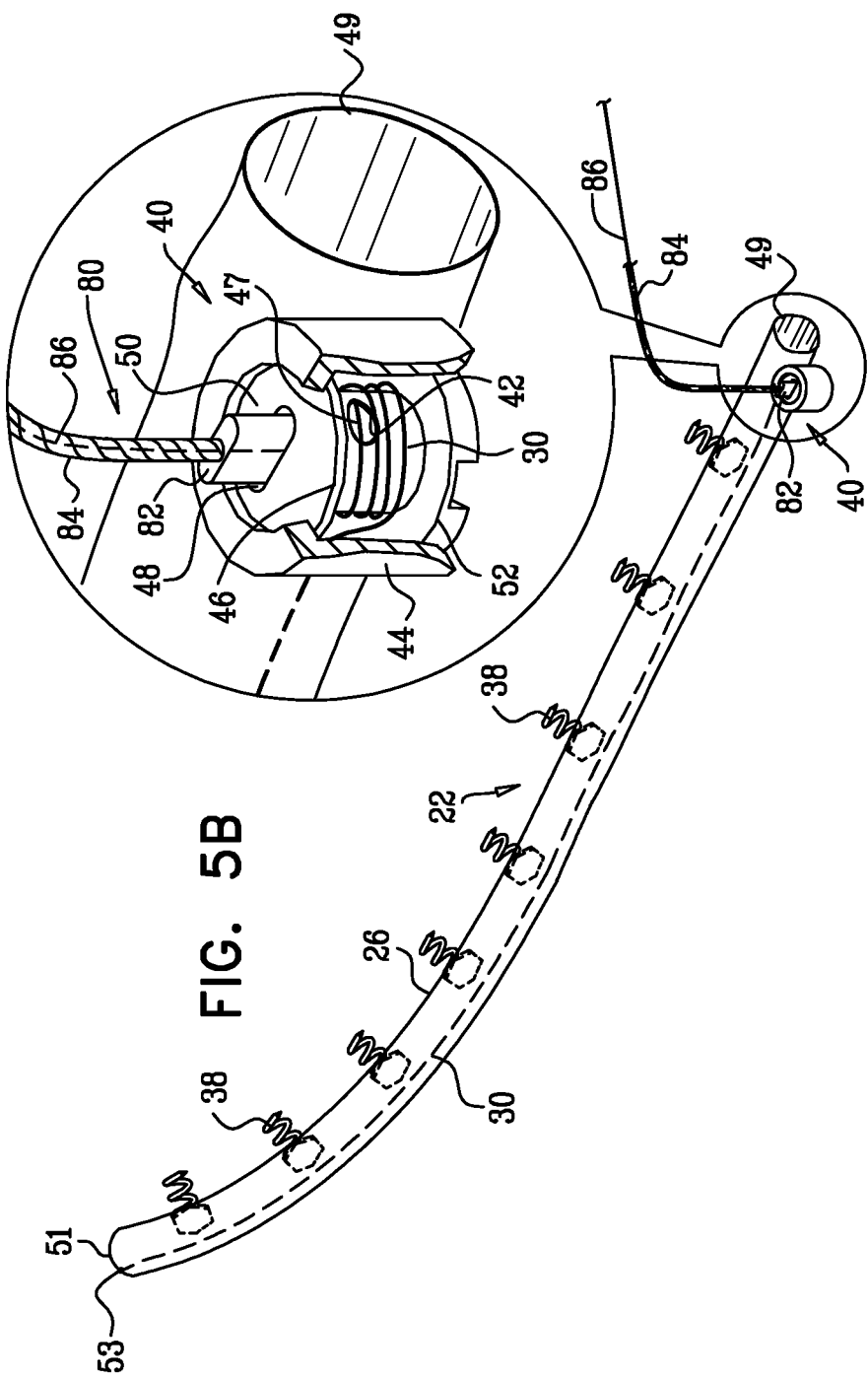

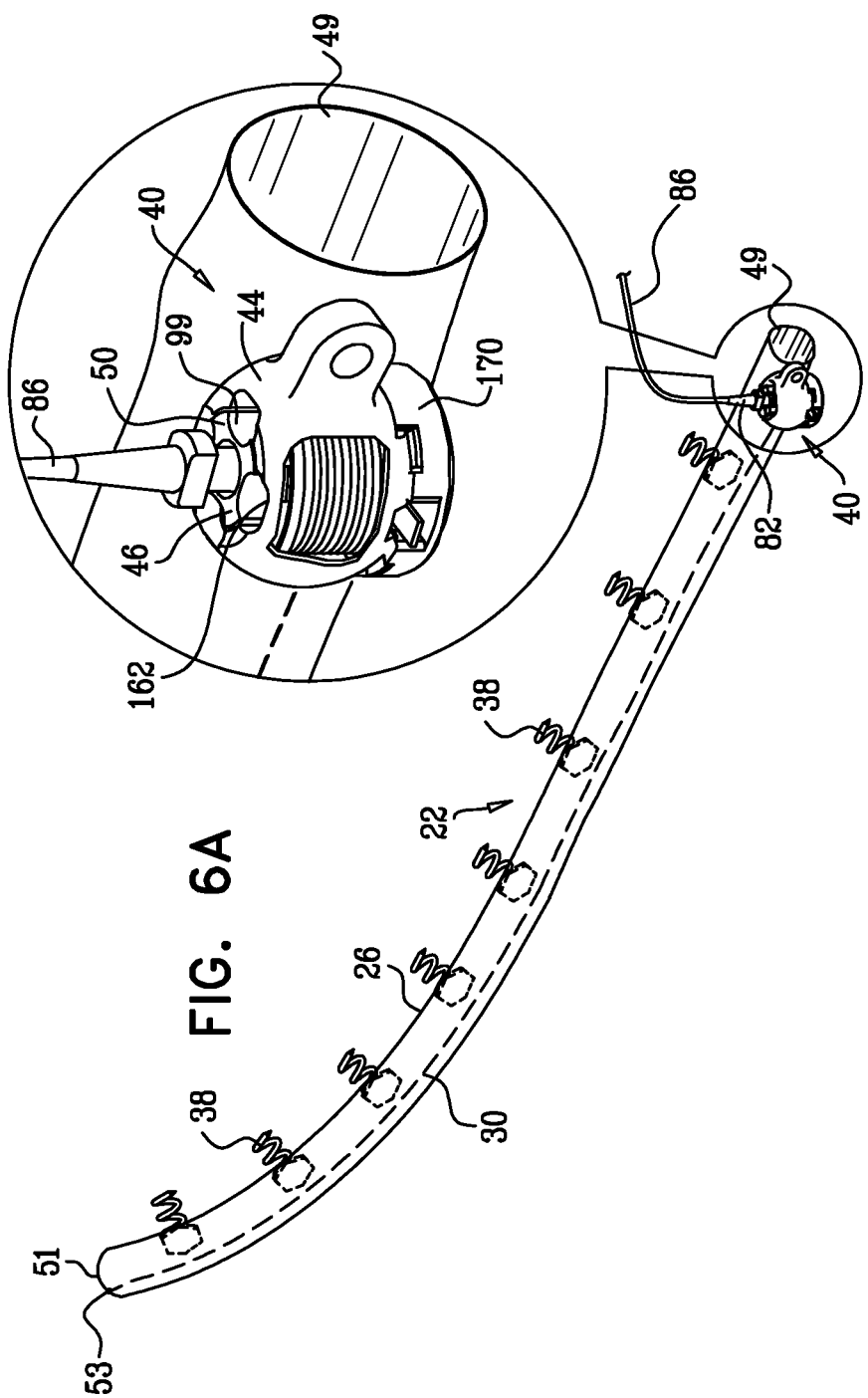

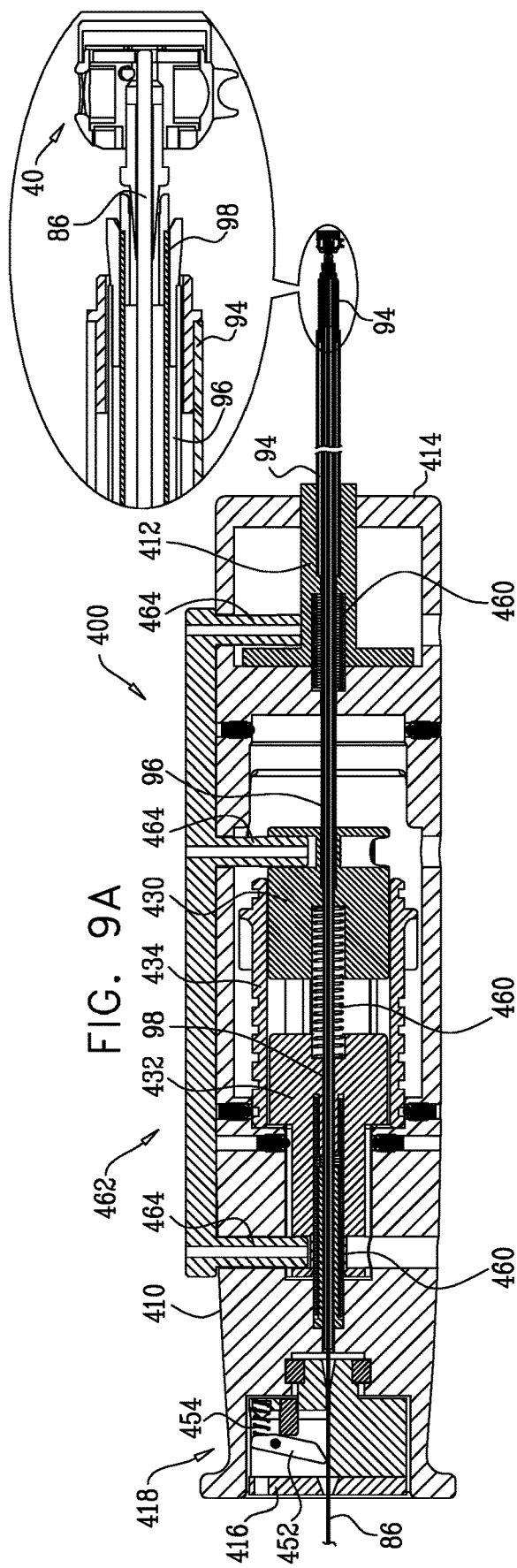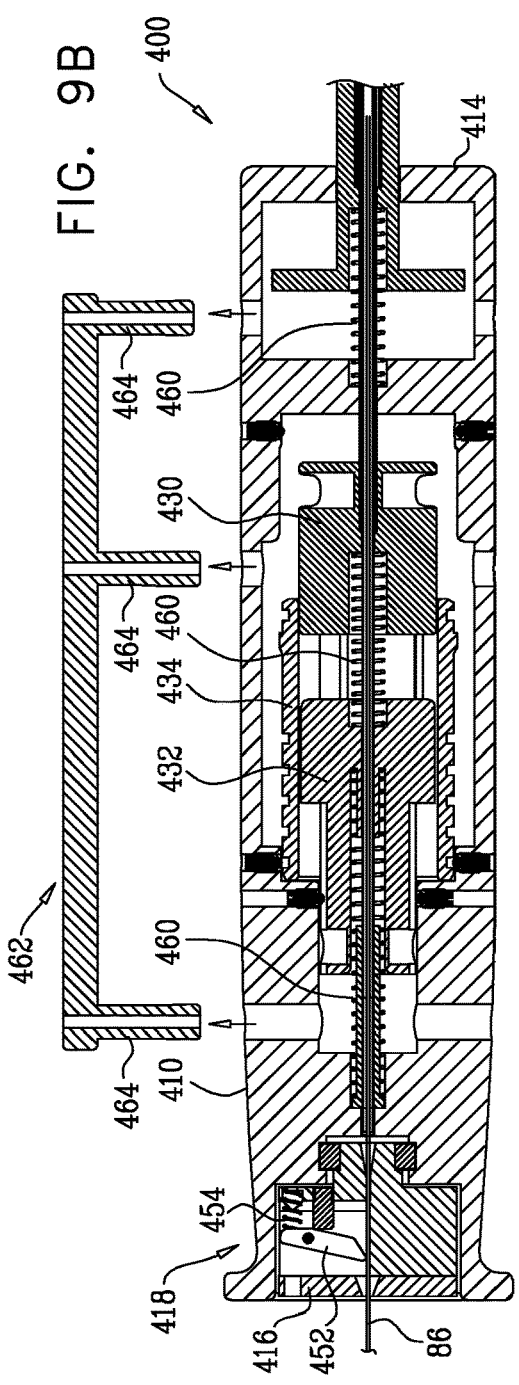

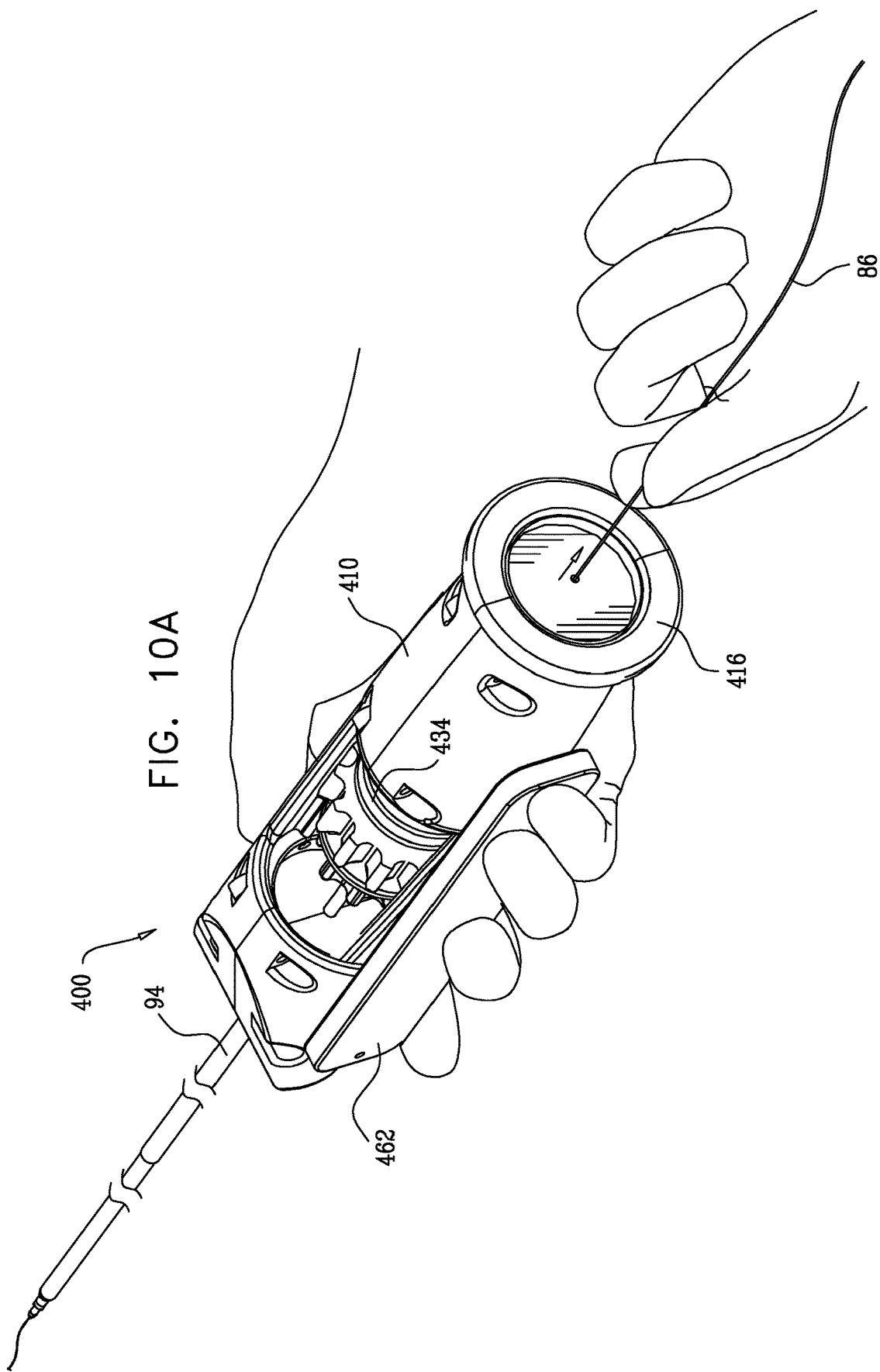

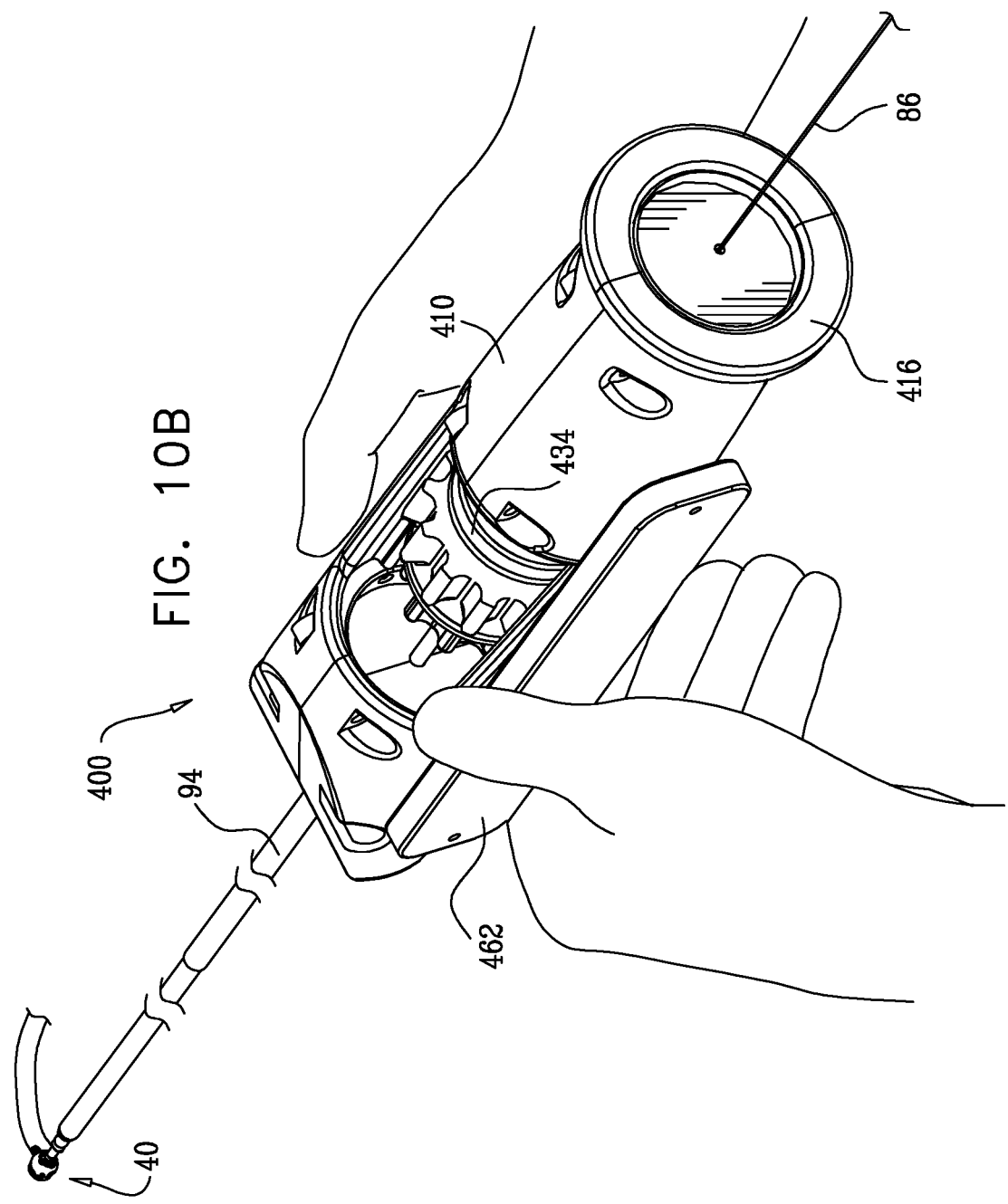

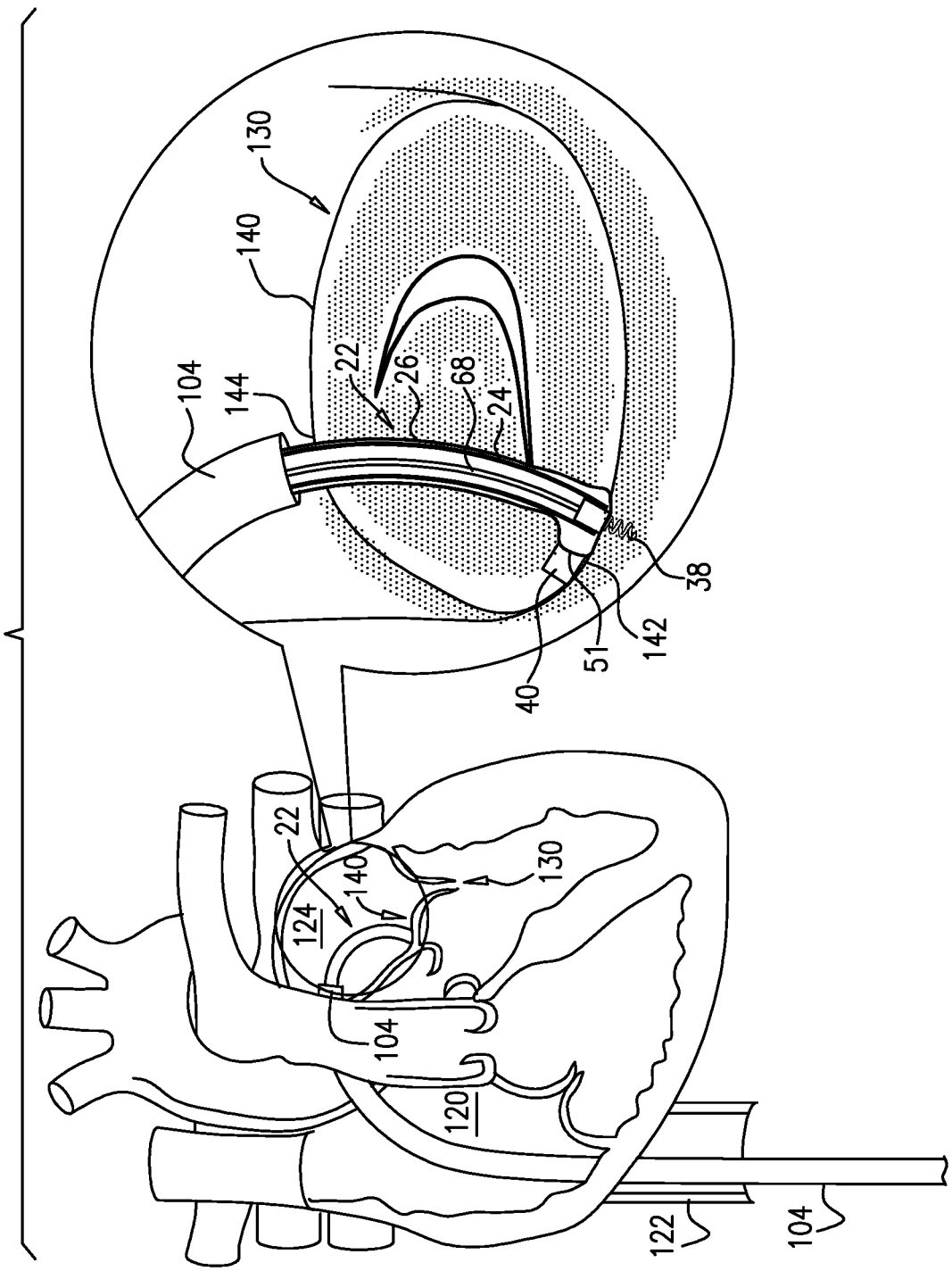

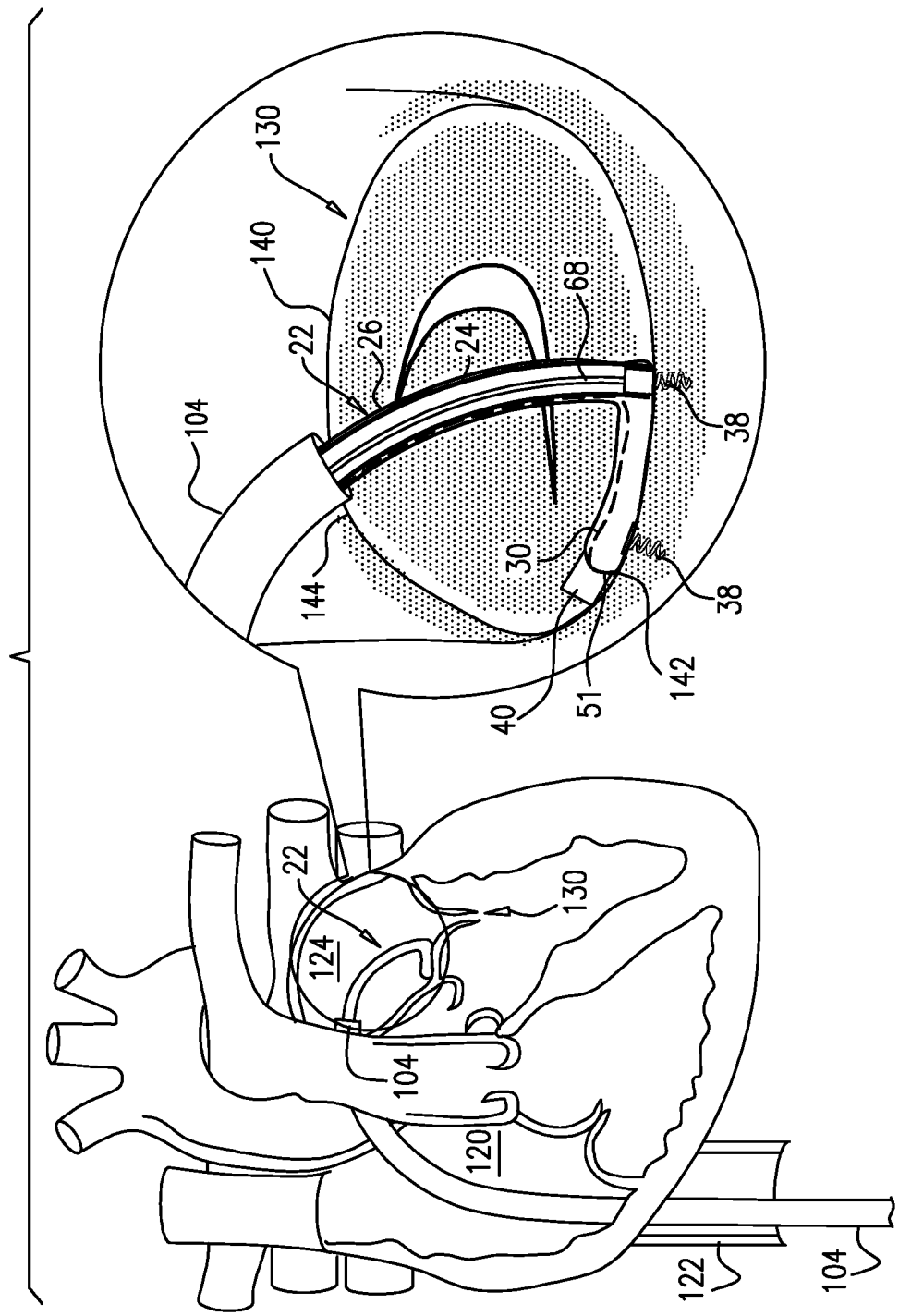

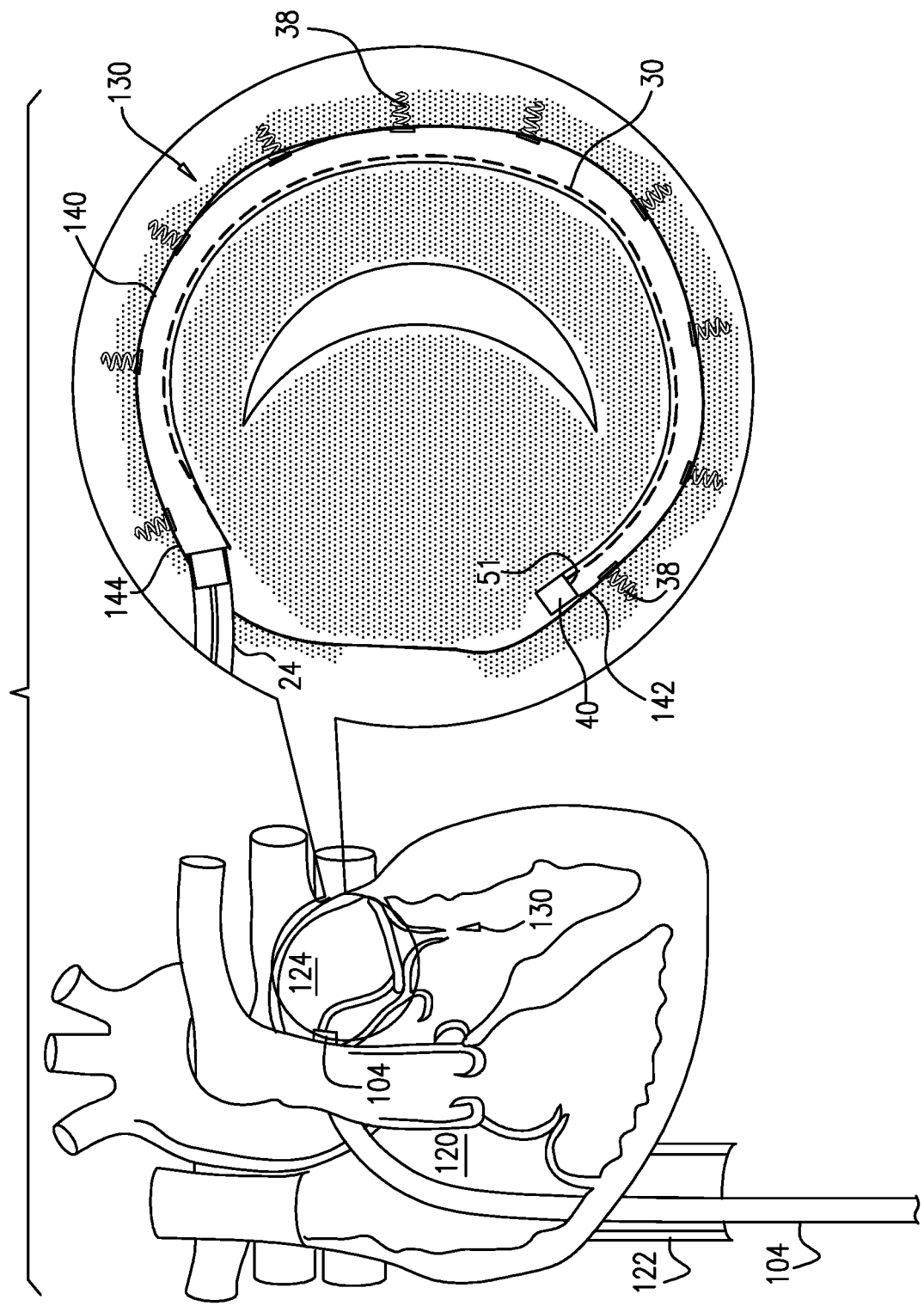

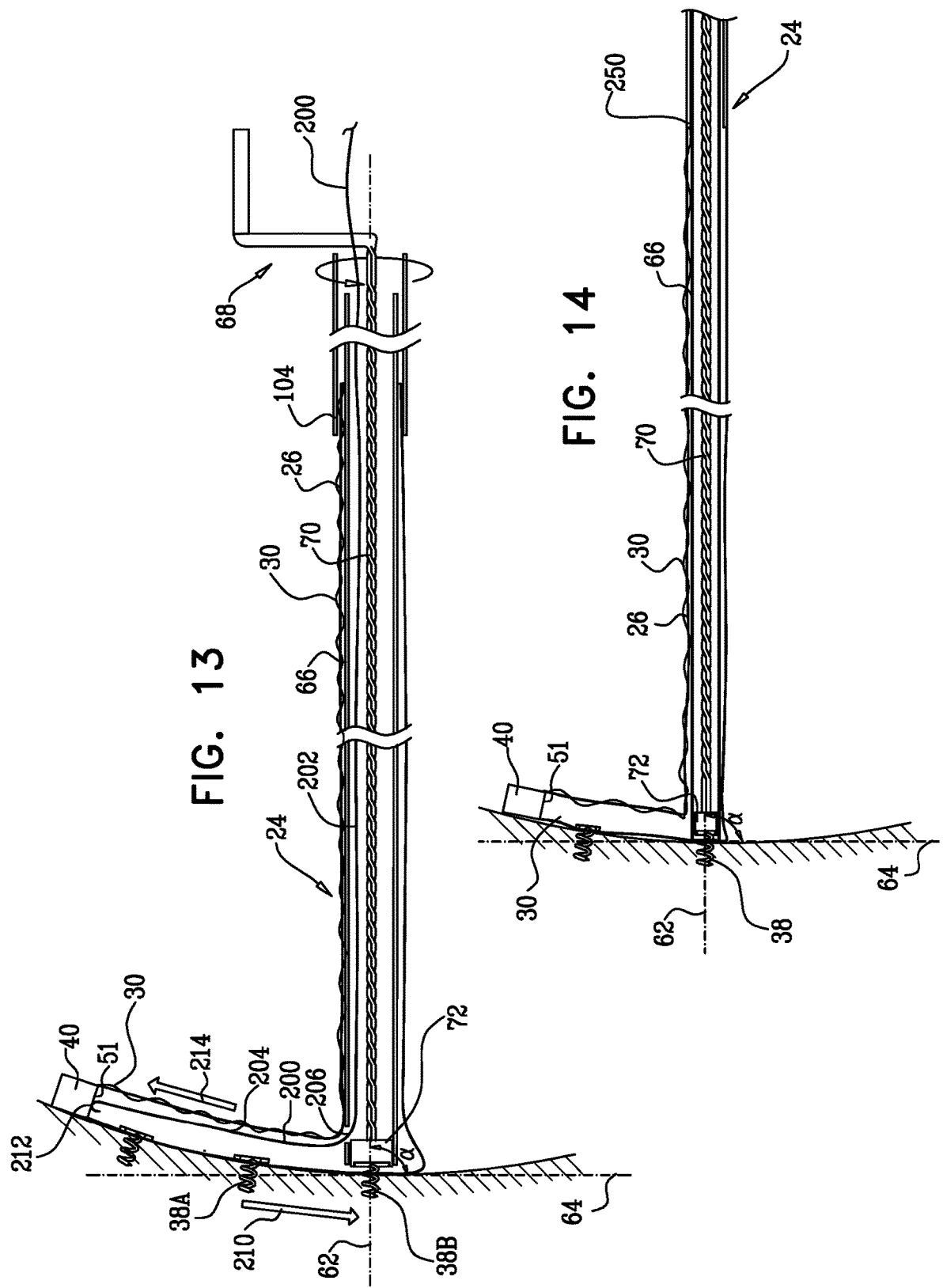

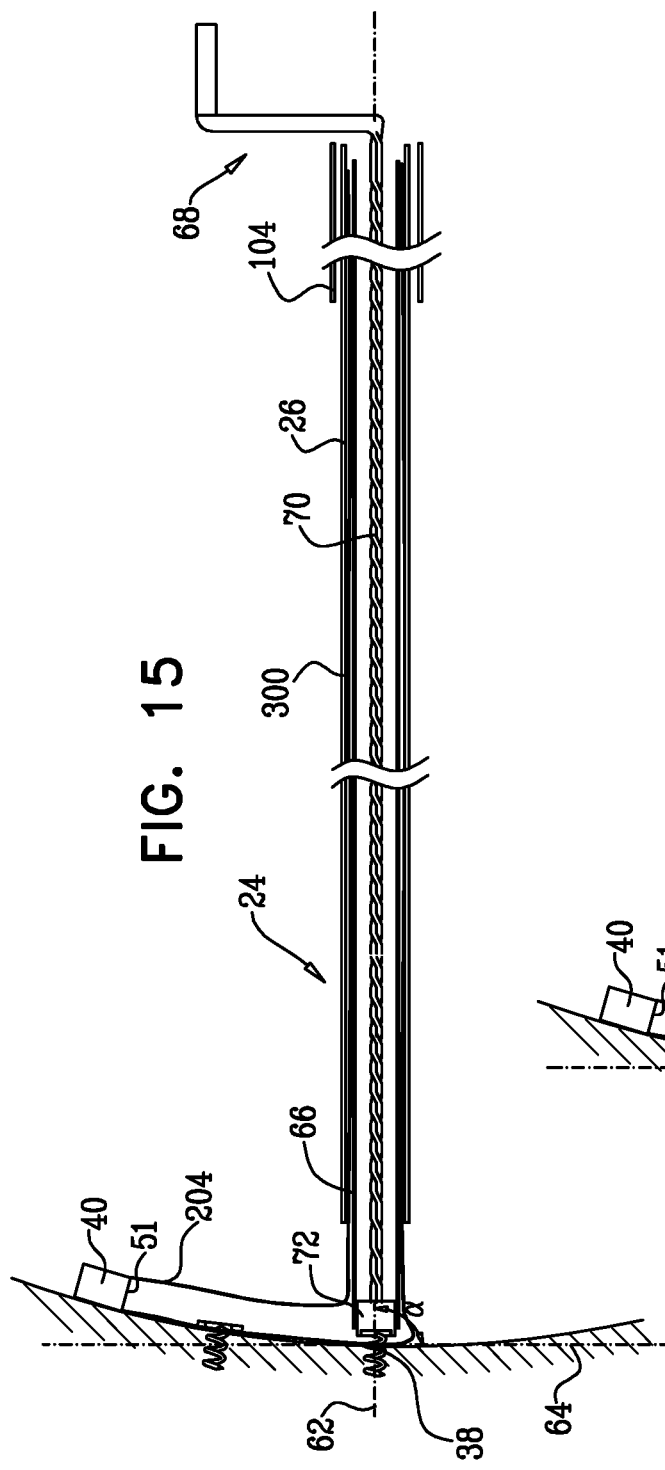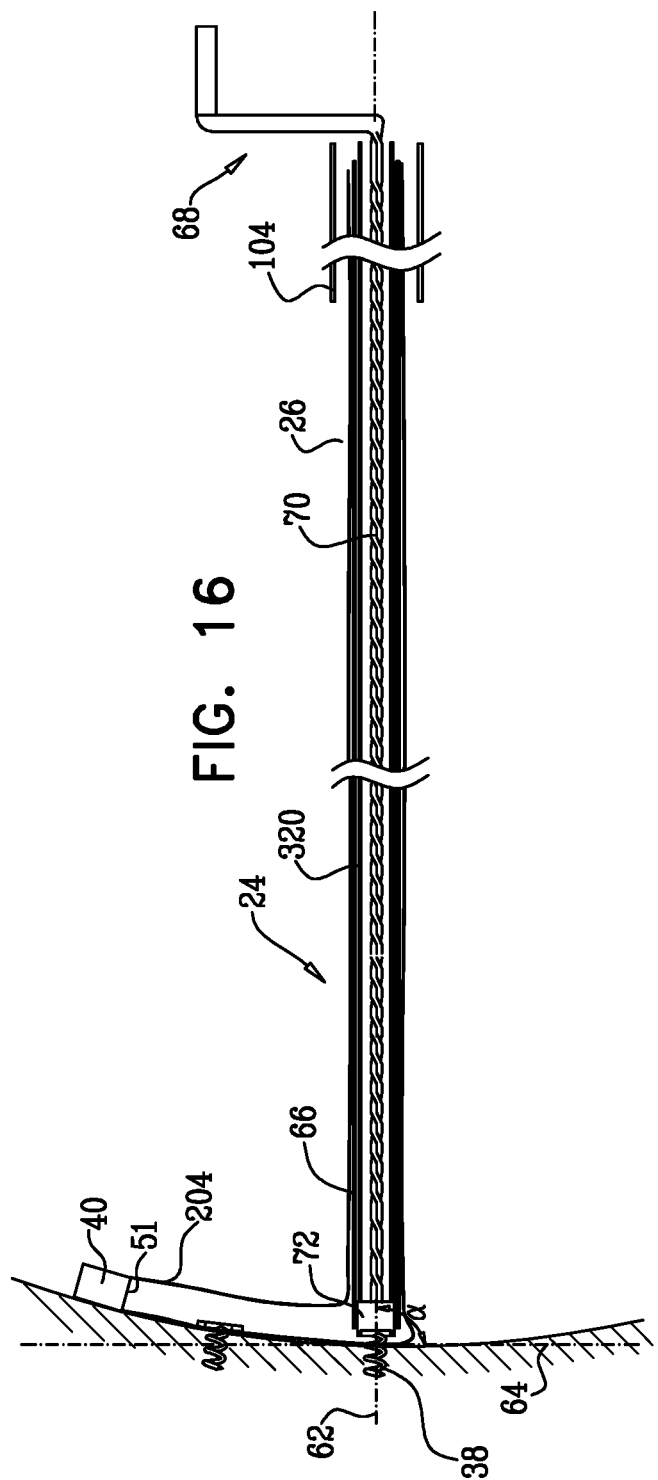

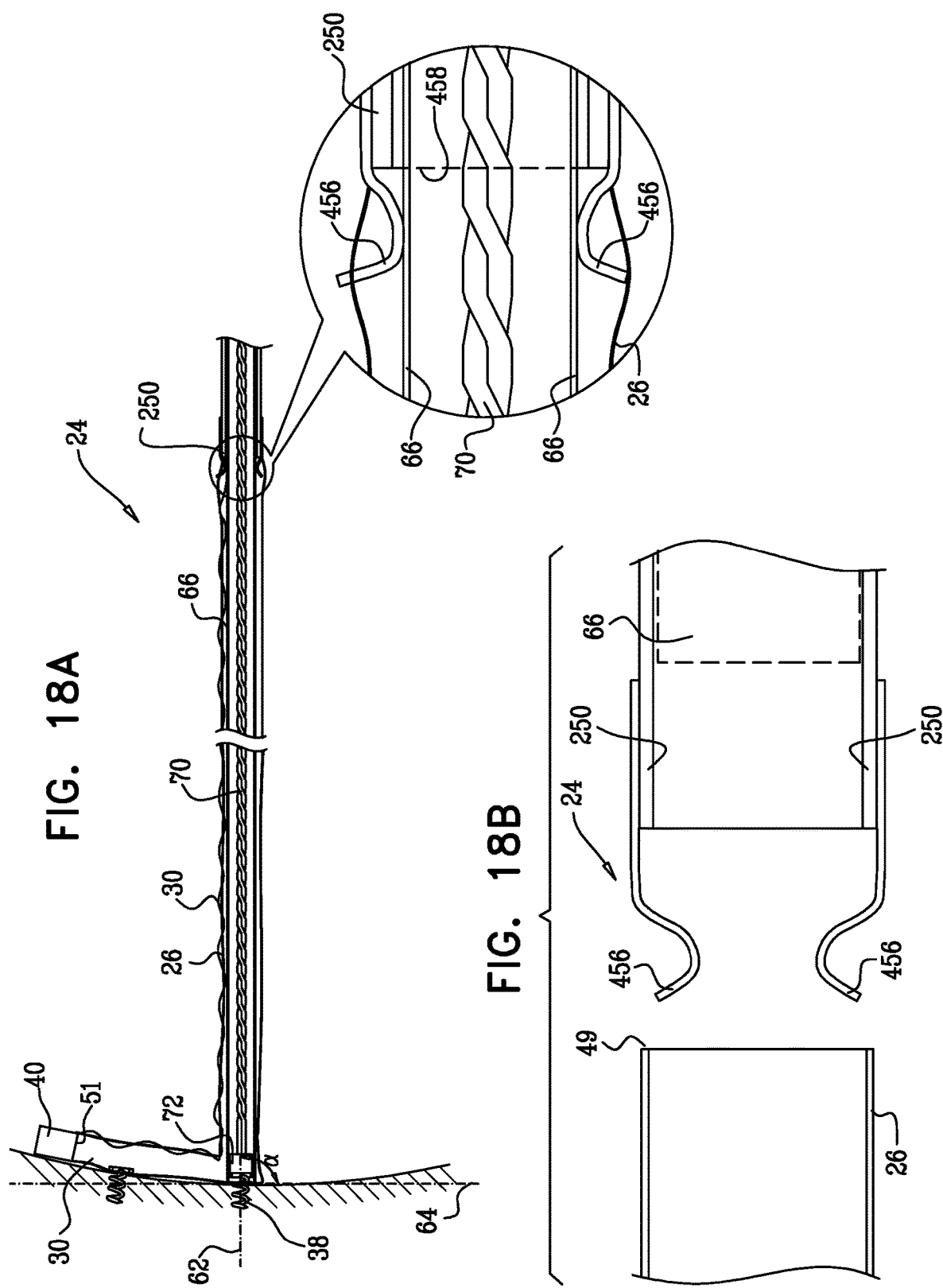

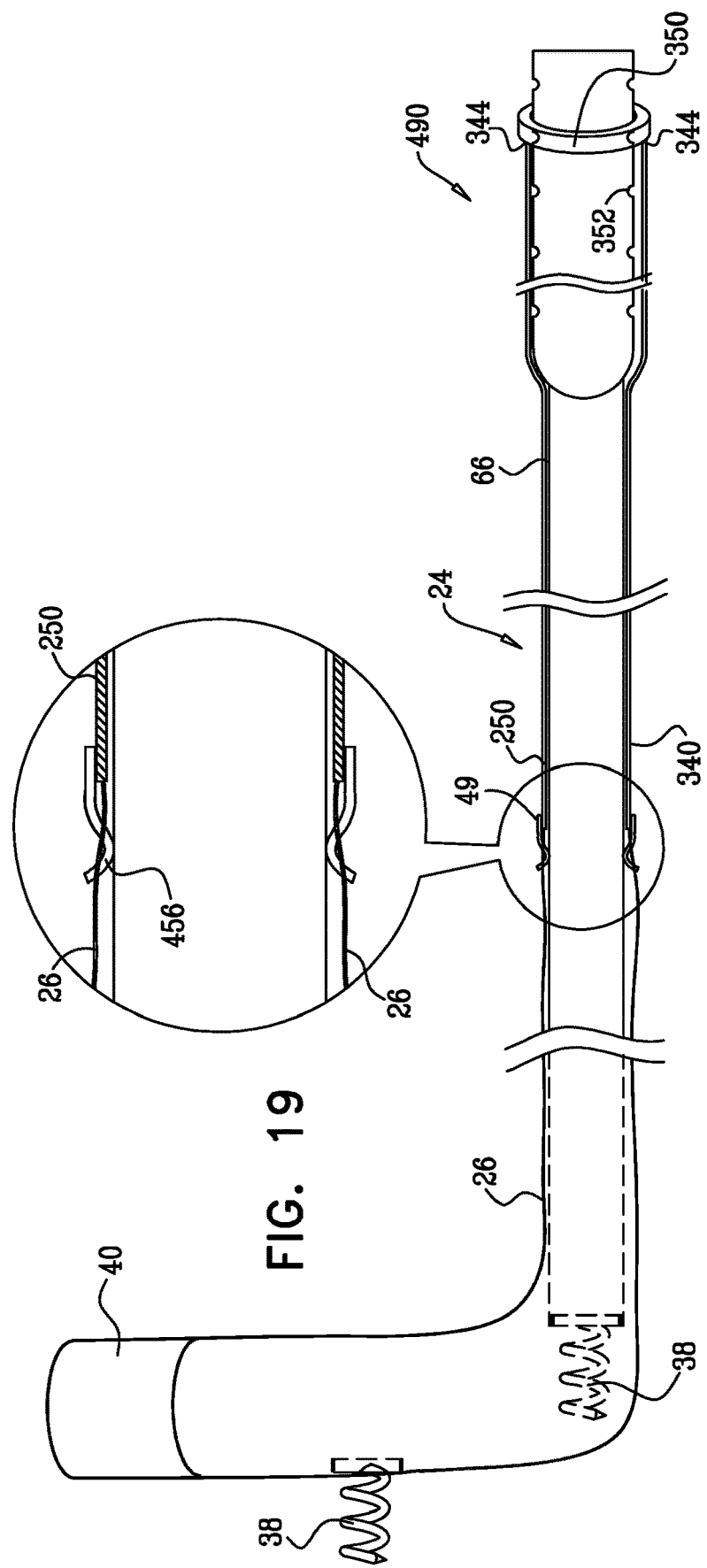

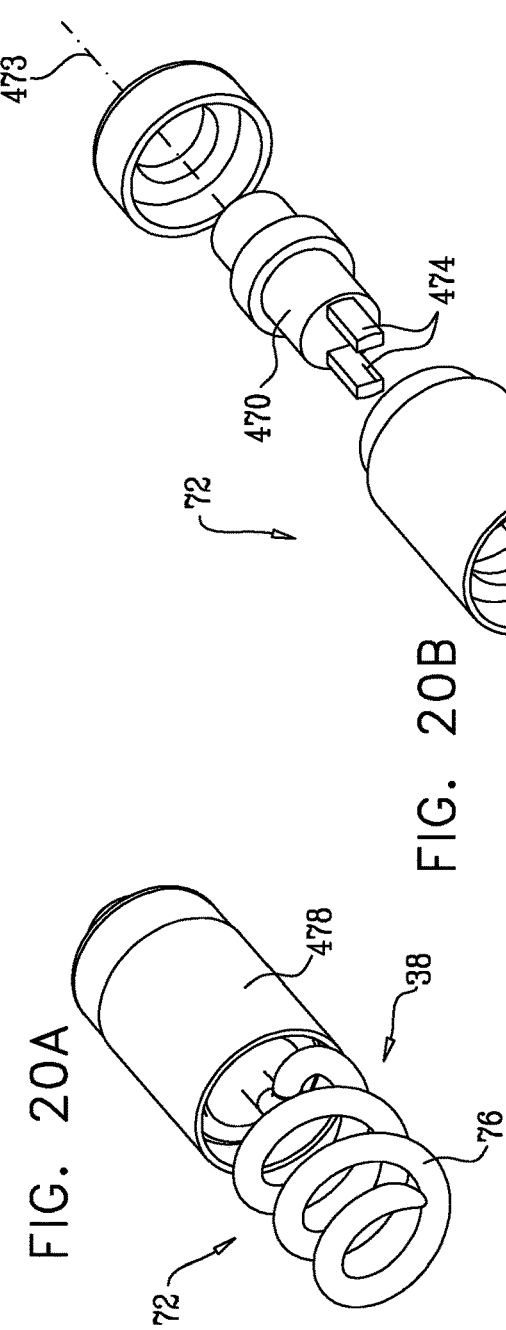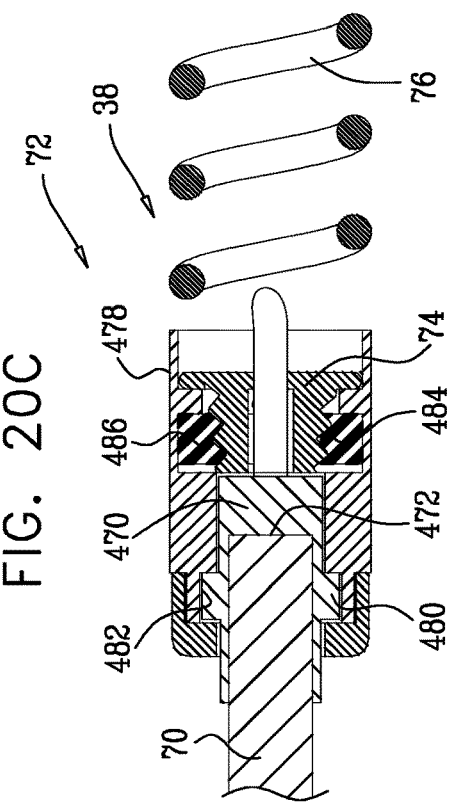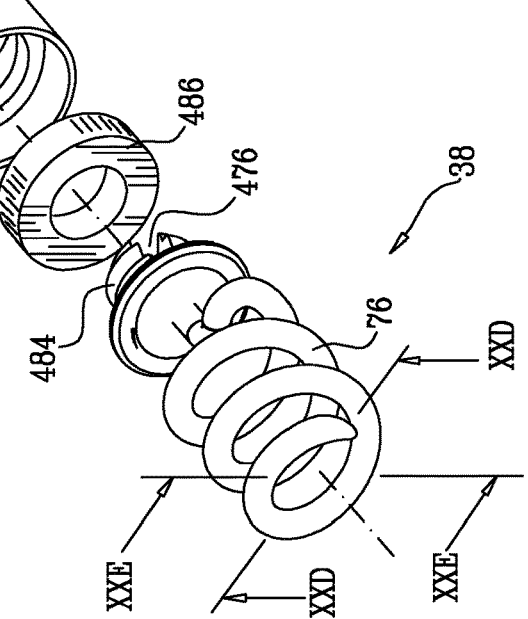

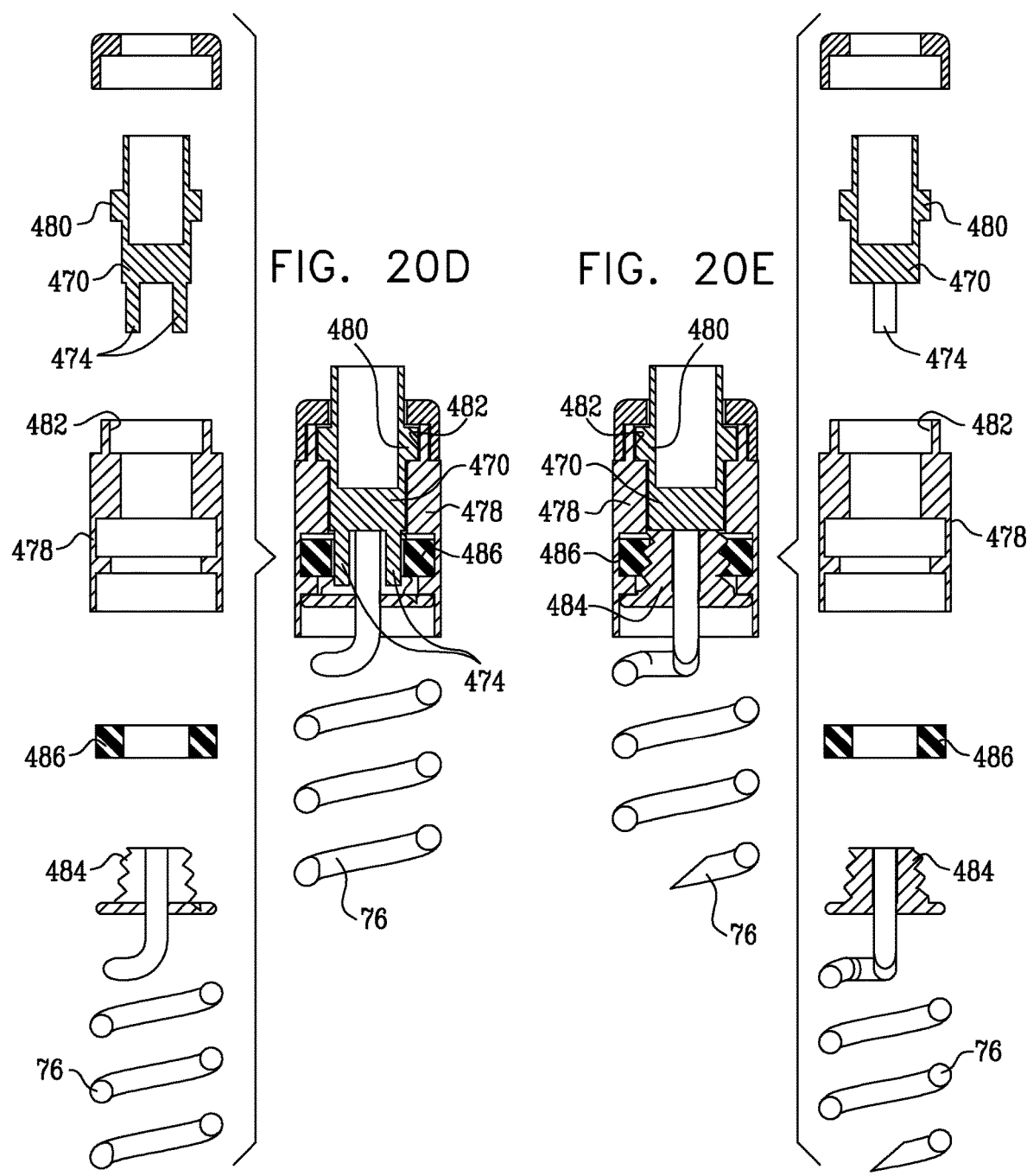

DEPLOYMENT TECHNIQUES FOR ANNULOPLASTY RING AND OVER-WIRE ROTATION TOOL

CROSS-REFERENCE TO RELATED APPLICATIONS

The present application is a continuation of U.S. patent application Ser. No. 13/319,030, filed Dec. 16, 2011, which is the U.S. national stage of International Patent Application PCT/IL2010/000358, filed May 4, 2010, which:

(a) is a continuation-in-part of and claims the priority from U.S. patent application Ser. No. 12/435,291 to Maisano et al., entitled, "Adjustable repair chords and spool mechanism therefor," filed May 4, 2009, now U.S. Pat. No. 8,147,542;

(b) is a continuation-in-part of and claims the priority from U.S. patent application Ser. No. 12/437,103 to Zipory et al., entitled, "Annuloplasty ring with intra-ring anchoring," filed May 7, 2009, now U.S. Pat. No. 8,715,342;

(c) is a continuation-in-part of and claims the priority from U.S. patent application Ser. No. 12/548,991 to Maisano et al., entitled, "Implantation of repair chords in the heart," filed Aug. 27, 2009, now U.S. Pat. No. 8,808,368;

(d) is a continuation-in-part of and claims the priority from U.S. patent application Ser. No. 12/689,635 to Zipory et al., entitled, "Over-wire rotation tool," filed Jan. 19, 2010, now U.S. Pat. No. 8,545,553; and (e) is a continuation-in-part of and claims the priority from U.S. patent Ser. No. 12/689,693 to Hammer et al., entitled, "Deployment techniques for annuloplasty ring," filed Jan. 19, 2010, now U.S. Pat. No. 8,911,494.

All of the above-mentioned applications are assigned to the assignee of the present application and are incorporated herein by reference.

FIELD OF THE APPLICATION

Some applications of the present invention relate in general to valve repair, and more specifically to repair of an atrioventricular valve of a patient.

BACKGROUND OF THE APPLICATION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

US Patent Application Publication 2007/0080188 to Spence et al. describes systems and methods for securing tissue including the annulus of a mitral valve. The systems and methods may employ catheter based techniques and devices to plicate tissue and perform an annuloplasty. Magnets may be used for guidance in deploying fasteners from a catheter. The fasteners are cinched with a flexible tensile member.

U.S. Pat. No. 6,619,291 to Hlavka et al. describes a minimally invasive method of performing annuloplasty. A method for performing a procedure on a mitral valve of a heart includes inserting an implant into a left ventricle and orienting the implant in the left ventricle substantially below the mitral valve. The implant and tissue around the mitral valve are connected and tension is provided to the implant, in one application, in order to substantially reduce an arc length associated with the mitral valve. In another application, the implant is inserted into the left ventricle through the aorta and the aortic valve.

US Patent Application Publication 2006/0241656 to Starksen et al. describes devices, systems and methods for facilitating positioning of a cardiac valve annulus treatment device, thus enhancing treatment of the annulus. Methods generally involve advancing an anchor delivery device through vasculature of the patient to a location in the heart for treating the valve annulus, contacting the anchor delivery device with a length of the valve annulus, delivering a plurality of coupled anchors from the anchor delivery device to secure the anchors to the annulus, and drawing the anchors together to circumferentially tighten the valve annulus. Devices generally include an elongate catheter having at least one tensioning member and at least one tensioning actuator for deforming a distal portion of the catheter to help it conform to a valve annulus. The catheter device may be used to navigate a subannular space below a mitral valve to facilitate positioning of an anchor delivery device.

US Patent Application Publication 2006/0025787 to Morales et al. describes methods and devices that provide constriction of a heart valve annulus to treat cardiac valve regurgitation and other conditions. Applications typically include a device for attaching a cinching or tightening apparatus to a heart valve annulus to reduce the circumference of the annulus, thus reducing valve regurgitation. Tightening devices may include multiple tethered clips, multiple untethered crimping clips, stabilizing devices, visualization devices, and the like. In one application, a plurality of tethered clips is secured circumferentially to a valve annulus, and the tether coupling the clips is cinched to reduce the circumference of at least a portion of the annulus. Methods and devices may be used in open heart surgical procedures, minimally invasive procedures, catheter-based procedures, and/or procedures on beating hearts or stopped hearts.

U.S. Pat. No. 7,431,692 to Zollinger et al. describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

US Patent Application Publication 2007/0016287 to Cartledge et al. describes an implantable device for controlling shape and/or size of an anatomical structure or lumen. The implantable device has an adjustable member configured to adjust the dimensions of the implantable device. The implantable device is housed in a catheter and insertable from a minimally invasive surgical entry. An adjustment tool actuates the adjustable member and provide for adjustment before, during or after the anatomical structure or lumen resumes near normal to normal physiologic function.

US Patent Application Publication 2004/0236419 to Milo describes methods for reconfiguring an atrioventricular heart valve that may use systems comprising a partial or complete annuloplasty rings proportioned to reconfigure a heart valve that has become in some way incompetent, a pair of trigonal sutures or implantable anchors, and a plurality of staples which may have pairs of legs that are sized and shaped for association with the ring at spaced locations along its length. These systems permit relative axial movement between the staples and the ring, whereby a patient's heart valve can be reconfigured in a manner that does not deter subtle shifting of the native valve components. Shape-memory alloy material staples may have legs with free ends that interlock following implantation. Annuloplasty rings may be complete or partial and may be fenestrated. One alternative method routes a flexible wire, preferably of shape-memory material, through the bights of pre-implanted staples. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them and may have a variety of shapes and forms. Various ones of these systems are described as being implanted non-invasively using a delivery catheter.

US Patent Application Publication 2005/0171601 to Cosgrove et al. describes an annuloplasty repair segment and template for heart valve annulus repair. The elongate flexible template may form a distal part of a holder that also has a proximal handle. Alternatively, the template may be releasably attached to a mandrel that slides within a delivery sheath, the template being released from the end of the sheath to enable manipulation by a surgeon. A tether connecting the template and mandrel may also be provided. The template may be elastic, temperature responsive, or multiple linked segments. The template may be aligned with the handle and form a two- or three-dimensional curve out of alignment with the handle such that the annuloplasty repair segment attached thereto conforms to the curve. The template may be actively or passively converted between its straight and curved positions. The combined holder and ring is especially suited for minimally-invasive surgeries in which the combination is delivered to an implantation site through a small access incision with or without a cannula, or through a catheter passed though the patient's vasculature.

The following patents and patent application publications may be of interest:

U.S. Pat. No. 5,306,296 to Wright et al.
U.S. Pat. No. 5,674,279 to Wright et al.
U.S. Pat. No. 5,961,539 to Northrup, I I I et al.
U.S. Pat. No. 6,524,338 to Gundry
U.S. Pat. No. 6,569,198 to Wilson et al.
U.S. Pat. No. 6,602,288 to Cosgrove et al.
U.S. Pat. No. 6,602,289 to Colvin et al.
U.S. Pat. No. 6,689,164 to Seguin
U.S. Pat. No. 6,702,826 to Liddicoat et al.
U.S. Pat. No. 6,718,985 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
U.S. Pat. No. 7,186,262 to Saadat
US Patent Application Publication 2002/0087048 to Brock et al.
US Patent Application Publication 2002/0173841 to Ortiz et al.
US Patent Application Publication 2003/0050693 to Quijano et al.
US Patent Application Publication 2003/0167062 to Gambale et al.
US Patent Application Publication 2004/0024451 to Johnson et al.
US Patent Application Publication 2004/0122514 to Fogarty et al.
US Patent Application Publication 2004/0148021 to Cartledge et al.
US Patent Application Publication 2005/0055087 to Starksen
US Patent Application Publication 2005/0288781 to Moaddeb et al.
US Patent Application Publication 2006/0069429 to Spence et al.
US Patent Application Publication 2007/0051377 to Douk et al.
US Patent Application Publication 2007/0055206 to To et al.
US Patent Application Publication 2007/0162111 to Fukamachi et al.
US Patent Application Publication 2007/0255400 to Parravicini et al.
US Patent Application Publication 2008/0004697 to Lichtenstein et al.
PCT Publication WO 01/26586 to Seguin
PCT Publication WO 02/085251 to Hlavka et al.
PCT Publication WO 02/085252 to Hlavka et al.
PCT Publication WO 06/097931 to Gross et al.
PCT Publication WO 07/136783 to Cartledge et al.
PCT Publication WO 08/068756 to Gross et al.

The following articles may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

SUMMARY

In some applications of the present invention, an implant structure is provided that comprises a contracting mechanism. The contracting mechanism comprises a rotatable structure, arranged such that rotation of the rotatable structure contracts the implant structure. The implant further comprises a longitudinal member, such as a wire, which is coupled to the contracting mechanism. A rotation tool is provided for rotating the rotatable structure. The tool is configured to be guided along (e.g., over, alongside, or through) the longitudinal member, to engage the rotatable structure, and to rotate the rotatable structure in response to a rotational force applied to the tool.

In some applications of the present invention, the implant structure comprises an adjustable partial annuloplasty ring for repairing a dilated valve annulus of an atrioventricular valve, such as a mitral valve. The annuloplasty ring comprises a flexible sleeve and a plurality of anchors. An anchor deployment manipulator is advanced into a lumen of the sleeve, and, from within the lumen, deploys the anchors through a wall of the sleeve and into cardiac tissue, thereby anchoring the sleeve around a portion of the valve annulus.

For some applications of the present invention, the anchors are deployed from a distal end of the manipulator while the distal end is positioned such that a central longitudinal axis through the distal end of the manipulator forms an angle with a surface of the cardiac tissue of between about 45 and 90 degrees, e.g., between about 75 and 90 degrees, such as about 90 degrees. Typically, the anchors are deployed from the distal end of the manipulator into the cardiac tissue in a direction parallel to the central longitudinal axis through the distal end of the manipulator.

In some applications of the present invention, the anchors are deployed from the left atrium into the upper region of the ventricular wall near the atrium, tissue of which generally provides more secure anchoring than does the atrial wall. The above-mentioned angle of deployment enables such deployment into the upper region of the ventricular wall.

In some applications of the present invention, the anchor deployment manipulator comprises a steerable outer tube in which is positioned an anchor driver having an elongated, flexible shaft. Rotation of the anchor driver screws the anchors into the cardiac tissue. The anchors may, for example, be helical in shape.

For some applications, the plurality of anchors are applied using the manipulator by loading a first one of the anchors onto the anchor driver, and deploying the anchor into the cardiac tissue. The anchor driver is withdrawn from the body of the subject, and a second one of the anchors is loaded onto the anchor driver. The anchor driver is reintroduced into the sleeve of the annuloplasty ring, and the second anchor is deployed. These steps are repeated until all of the anchors have been deployed. Alternatively, the anchor driver is configured to simultaneously hold a plurality of anchors, and to deploy them one at a time.

Typically, the manipulator is gradually withdrawn in a proximal direction during the anchoring procedure as anchors are deployed. The first anchor is thus deployed most distally in the sleeve (generally at or within a few millimeters of the distal tip of the sleeve), and each subsequent anchor is deployed more proximally.

For some applications, the annuloplasty ring is typically configured to be placed only partially around the valve annulus (e.g., to assume a C-shape), and, once anchored in place, to be contracted so as to circumferentially tighten the valve annulus. To this end, the annuloplasty ring may comprise a flexible contracting member such as a wire, which is typically positioned within the lumen of the sleeve.

For some applications, the contracting mechanism comprises a spool to which a first end of the contracting member is coupled. The spool is positioned in a vicinity of either the proximal or the distal end of the sleeve, or the spool is positioned at any suitable location between the proximal and distal ends of the sleeve. A second end of the contracting member is coupled to the sleeve in a vicinity of the end of the sleeve opposite the end to which the spool is positioned. Rotation of the spool winds a portion of the contracting member around the spool, thereby contracting the implant structure. For some applications, the contracting mechanism comprises a housing that houses the spool, and the rotation tool is configured to engage and rotate the spool with respect to the housing. For some applications, the rotation tool comprises a tube, which is configured to be passed over the longitudinal member coupled to the contracting mechanism, and to engage the housing, such that the housing is held rotationally stationary when the tube is held rotationally stationary.

For some applications, the longitudinal member is removably coupled to the contracting mechanism, e.g., to the rotatable structure of the contracting mechanism. For example, a distal portion of the longitudinal member may be shaped so as to define a screw thread, and the contracting mechanism may shaped so as to define a threaded opening, into which the distal portion of the longitudinal member is screwed so as to removably coupled the longitudinal member to the contracting mechanism.

For some applications, the rotation tool comprises a first tube, which is configured to pass over the longitudinal member. Rotation of the tube decouples the longitudinal member from the contracting mechanism. For some applications, the rotation tool further comprises a second tube, which is configured to pass over the first tube. The second tube engages the rotatable structure, such that rotation of the second tube rotates the rotatable structure.

In some applications of the present invention, a rotation handle is provided. A longitudinal member, such as the proximal end of the longitudinal member coupled to the contracting mechanism, is passed at least partially through the rotation handle. The rotation handle comprises (a) a first-tube rotation knob, which is coupled to the first tube, such that rotation of the first-tube rotation knob rotates the first tube, (b) a second-tube rotation knob, which is coupled to the second tube, such that rotation of the second-tube rotation knob rotates the second tube, and (c) a control knob. When in a first position, the control knob engages both first-tube and second-tube rotation knobs. When in a second position, the control knob engages the second-tube rotation knob but not the first-tube rotation knob. For some applications, when in the first position, the control knob at least partially (typically entirely) covers the first-tube tube rotation knob, thereby preventing access to the knob by the surgeon. When in the second position, the control knob reveals (i.e., no longer covers) the first-tube tube rotation knob. The surgeon thus has convenient access to the exposed knob.

For some application in which the implant structure comprises an annuloplasty ring, all of the tools and elements of the annuloplasty system that are introduced into left atrium are contained within the sleeve of the annuloplasty ring, which reduces the risk that any elements of the system will accidentally be released to the blood circulation, or damage surrounding tissue. In addition, the lumen of the sleeve provides guidance if it should be necessary to return to a previously deployed anchor, such as to tighten, loosen, remove, or relocate the anchor. For some applications, the anchors comprise helical screws, which facilitate such adjusting or removing.

The annuloplasty ring may be advanced toward the annulus of a valve in any suitable procedure, e.g., a transcatheter procedure, a percutaneous procedure, a minimally invasive procedure, or an open heart procedure.

There is therefore provided, in accordance with an application of the present invention, apparatus including:

an implant structure, which includes a contracting mechanism, which includes a rotatable structure, arranged such that rotation of the rotatable structure contracts the implant structure;

a longitudinal member, which is coupled to the contracting mechanism; and a tool for rotating the rotatable structure, the tool configured to be guided along the longitudinal member, to engage the rotatable structure, and to rotate the rotatable structure in response to a rotational force applied to the tool.

For some applications, the longitudinal member includes at least one wire, and the tool is configured to be guided over the wire. For other applications, the longitudinal member includes a tube, and the tool is configured to be guided through the tube.

For some applications, the implant structure includes an annuloplasty ring. Alternatively, the implant structure includes at least one repair chord, which is configured to pull two portions of heart tissue toward each other upon contraction of the implant structure.

For some applications, the implant structure includes one or more tissue anchors.

For some applications, a portion of the implant structure is shaped so as to define a rack, a portion of the rotatable structure is shaped so as to define a pinion that mates with the rack, and the implant structure is configured such that rotation of the rotatable structure causes the portion of the implant structure to move with respect to the rotatable structure.

For some applications, the implant structure includes a flexible contracting member that is coupled to the rotatable structure, and arranged such that rotation of the rotatable structure tightens the flexible contracting member, thereby contracting the implant structure.

For some applications, the rotatable structure includes a spool, the implant structure is coupled to the spool, and arranged such that rotation of the spool winds a portion of the implant structure around the spool, and the tool is configured to engage and rotate the spool. For some applications, the implant structure includes a flexible contracting member that is coupled to the spool, the portion of the implant structure includes a portion of the contracting member, and the contracting member is arranged such that rotation of the spool winds the portion of the contracting member around the spool.

For some applications, the contracting mechanism includes a housing that houses the spool, and the tool is configured to engage and rotate the spool with respect to the housing. For some applications, the tool includes a tube, which is configured to be passed over the longitudinal member and to engage the housing, such that the housing is held rotationally stationary when the tube is held rotationally stationary.

For some applications, the longitudinal member is removably coupled to the contracting mechanism. For some applications, a distal portion of the longitudinal member is shaped so as to define a screw thread, and the contracting mechanism is shaped so as to define a threaded opening, into which the distal portion of the longitudinal member is screwed so as to removably coupled the longitudinal member to the contracting mechanism. For some applications, the longitudinal member is removably coupled to the rotatable structure of the contracting mechanism. For some applications, the tool includes a tube, which is configured to pass over the longitudinal member, and which is configured such that rotation of the tube decouples the longitudinal member from the contracting mechanism.

For some applications, the tube is a first tube, the tool further includes a second tube, the first tube is positioned within the second tube, and the second tube is configured to engage the rotatable structure, such that rotation of the second tube rotates the rotatable structure. For some applications, the apparatus further includes a rotation handle, through which a proximal end of the longitudinal member at least partially passes, and which includes: a first-tube rotation knob, which is coupled to the first tube, such that rotation of the first-tube rotation knob rotates the first tube; a second-tube rotation knob, which is coupled to the second tube, such that rotation of the second-tube rotation knob rotates the second tube; and a control knob, which, when in a first position, engages both first-tube and second-tube rotation knobs, and when in a second position, engages the second-tube rotation knob but not the first-tube rotation knob. For some applications, the rotation handle includes a handle housing, and the control knob, when in the second position, engages the handle housing, thereby rotationally fixing the control knob to the handle housing.

For some applications, the tool further includes a third tube, the first and second tubes are positioned within the third tube, the rotatable structure includes a spool, the contracting mechanism includes a housing that houses the spool, the implant structure is coupled to the spool, and arranged such that rotation of the spool winds a portion of the implant structure around the spool, and the second tube is configured to engage and rotate the spool with respect to the housing, and the third tube is configured to engage the housing, such that the housing is held rotationally stationary when the third tube is held rotationally stationary.

For some applications, the contracting mechanism includes a locking mechanism, the longitudinal member is shaped so as to define a distal force applicator, which is configured to unlock the locking mechanism when the longitudinal member is coupled to the contracting mechanism, thereby allowing the spool to rotate with respect to the housing.

There is further provided, in accordance with an application of the present invention, apparatus including:
  a longitudinal member;
  a first tube, which passes over the longitudinal member;
  a second tube, which passes over the first tube; and
  a rotation handle, through which the longitudinal member at least partially passes, and which includes:
    a first-tube rotation knob, which is coupled to the first tube, such that rotation of the first-tube rotation knob rotates the first tube;
    a second-tube rotation knob, which is coupled to the second tube, such that rotation of the second-tube rotation knob rotates the second tube; and
    a control knob, which:
      when in a first position, engages both the first-tube and second-tube rotation knobs, and
      when in a second position, engages the second-tube rotation knob but not the first-tube rotation knob.

For some applications, the longitudinal member includes at least one wire.

For some applications, the rotation handle is configured such that the rotation of the control knob, (a) when in the first position, rotates both the first-tube and second-tube rotation knobs, and (b) when in the second position, rotates the second-tube rotation knob but not the first-tube rotation knob.

For some applications, the rotation handle is configured such that the control knob, (a) when in the first position, at least partially covers the first-tube rotation knob, thereby preventing access to the first-tube rotation knob, and (b) when in the second position, reveals the first-tube rotation knob, thereby allowing access to the first-tube rotation knob. For some applications, the control knob is configured to slide between the first and second positions.

For some applications, the control knob is configured such that a transition between the first and second positions is not effected by rotation of the control knob.

For some applications, the control knob is configured to slide between the first and second positions. For some applications, the control knob is configured such that when in the first position, an inner surface of the control knob engages the first-tube rotation knob and the second-tube rotation knob. For some applications, the rotation handle includes a handle housing, and the sliding control knob, when in the second position, engages the handle housing, thereby rotationally fixing the control knob to the handle housing. For some applications, the control knob is configured that when in the second position, an outer surface of the control knob engages the handle housing.

For some applications, the apparatus further includes a third tube, which passes over the second tube, and which is coupled to the rotation handle such that the third tube cannot rotate with respect to the rotation handle.

For some applications, the first and second tubes extend from a distal end of the rotation handle, and the rotation handle includes one or more springs which are configured to push at least one of the first and second tubes in a distal direction. For some applications, the rotation handle includes a spring locking mechanism, which is configured to assume locking and released states, and, when in the locking state, to prevent at least one of the springs from pushing on at least one of the first and second tubes in the distal direction.

For some applications, the longitudinal member is longitudinally fixed to the rotation handle, but is allowed to rotate with respect to the rotation handle. For some applications, the first and second tubes extend from a distal end of the rotation handle, and the rotation handle includes a lever that is configured to allow the longitudinal member to be advanced toward a proximal end of the rotation handle, while preventing withdrawal of the longitudinal member toward the distal end of the rotation handle.

For some applications, the apparatus further includes an implant structure, which includes a contracting mechanism, which includes a rotatable structure, arranged such that rotation of the rotatable structure contracts the implant structure, the longitudinal member is removably coupled to the contracting mechanism, the first tube is configured such that rotation of the tube decouples the longitudinal member from the contracting mechanism, and the second tube is configured to engage the rotatable structure, such that rotation of the second tube rotates the rotatable structure.

There is still further provided, in accordance with an application of the present invention, apparatus including:
a sleeve having a lumen;
a deployment manipulator tube, which is configured to be removably positioned partially within the lumen of the sleeve, such that the deployment manipulator tube extends out of a proximal end of the sleeve; and
a pusher tube, which is configured to pass over a portion of the deployment manipulator tube, such that a distal end of the pusher tube is in contact with the proximal end of the sleeve.

For some applications, the apparatus further includes an annuloplasty ring, which includes the sleeve. For some applications, the annuloplasty ring further includes at least one tissue anchor. For some applications, the annuloplasty ring includes a partial annuloplasty ring.

For some applications, the distal end of the pusher tube is removably coupled to the proximal end of the sleeve. For some applications, the pusher tube includes one or more coupling elements, which are configured to removably couple the distal end of the pusher tube to the proximal end of the sleeve. For some applications, the apparatus is configured such that (a) when the deployment manipulator tube is positioned within the lumen of the sleeve, the deployment manipulator tube causes the coupling elements to engage the sleeve, thereby removably coupling the distal end of the pusher tube to the proximal end of the sleeve, and (b) when the deployment manipulator tube is withdrawn from the sleeve, the coupling elements disengage from the sleeve, thereby decoupling the distal end of the pusher tube from the proximal end of the sleeve. For some applications, the coupling elements are configured to have a natural tendency to flex inwards toward a central longitudinal axis of the sleeve that passes through the proximal end of the sleeve, and the deployment manipulator tube, when positioned within the lumen of the sleeve, pushes the coupling elements outwards away from the longitudinal axis, thereby causing the coupling elements to engage the sleeve.

For some applications, the apparatus further includes an external control handle, which is coupled to a proximal portion of the deployment manipulator tube and to a proximal end of the pusher tube, and which is configured to controllably release the pusher tube in a distal direction as the sleeve is withdrawn from the deployment manipulator tube. For some applications, the external control handle is configured to controllably release the pusher tube incrementally in the distal direction by one or more set distances.

For some applications, the annuloplasty system further includes: at least one tissue anchor; and an anchor deployment manipulator, which includes: the deployment manipulator tube; and an anchor driver, which is configured to be at least partially positioned within the deployment manipulator tube, and, while so positioned, to deploy the at least one anchor through a wall of the sleeve.

There is additionally provided, in accordance with an application of the present invention, apparatus for use with tissue of a subject, the apparatus including:
an anchor driver, which includes a driver head, which is shaped so as to define one or more mechanical coupling elements, and which includes a flexible ring; and
an anchor, which includes:
a coupling head, which is shaped so as to define: (a) one or more mating elements corresponding to the mechanical coupling elements, and configured to engage the mechanical coupling elements such that rotation of the mechanical coupling elements rotates the mating elements, which in turn rotate the coupling head, and (b) an outer coupling surface, sized to be inserted into and engage the flexible ring; and
a tissue coupling element, which is fixed to the coupling head,
wherein the rotation of the mechanical coupling elements causes the tissue coupling element of the anchor to screw itself into the tissue, thereby causing separation of: (a) the outer coupling surface of the coupling head from the flexible ring, and (b) the mating elements of the coupling head from the corresponding mechanical coupling elements.

For some applications, the driver head includes: an inner mating component, which is shaped so as to define the one or more mechanical coupling elements; and an outer element, which at least partially surrounds the inner mating component and extends in a distal direction beyond a distal end of the inner mating component, and the flexible ring is coupled to an inner surface of the outer element. For some applications, the outer element is configured to rotate freely with respect to the inner mating component.

For some applications, the coupling surface of the coupling head is shaped so as to define a screw thread, such that rotation of the mechanical coupling elements causes the outer coupling surface to unscrew from the flexible ring.

For some applications, the mechanical coupling elements of the driver head include protrusions, and the mating elements of the coupling head include slots.

For some applications, the anchor driver further includes a shaft, and the driver head is coupled to a distal end of the shaft. For some applications, the inner mating component is coupled to the distal end of the shaft such that the inner mating component is rotationally fixed to the shaft.

For some applications, the apparatus further includes an annuloplasty ring, which includes a sleeve having a lumen, and the anchor driver is configured to be removably positioned within the lumen of the sleeve.

For some applications, the coupling element is shaped so as to define a shape selected from the group consisting of: a helix, a spiral, and a screw shaft.

There is yet additionally provided, in accordance with an application of the present invention, a method including:

placing, into a body of a subject, an implant structure, which includes a contracting mechanism that includes a rotatable structure, such that a longitudinal member coupled to the contracting mechanism extends outside of the body;

guiding a tool along the longitudinal member to the rotatable subject;

engaging the rotatable structure with the tool; and contracting the implant structure by rotating the rotatable structure using the tool.

For some applications, the longitudinal member includes at least one wire, and guiding the tool includes guiding the tool over the wire.

For some applications, the longitudinal includes at least one tube, and guiding the tool includes guiding the tool through the tube.

For some applications, placing the implant structure includes placing an annuloplasty ring into an atrium of the body in a vicinity of an annulus of an atrioventricular valve.

For some applications, placing the implant structure includes placing at least one repair chord into a ventricle of the body such that, upon contracting of the implant structure, the repair chord pulls two portions of heart tissue toward each other.

For some applications, a portion of the implant structure is shaped so as to define a rack, a portion of the rotatable structure is shaped so as to define a pinion that mates with the rack, and contracting the implant structure includes moving the portion of the implant structure with respect to the rotatable structure by rotating the rotatable structure using the tool.

For some applications, the implant structure includes a flexible contracting member that is coupled to the rotatable structure, and contracting the implant structure includes tightening the flexible contracting member by rotating the rotatable structure using the tool.

For some applications, the rotatable structure includes a spool, the implant structure is coupled to the spool, engaging includes engaging the spool with the tool, and contracting the implant structure includes winding a portion of the implant structure around the spool by rotating the spool using the tool. For some applications, the implant structure includes a flexible contracting member that is coupled to the spool, the portion of the implant structure includes a portion of the contracting member, and winding includes winding the portion of the contracting member around the spool by rotating the spool using the tool.

For some applications, the contracting mechanism including a housing that houses the spool, and winding includes rotating the spool with respect to the housing. For some applications, the tool includes a tube, and guiding the tool over the longitudinal member includes passing the tube over the longitudinal member and engaging the housing with the tube such that the housing is held rotationally stationary when the tube is held rotationally stationary.

For some applications, the method further includes decoupling the longitudinal member from the contracting mechanism after rotating the rotatable structure. For some applications, a distal portion of the longitudinal member is shaped so as to define a screw thread, the contracting mechanism is shaped so as to define a threaded opening, into which the distal portion of the longitudinal member is initially screwed, and decoupling includes unscrewing the longitudinal member from the threaded opening. For some applications, the longitudinal member is removably coupled to the rotatable structure of the contracting mechanism, and decoupling includes decoupling the longitudinal member from the rotatable structure.

For some applications, the tool includes a tube, guiding the tool over the longitudinal member includes passing the tube over the longitudinal member, and decoupling the longitudinal member from the contracting mechanism includes rotating the tube. For some applications, the tube is a first tube, rotating the tube includes rotating the first tube, the tool further includes a second tube, the first tube is positioned within the second tube, engaging includes engaging the rotatable structure with the second tube, and contracting the implant structure includes rotating the rotatable structure by rotating the second tube. For some applications, the method further includes passing a proximal end of the longitudinal member at least partially through a rotation handle, which includes a first-tube rotation knob coupled to the first tube, a second tube-rotation knob coupled to the second tube, and a control knob, which (a) when in a first position, engages both the first-tube and second-tube rotation knobs, and (b) when in a second position, engages the second-tube rotation knob but not the first-tube rotation knob, and engages a housing of the handle, thereby rotationally fixing the control knob to the handle housing, contracting the implant structure includes rotating the first and second tubes by rotating the control knob when in the first position, and decoupling the longitudinal member from the contracting mechanism includes moving the control knob into the second position, and subsequently rotating the first tube by rotating the first-tube rotation knob.

For some applications, the tool further includes a third tube, the first and second tubes are positioned within the third tube, the rotatable structure includes a spool, the contracting mechanism includes a housing that houses the spool, the implant structure is coupled to the spool, and contracting the implant includes: rotating a portion of the implant structure around the spool by rotating the spool with respect to the housing by rotating the second tube; engaging the housing with the third tube; and holding the housing rotationally stationary by holding the third tube rotationally stationary.

For some applications, the contracting mechanism includes a locking mechanism, and the longitudinal member is shaped so as to define a distal force applicator, which is configured to unlock the locking mechanism when the longitudinal member is coupled to the contracting mechanism, thereby allowing the spool to rotate with respect to the housing.

There is also provided, in accordance with an application of the present invention, a method including:

passing a longitudinal member at least partially through a rotation handle, which includes (a) a first-tube rotation knob, which is coupled to a first tube that passes over the longitudinal member, (b) a second-tube rotation knob, which is coupled to a second tube that passes over the first tube, and (c) a control knob, which (i) when in a first position, engages both the first-tube and second-tube rotation knobs, and (ii) when in a second position, engages the second-tube rotation knob but not the first-tube rotation knob, and engages a housing of the handle, thereby rotationally fixing the control knob to the handle housing;

rotating the first and second tubes by rotating the control knob when in the first position; and moving the control knob into the second position, and subsequently rotating the first tube by rotating the first-tube rotation knob.

For some applications, the longitudinal includes at least one wire, and passing includes passing the wire at least partially through the rotation handle.

For some applications, moving the control knob into the second position does not include rotating the control knob.

For some applications, moving the control knob into the second position includes sliding the control knob into the second position.

For some applications, passing the longitudinal member at least partially through the rotation handle includes longitudinally fixing the longitudinal member to the rotation handle such that the longitudinal member is allowed to rotate with respect to the rotation handle.

For some applications, the method further includes:

placing, into a body of a subject, an implant structure, which includes a contracting mechanism that includes a rotatable structure, arranged such that rotation of the rotatable structure contracts the implant structure, wherein the longitudinal member is removably coupled to the contracting mechanism;

engaging the rotatable structure with the second tube such that rotation of the second tube rotates the rotatable structure; and engaging the longitudinal member with the first tube, such that rotation of the first tube decouples the longitudinal member from the contracting mechanism.

There is further provided, in accordance with an application of the present invention, a method including:

removably positioning a deployment manipulator tube partially within a lumen of a sleeve of an annuloplasty ring, such that the deployment manipulator tube extends out of a proximal end of the sleeve; and placing a pusher tube over the deployment manipulator tube such that a distal end of the pusher tube is in contact with the proximal end of the sleeve.

For some applications, the method further includes withdrawing the sleeve from the deployment manipulator tube in a distal direction, and, while withdrawing, pushing the pusher tube against the proximal end of the sleeve. For some applications, withdrawing the sleeve includes, while withdrawing the sleeve, controllably releasing the pusher tube in the distal direction, using an external control handle to which is coupled a proximal portion of the deployment manipulator tube and a proximal end of the pusher tube. For some applications, controllably releasing includes controllably releasing the pusher tube incrementally in the distal direction by one or more set distances.

For some applications, placing includes removably coupling the distal end of the pusher tube to the proximal end of the sleeve. For some applications, removably coupling includes using one or more one or more coupling elements of the pusher tube to removably couple the distal end of the pusher tube to the proximal end of the sleeve. For some applications, removably coupling includes positioning the deployment manipulator tube within the lumen of the sleeve such that the deployment manipulator tube causes the coupling elements to engage the sleeve, and the method further includes decoupling the distal end of the pusher tube from the proximal end of the sleeve by withdrawing the deployment manipulator tube from the sleeve such that the coupling elements disengage from the sleeve. For some applications, the coupling elements are configured to have a natural tendency to flex inwards toward a central longitudinal axis of the sleeve that passes through the proximal end of the sleeve, and the deployment manipulator tube, when positioned within the lumen of the sleeve, pushes the coupling elements outwards away from the longitudinal axis, thereby causing the coupling elements to engage the sleeve.

For some applications, the method further includes deploying at least one anchor through a wall of the sleeve using an anchor driver that is at least partially positioned within the deployment manipulator tube.

For some applications, the annuloplasty ring is a partial annuloplasty ring, and removably positioning includes removably positioning the deployment manipulator tube partially within the lumen of the partial annuloplasty ring.

There is still further provided, in accordance with an application of the present invention, a method including:

advancing, into a body of a subject, (a) an anchor driver, which includes a driver head, which is shaped so as to define one or more mechanical coupling elements, and which includes a flexible ring, and (b) an anchor, which includes (i) a coupling head, which is shaped so as to define: (A) one or more mating elements corresponding to the mechanical coupling elements, and configured to engage the mechanical coupling elements such that rotation of the mechanical coupling elements rotates the mating elements, which in turn rotate the coupling head, and (B) an outer coupling surface, sized to be inserted into and engage the flexible ring, and (ii) a tissue coupling element, which is fixed to the coupling head; and rotating the mechanical coupling elements to cause the tissue coupling element of the anchor to screw itself into tissue of the body, thereby causing separation of: (a) the outer coupling surface of the coupling head from the flexible ring, and (b) the mating elements of the coupling head from the corresponding mechanical coupling elements.

For some applications, the outer element is configured to rotate freely with respect to the inner mating component.

For some applications, the coupling surface of the coupling head is shaped so as to define a screw thread, such that rotating the mechanical coupling elements causes the outer coupling surface to unscrew from the flexible ring.

For some applications, the mechanical coupling elements of the driver head include protrusions, and the mating elements of the coupling head include slots.

For some applications, advancing the anchor driver includes removably positioning the anchor driver within a lumen of a sleeve of an annuloplasty ring.

For some applications, the coupling element is shaped so as to define a shape selected from the group consisting of: a helix, a spiral, and a screw shaft.

There is further provided, in accordance with an embodiment of the present invention, a method including:

positioning an anchor deployment manipulator at least partially within a lumen of a sleeve of an annuloplasty ring;

placing, into an atrium of a subject in a vicinity of an annulus of an atrioventricular valve, at least a portion of the sleeve that contains a distal end of the deployment manipulator; and deploying at least one anchor from the distal end of the deployment manipulator through a wall of the sleeve such that a coupling element of the anchor enters cardiac tissue of the subject in a direction parallel to a central longitudinal axis of the deployment manipulator through the distal end of the deployment manipulator.

In an embodiment, deploying includes deploying the at least one anchor from the distal end of the deployment manipulator through the wall of the sleeve into the cardiac tissue, while the distal end of the deployment manipulator is positioned such that the central longitudinal axis of the deployment manipulator through the distal end of the deployment manipulator forms an angle of between 45 and 90 degrees with the wall of the sleeve at a point at which the anchor penetrates the wall. For some applications, the point on the wall is a first point on the wall, and the angle is a first angle, the at least one anchor is a first anchor of a plurality of anchors that also includes a second anchor most recently deployed before the first anchor through a second point on the wall, and deploying the first anchor includes deploying the first anchor while the distal end of the deployment manipulator is positioned such that the central longitudinal axis forms a second angle of between 45 and 90 degrees with a line defined by the first point and the second point.

Typically, the annuloplasty ring includes a partial annuloplasty ring, and positioning the deployment manipulator includes positioning the deployment manipulator within the lumen of the partial annuloplasty ring.

In an embodiment, the deployment manipulator includes steering functionality, and placing the sleeve includes steering the deployment manipulator using the steering functionality.

For some applications, deploying the anchor includes deploying the anchor from the atrium into an upper region of a ventricular wall near the atrium.

For some applications, the method further includes positioning a pusher element at least partially within the lumen of the sleeve of the annuloplasty ring; and moving the distal end of the deployment manipulator proximally within the sleeve by pushing the pusher element distally such that the pusher element engages an interior surface of the sleeve.

In an embodiment, the method further includes tightening the annuloplasty ring by winding a flexible contracting member of the ring around a spool coupled to the ring.

There is additionally provided, in accordance with an embodiment of the present invention, a method including:

positioning an anchor deployment manipulator at least partially within a lumen of a sleeve of an annuloplasty ring;

placing, into an atrium of a subject in a vicinity of an annulus of an atrioventricular valve, at least a portion of the sleeve that contains a distal end of the deployment manipulator; and deploying at least one anchor from the distal end of the deployment manipulator through a wall of the sleeve into cardiac tissue of the subject, while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

For some applications, deploying includes deploying the at least one anchor while the angle is between 75 and 90 degrees.

In an embodiment, the deployment manipulator includes steering functionality, and placing the sleeve includes steering the deployment manipulator using the steering functionality.

Typically, the annuloplasty ring includes a partial annuloplasty ring, and positioning the anchor deployment manipulator includes positioning the anchor deployment manipulator at least partially within the lumen of the partial annuloplasty ring.

For some applications, the point on the wall is a first point on the wall, and the angle is a first angle, the at least one anchor is a first anchor of a plurality of anchors that also includes a second anchor most recently deployed before the first anchor through a second point on the wall, and deploying the first anchor includes deploying the first anchor while the distal end of the deployment manipulator is positioned such that the central longitudinal axis forms a second angle of between 45 and 90 degrees with a line defined by the first point and the second point.

For some applications, deploying the anchor includes deploying the anchor from the distal end of the deployment manipulator such that a coupling element of the anchor enters the cardiac tissue in a direction parallel to the central longitudinal axis.

For some applications, the anchor is shaped so as to define a coupling head and a tissue coupling element, which is shaped so as to define a shape selected from the group consisting of: a helix, a spiral, and a screw shaft, and deploying the anchor includes screwing the tissue coupling element into the cardiac tissue.

In an embodiment, the method further includes tightening the annuloplasty ring by winding a flexible contracting member of the ring around a spool coupled to the ring.

For some applications, deploying the anchor includes deploying the anchor from the atrium into an upper region of a ventricular wall near the atrium.

For some applications, the deployment manipulator includes an anchor driver positioned within a sheath, the at least one anchor includes a plurality of anchors, and deploying the at least one anchor includes:

loading a first one of the anchors onto the anchor driver;

deploying the first one of the anchors through a wall of the sleeve and into the cardiac tissue;

withdrawing the anchor driver from the sheath and a body of the subject, while leaving the sheath lumen of the sleeve;

subsequently loading a second one of the anchors onto the anchor driver while the anchor driver is outside the body;

subsequently reintroducing the anchor driver into the body and the sheath; and subsequently deploying the second one of the anchors through the wall of the sleeve into the cardiac tissue.

For some applications, placing the at least a portion of the sleeve includes placing the at least a portion of the sleeve into a right atrium of the subject in a vicinity of a tricuspid valve. Alternatively, placing the at least a portion of the sleeve includes placing the at least a portion of the sleeve into a left atrium of the subject in a vicinity of the annulus of a mitral valve.

There is yet additionally provided, in accordance with an embodiment of the present invention, a method including:

positioning, during a transcatheter procedure, an anchor deployment manipulator at least partially in an atrium of a subject;

placing, into the atrium in a vicinity of an annulus of an atrioventricular valve, at least a portion of an annuloplasty ring; and coupling the annuloplasty ring to cardiac tissue by deploying at least one anchor from the deployment manipulator in the atrium and into an upper region of a ventricular wall near the atrium.

Typically, the atrioventricular valve is selected from the group consisting of: a mitral valve and a tricuspid valve.

In an embodiment, positioning the anchor deployment manipulator includes positioning at least a distal end of the deployment manipulator within a lumen of a sleeve of the annuloplasty ring, and coupling includes coupling the ring to the cardiac tissue by deploying the at least one anchor from the distal end of the deployment manipulator in the atrium, through a wall of the sleeve, and into the upper region of the ventricular wall. For some applications, deploying the anchor includes deploying the anchor into the upper region of the ventricular wall while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

For some applications, deploying the anchor includes deploying the anchor from the distal end of the deployment manipulator into the upper region of ventricular wall such that a coupling element of the anchor enters the ventricular wall in a direction parallel to a central longitudinal axis of the deployment manipulator through the distal end of the deployment manipulator.

There is further provided, in accordance with an embodiment of the present invention, a method including:

positioning an anchor deployment manipulator and a pusher element at least partially within a lumen of a sleeve of an annuloplasty ring;

placing, into an atrium of a subject in a vicinity of an annulus of an atrioventricular valve, at least a portion of the sleeve that contains a distal end of the deployment manipulator and a distal end of the pusher element;

moving the distal end of the deployment manipulator proximally within the sleeve by pushing the pusher element distally such that the pusher element engages an interior surface of the sleeve; and after moving the distal end of the deployment manipulator, deploying an anchor from the distal end of the deployment manipulator through a wall of the sleeve into cardiac tissue.

For some applications, the deployment manipulator includes an outer tube that is shaped so as to define an opening that is within 3 mm of a distal end of the tube, and positioning the pusher element at least partially within the lumen of the sleeve includes positioning the pusher element such that (a) a distal portion of the pusher element extends out of the tube through the opening and into the lumen of the sleeve, and (b) a proximal portion of the pusher element passes through the tube from the opening to a proximal end of the tube.

For some applications, the deployment manipulator includes an outer tube, and positioning the pusher element at least partially within the lumen of the sleeve includes positioning the pusher element outside of the outer tube.

For some applications, moving includes moving the distal end of the deployment manipulator by pushing the pusher element distally such that the pusher element engages a distal end of the sleeve. Alternatively or additionally, moving includes moving the distal end of the deployment manipulator by pushing the pusher element distally such that the pusher element engages the wall of the sleeve.

For some applications, moving the distal end of the deployment manipulator includes moving the distal end of the deployment manipulator a certain distance by pushing the pusher element the certain distance.

There is additionally provided, in accordance with an embodiment of the present invention, a method including:

coupling a sleeve of an annuloplasty ring to cardiac tissue of a subject at a plurality of sites in a vicinity of an annulus of an atrioventricular valve;

partially inserting a screwdriver tool into a lumen of the sleeve, the tool having a head and a shaft; and rotating the screwdriver tool such that the head, while within the lumen of the sleeve, shortens the ring by rotating a contracting mechanism of the ring that tightens an elongated contracting member coupled to the sleeve.

Typically, the annuloplasty ring includes a partial annuloplasty ring, and coupling includes coupling the sleeve of the partial annuloplasty ring to the cardiac tissue.

The present invention will be more fully understood from the following detailed description of applications thereof, taken together with the drawings, in which:

BRIEF DESCRIPTION OF THE DRAWINGS

FIGS. 1A and 1B are schematic illustrations of an adjustable partial annuloplasty ring in a non-contracted state, in accordance with respective applications of the present invention;

FIG. 2 is a schematic longitudinal cross-sectional illustration of an anchor deployment manipulator, in accordance with an application of the present invention;

FIG. 3 is a schematic longitudinal cross-sectional illustration of the anchor deployment manipulator of FIG. 2 advanced into the annuloplasty ring of FIG. 1A, in accordance with an application of the present invention;

FIG. 4 is a schematic cross-sectional illustration of the anchor deployment manipulator of FIG. 2 advanced into the annuloplasty ring of FIG. 1A or 1B, taken along section IV-IV of FIG. 3, in accordance with an application of the present invention;

FIGS. 5A-B are schematic illustrations of a rotation tool being used to rotate a spool of a contracting mechanism of the rings of FIGS. 1A and 1B, respectively, in accordance with respective applications of the present invention;

FIGS. 6A and 6B are schematic isometric and cross-sectional illustrations, respectively, of another configuration of a rotation tool being used to rotate a spool of a contracting mechanism of the ring of FIG. 1B, in accordance with an application of the present invention;

FIGS. 9A-C are schematic cross-sectional illustrations of a rotation handle, in accordance with an application of the present invention;

FIGS. 10A-D are schematic isometric illustrations of the rotation handle of FIGS. 9A-C, in accordance with an application of the present invention;

FIGS. 11A-I are schematic illustrations of a procedure for implanting the annuloplasty ring of FIG. 1A to repair a mitral valve, in accordance with an application of the present invention;

FIG. 13 is a schematic illustration of the system of FIGS. 1-4 comprising a flexible pusher element, in accordance with an application of the present invention;

FIG. 14 is a schematic illustration of a pusher tube applied to a proximal end of the sleeve of FIGS. 1-4, in accordance with an application of the present invention;

FIGS. 15 and 16 are schematic illustrations of the system of FIGS. 1-4 comprising a steerable tube, in accordance with respective applications of the present invention;

FIGS. 18A and 18B are schematic illustrations of another configuration of the pusher tube of FIG. 14, in accordance with an application of the present invention;

FIG. 19 is a schematic illustration of the system of FIGS. 1-4 and FIGS. 18A-B comprising an external control handle, in accordance with an application of the present invention;

FIGS. 20A-E are schematic cross-sectional and isometric illustrations of a configuration of a driver head of an anchor driver, in accordance with an application of the present invention;

DETAILED DESCRIPTION OF EMBODIMENTS

Figure 1B:
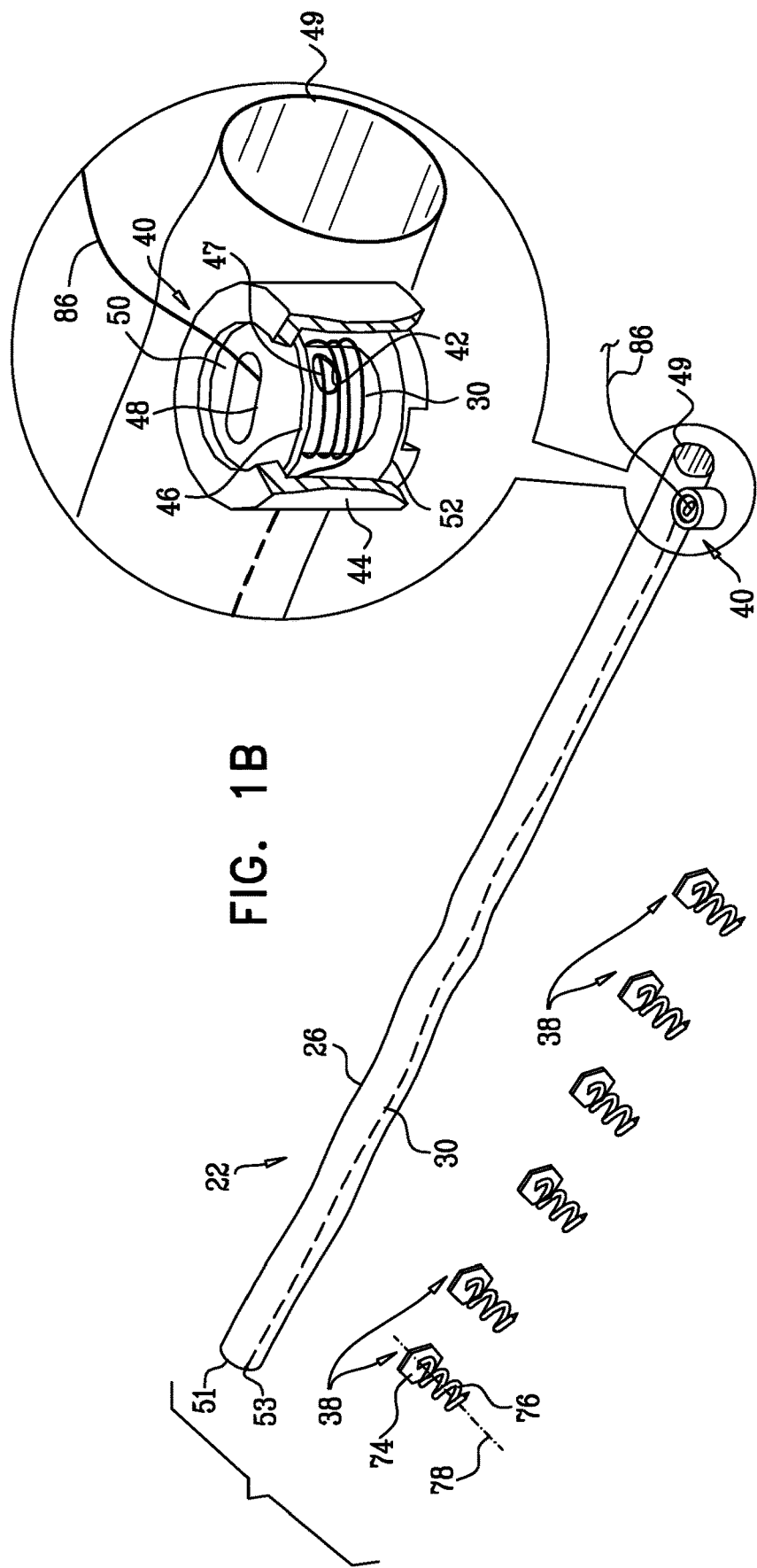

FIGS. 1-4 are schematic illustrations of a system 20 for repairing a dilated atrioventricular valve, such as a mitral valve, in accordance with an application of the present invention. System 20 comprises an adjustable partial annuloplasty ring 22, shown alone in FIGS. 1A and 1B in a non-contracted state, and an anchor deployment manipulator 24, shown alone in FIG. 2. Annuloplasty ring 22 comprises a flexible sleeve 26. Anchor deployment manipulator 24 is advanced into sleeve 26, as shown in FIGS. 3 and 4, and, from within the sleeve, deploys anchors 38 through a wall of the sleeve into cardiac tissue, thereby anchoring the ring around a portion of the valve annulus.

FIGS. 1A and 1B are schematic illustration of annuloplasty ring 22 in a non-contracted state, in accordance with respective applications of the present invention. Sleeve 26 is typically configured to be placed only partially around the valve annulus (i.e., to assume a C-shape), and, once anchored in place, to be contracted so as to circumferentially tighten the valve annulus. Alternatively, the ring is configured to be placed entirely around the valve annulus. In order to tighten the annulus, annuloplasty ring 22 comprises a flexible elongated contracting member 30 that extends along the ring.

Annuloplasty ring 22 further comprises a contracting mechanism 40, which facilitates contracting of the annuloplasty ring. Contracting mechanism 40 is described in more detail hereinbelow. In addition, the ring comprises a plurality of anchors 38, typically between about 5 and about 20 anchors, such as about 10 or about 16 anchors. In FIGS. 1A and 1B, anchors 38 are shown prior to their insertion into ring 22, while in FIG. 3 one of the anchors is shown deployed through the wall of sleeve 26, and a second one of the anchors is shown during deployment by anchor deployment manipulator 24. The insertion of the anchors into the sleeve and deployment of the anchors into cardiac tissue is described in detail hereinbelow.

Flexible sleeve 26 may comprise a braided, knitted, or woven mesh or a tubular structure comprising ePTFE. For some applications, the braid comprises metal and fabric fibers. The metal fibers, which may comprise Nitinol for example, may help define the shape of the sleeve, e.g., hold the sleeve open to provide space for passage and manipulation of deployment manipulator 24 within the sleeve. The fabric fibers may promote tissue growth into the braid. Optionally, the sleeve is somewhat elastic, which gives the sleeve a tendency to longitudinally contract, thereby helping tighten the sleeve. For example, the sleeve may be bellows- or accordion-shaped.

Typically, the sleeve is configured to have a tendency to assume a straight shape. This straightness helps the surgeon locate the next site for each subsequent anchor during the implantation procedure, as described hereinbelow with reference to FIGS. 11A-I. For example, because the sleeve assumes a generally straight shape, the sleeve may help provide an indication of distance between adjacent anchoring sites.

For some applications, the sleeve is configured to have a controllably variable stiffness. For example, a somewhat stiff wire may be placed in the sleeve to provide the stiffness, and subsequently be removed at the conclusion of the implantation procedure when the stiffness is no longer useful.

Elongated contracting member 30 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contracting member 30 comprises a braided polyester suture (e.g., Ticron). For some applications, contracting member 30 is coated with polytetrafluoroethylene (PTFE). For some applications, contracting member 30 comprises a plurality of wires that are intertwined to form a rope structure.

For some applications, contracting member 30 is positioned at least partially within a lumen of the sleeve 26, such as entirely within the lumen (as shown in FIGS. 1A-B, 5A-B, 6A, 11H, and 11O. For some applications in which the contracting member is positioned partially within the lumen, the contracting member is sewn into the wall of the sleeve, such that the contracting member is alternatingly inside and outside of the sleeve along the length of the sleeve (as shown in FIGS. 3, 13, and 14). Optionally, sleeve 26 defines an internal channel within which member 30 is positioned (configuration not shown). Alternatively, the contracting member is disposed outside the lumen of the sleeve, such as alongside an outer wall of the sleeve. For example, sleeve 26 may define an external channel within which member 30 is positioned, or the sleeve may comprise or be shaped so as to define external coupling elements, such as loops or rings (configuration not shown). For some applications, contracting member 30 is positioned approximately opposite the anchors.

For some applications of the present invention, contracting mechanism 40 comprises a rotatable structure, such as a spool 46. The rotatable structure is arranged such that rotation thereof contracts annuloplasty ring 22. For some applications, a first end 47 of contracting member 30 is coupled to the spool. For some applications, contracting mechanism 40 further comprises a housing 44 that houses the rotatable structure, e.g., the spool. Spool 46 is positioned in a vicinity of (e.g., within 1 cm of) either a distal end 51 of sleeve 26, as shown in FIGS. 1A and 3, or a proximal end 49 of sleeve 26, as shown in FIG. 1B. For some applications, a second end 53 of contracting member 30 is coupled to the sleeve in a vicinity of (e.g., within 1 cm of) the end of the sleeve opposite the end to which the spool is positioned. In the configuration shown in FIGS. 1A and 3, second end 53 of contracting member 30 is coupled to the sleeve in a vicinity of proximal end 49 of the sleeve, while in the configuration shown in FIG. 1B, the second end of the contracting member is coupled to the sleeve in a vicinity of distal end 51 of the sleeve. Rotation of spool 46 winds a portion of the contracting member around the spool, thereby pulling the far end of the ring toward the spool and shortening and tightening the ring.

Alternatively, in some configurations, spool 46 is positioned at an intermediary position along the sleeve, rather than in a vicinity of one of the ends. For these configurations, contracting member 30 comprises two contracting members, which are respectively connected to the two ends of the sleeve, and both of which are connected to the spool. Rotating the spool contracts both contracting members. These configuration may be implemented using techniques described in U.S. patent application Ser. No. 12/341,960 to Cabin, which published as US Patent Application Publication 2010/0161047 and is incorporated herein by reference, with reference to FIG. 15 thereof.

For some applications, spool 46 is shaped to provide a hole 42 or other coupling mechanism for coupling first end 47 of contracting member 30 to the spool, and thereby to contracting mechanism 40.

For other applications, contracting member 30 comprises at least one wire (e.g., exactly one wire) that passes through a coupling mechanism of spool 46, in order to couple the wire to the spool. The ends of the wire are brought together, and together serve as second end 53 of contracting member 30, and may be coupled to one of the several locations of the sleeve mentioned hereinabove. In this configuration, approximately the longitudinal center of the wire serves as first end 47 of the contracting member.

For some applications, spool 46 is shaped to define a driving interface 48. For some applications, driving interface 48 is female. For example, the interface may be shaped to define a channel which extends through the cylindrical portion of spool 46 from an opening provided by an upper surface 50 of spool 46 to an opening provided by a lower surface 52 of spool 46. Alternatively, driving interface 48 is shaped so as to define an indentation (e.g., a groove) that does not extend entirely through the cylindrical portion of the spool. Further alternatively, driving interface 48 is male, and defines a protrusion, e.g., a hexagonal head or a head having another shape.

For some applications, a distal portion of a rotation tool 80, which is described hereinbelow with reference to FIGS. 5A-B, engages spool 46 via driving interface 48 and rotates spool 46 in response to a rotational force applied to the rotation tool. The rotational force applied to the rotation tool rotates spool 46 via the portion of the rotation tool that engages driving interface 48 of spool 46.

Spool 46 typically comprises a locking mechanism that prevents rotation of the spool after contracting member 30 has been tightened. For example, locking techniques may be used that are described with reference to FIG. 4 of abovementioned U.S. application Ser. No. 12/341,960 to Cabin, and/or with reference to FIGS. 6B, 7, and 8 hereinbelow.

Alternatively, for some applications, contracting mechanism 40 is configured to tighten contracting member 30, crimp the contracting member to hold the contracting member taut, and subsequently cut the excess length of the contracting member.

FIG. 2 is a schematic longitudinal cross-sectional illustration of anchor deployment manipulator 24, FIG. 3 is a schematic longitudinal cross-sectional illustration of the anchor deployment manipulator advanced into annuloplasty ring 22, and FIG. 4 is a schematic cross-sectional illustration of the anchor deployment manipulator advanced into the annuloplasty ring, taken along section IV-IV of FIG. 3, in accordance with an application of the present invention. Anchor deployment manipulator 24 is advanced into a lumen of sleeve 26, and, from within the lumen, deploys anchors 38 through a wall of the sleeve and into cardiac tissue, thereby anchoring the sleeve around a portion of the valve annulus. Typically, annuloplasty ring 22 and anchor deployment manipulator 24 are introduced into the heart via a sheath 104, as described hereinbelow with reference to FIGS. 11A-I.

For some applications, at least one of anchors 38 is deployed from a distal end 60 of deployment manipulator 24 while the distal end is positioned such that a central longitudinal axis 62 through distal end 60 of deployment manipulator 24 forms an angle α (alpha) of between about 45 and 90 degrees with the wall of sleeve 26 at the point at which the anchor penetrates the wall, such as between about 75 and 90 degrees, e.g., about 90 degrees. (In FIG. 3, a line 64 schematically illustrates the plane tangential to the wall of the sleeve at the anchor-penetration point.) This anchor-penetration point is typically at a portion of the sleeve that extends distally beyond the distal end of outer tube 66 of deployment manipulator 24 (which is described hereinbelow), i.e., that is no longer in contact with the outer surface of outer tube 66. Typically, all of the anchors are deployed at such angles, with the possible exception of the first anchor deployed near the distal end of the sleeve.

For some applications, at least one of anchors 38 is deployed from distal end 60 of deployment manipulator 24 while distal end 60 is positioned such that longitudinal axis 62 through distal end 60 of deployment manipulator 24 forms an angle β (beta) of between about 45 and 90 degrees (such as between about 75 and 90 degrees, e.g., about 90 degrees) with a line 65 defined by (a) a first point 67 at which the anchor currently being deployed penetrates the wall of the sleeve and (b) a second point 69 at which a most recently previously deployed anchor penetrates the wall of sleeve 26. Typically, all of the anchors are deployed at such angles, with the exception of the first anchor deployed near the distal end of the sleeve.

Typically, the anchors are deployed from distal end 60 of deployment manipulator 24 into the cardiac tissue in a direction parallel to central longitudinal axis 62.

For some applications, anchor deployment manipulator 24 comprises an outer tube 66 (sometimes referred to herein, including in the claims, as a "deployment manipulator tube") and an anchor driver 68 which is at least partially positioned within tube 66. Anchor driver 68 comprises an elongated, flexible shaft 70, having at its distal end a driver head 72. Rotation of the anchor driver screws the anchors into the cardiac tissue. Each of anchors 38 is shaped so as to define a coupling head 74 and a tissue coupling element 76.

The anchors are typically rigid. Tissue coupling elements 76 may, for example, be helical or spiral in shape (e.g., having the shape of a corkscrew), as shown in the figures, may comprise screws, or may have other shapes. Coupling heads 74 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Alternatively, the anchors may comprise staples, clips, spring-loaded anchors, or other tissue anchors described in the references incorporated hereinabove in the Background section, or otherwise known in the art. For some applications, anchor deployment manipulator 24 and/or anchors 38 are implemented using techniques described hereinbelow with reference to FIGS. 20A-E.

For some applications, outer tube 66 of deployment manipulator 24 is steerable, as known in the catheter art, while for other applications, a separate steerable tube is provided, as described hereinbelow with reference to FIG. 15 or FIG. 16. To provide steering functionality to deployment manipulator 24, outer tube 66, steerable tube 300 (FIG. 15), or steerable tube 320 (FIG. 16), as the case may be, typically comprises one or more steering wires, the pulling and releasing of which cause deflection of the distal tip of the tube.

For some applications of the present invention, each of tissue coupling elements 76 is shaped so as to define a longitudinal axis 78 (shown in FIGS. 1A-B), and is configured to penetrate the cardiac tissue in a direction parallel to longitudinal axis 78. Deployment manipulator 24 is configured to deploy tissue coupling element 76 from distal end 60 of the deployment manipulator through the wall of sleeve 26 in a direction parallel to longitudinal axis 78 and parallel to central longitudinal axis 62 through distal end 60 of deployment manipulator 24 (shown in FIGS. 2, 3, and 12-15).

For some applications, the plurality of anchors are applied using the deployment manipulator by loading a first one of the anchors onto the anchor driver, and deploying the anchor into the cardiac tissue. The anchor driver is withdrawn from the subject's body (typically while leaving outer tube 66 of the deployment manipulator in place in the sleeve), and a second one of the anchors is loaded onto the anchor driver. The anchor driver is reintroduced into the outer tube of the deployment manipulator, and the second anchor is deployed. These steps are repeated until all of the anchors have been deployed. Alternatively, the entire deployment manipulator, including the anchor driver, is removed from the body and subsequently reintroduced after being provided with another anchor. Further alternatively, the deployment manipulator is configured to simultaneously hold a plurality of anchors, and to deploy them one at a time (configuration not shown).

Typically, the first anchor 38 is deployed most distally in sleeve 26 (generally at or within a few millimeters of a distal end 51 of the sleeve), and each subsequent anchor is deployed more proximally, such that sleeve 26 is gradually pulled off (i.e., withdrawn from) deployment manipulator 24 in a distal direction during the anchoring procedure. Typically, as the sleeve is pulled off the deployment manipulator, the deployment manipulator is moved generally laterally along the cardiac tissue, as shown in FIG. 3.

For some applications, an implant structure is provided. The implant structure comprises a contracting mechanism, such as contracting mechanism 40. The contracting mechanism comprises a rotatable structure, arranged such that rotation of the rotatable structure contracts the implant structure. The implant further comprises a longitudinal member, which is coupled to the contracting mechanism. A tool, such as rotation tool 80, is provided for rotating the rotatable structure. The tool is configured to be guided over the longitudinal member, to engage the rotatable structure, and to rotate the rotatable structure in response to a rotational force applied to the tool.

Reference is now made to FIGS. 5A-B, which are schematic illustrations of rotation tool 80 being used to rotate spool 46 of contracting mechanism 40 of ring 22, in accordance with respective applications of the present invention. For these application, the implant structure comprises annuloplasty ring 22. Rotation tool 80 has a head 82 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided. Typically, the rotation tool comprises a shaft 84, at least a portion of which is flexible. For some applications, the rotation tool is used that is described in above-referenced U.S. patent application Ser. No. 12/341,960, with reference to FIG. 4 thereof. Alternatively, anchor driver 68 of deployment manipulator 24 serves as rotation tool 80, and is used to rotate the spool, in which case driving interface 48 is appropriately shaped to receive driver head 72 of anchor driver 68.

In the configuration shown in FIG. 5A, contracting member 30 is coupled to distal end 51 of sleeve 26, as shown hereinabove in FIGS. 1A and 3. Contracting mechanism 40 is oriented such that driving interface 48 thereof is accessible from within sleeve 26. Rotation tool 80 is inserted into sleeve 26, and used to rotate spool 46 via the driving interface. Alternatively, anchor driver 68 of deployment manipulator 24 serves as rotation tool 80, and is used to rotate the spool, in which case driving interface 48 is appropriately shaped to engage driver head 72 of anchor driver 68. In either case, the sleeve thus serves to guide the rotation tool to driving interface 48. For some applications, an interior surface of the sleeve is tapered near the distal end of the sleeve, to help guide the head 82 of rotation tool 80 to the driving interface. For some applications, during the implantation procedure, anchor deployment manipulator 24 is left slightly inserted into proximal end 49 of sleeve 26 after all of anchors 38 have been deployed, in order to facilitate passage of rotation tool 80 into sleeve 26.

In the configuration shown in FIG. 5B, access to driving interface 48 is provided from outside sleeve 26. For some applications, contracting mechanism 40 comprises a longitudinal member 86, such as a wire, that is attached to the mechanism and passes out of the body of the subject, typically via sheath 104. In order to readily bring the rotation tool to driving interface 48, rotation tool 80 is guided over (as shown) the longitudinal member, or alongside the longitudinal member (configuration not shown). Alternatively, the longitudinal member comprises a suture or other highly flexible element. For some applications, the longitudinal member comprises a tube, through which rotation tool 80 is passed to bring the tool to the driving interface 48. For some applications, longitudinal member 86 has a diameter of between 0.1 and 1 mm, such as 0.4 mm.

For some applications, longitudinal member 86 is looped through contracting mechanism 40, and both ends of the longitudinal member are brought together and extend outside of the subject's body. The longitudinal member is decoupled from the contracting mechanism by releasing one end of the longitudinal member, and pulling on the other end to draw the longitudinal member away from the contracting mechanism.

For some applications, contracting mechanism 40 is positioned in a vicinity of (e.g., within 1 cm of) distal end 51 of sleeve 26, and access to driving interface 48 is provided from outside sleeve 26, as described with reference to FIG. 5B (in which the contracting mechanism is positioned in a vicinity of proximal end 49 of the sleeve).

For some applications in which access to driving interface 48 is provided from outside sleeve 26, the rotation tool is initially removably attached to the driving interface, prior to the commencement of the implantation procedure, and is subsequently decoupled from the driving interface after spool 46 has been rotated. In these applications, contracting mechanism 40 may be positioned in a vicinity of distal end 51 or proximal end 49 of sleeve 26, or at an intermediate location along the sleeve. Optionally, at least a portion of a shaft of the rotation tool is positioned within sheath 104, which is described hereinbelow with reference to FIGS. 11A-I.

Figure 6B:
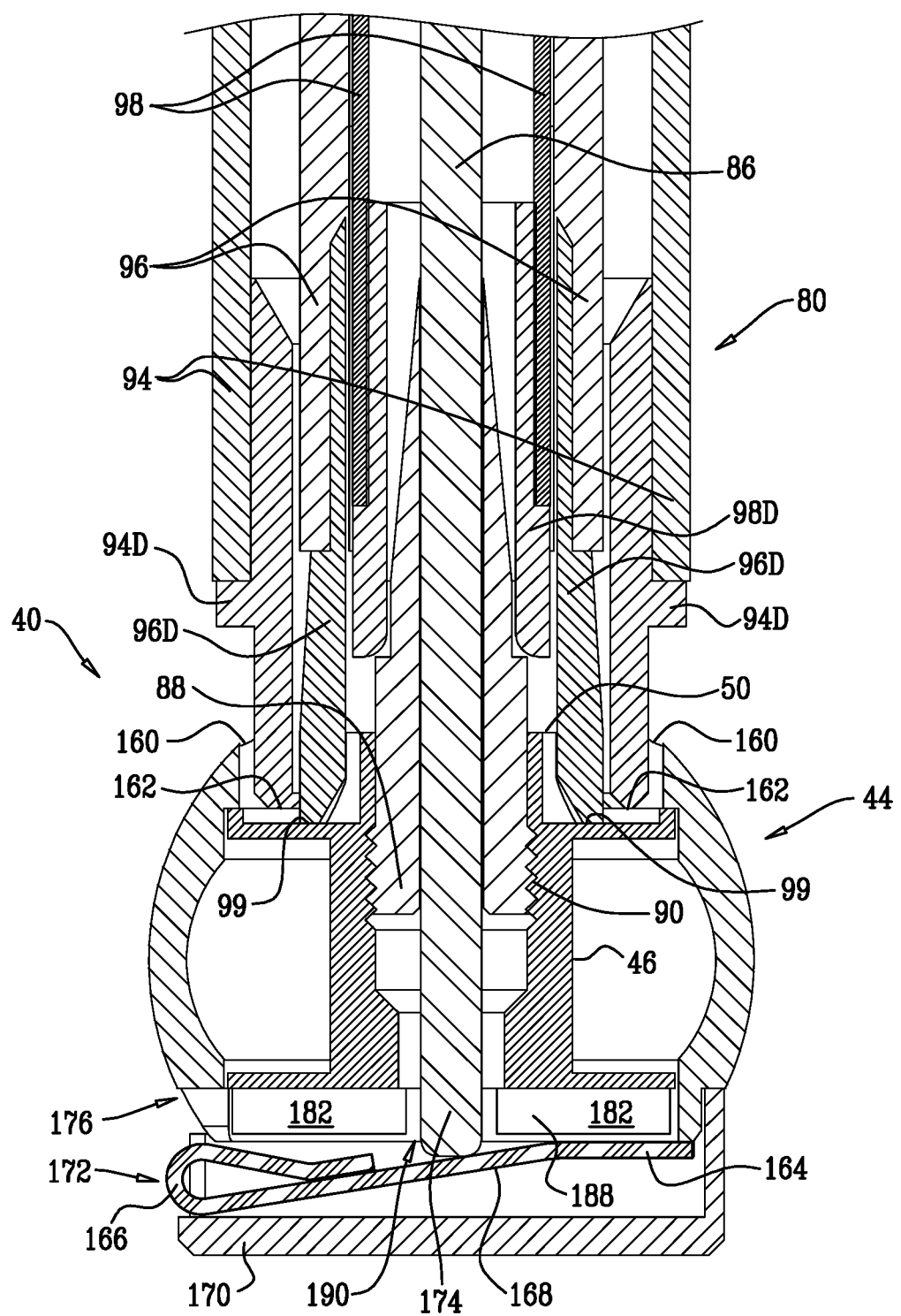

Reference is now made to FIGS. 6A and 6B, which are schematic isometric and cross-sectional illustrations, respectively, of another configuration of rotation tool 80 being used to rotate spool 46 of contracting mechanism 40 of ring 22, in accordance with an application of the present invention. In this application, as in the configurations shown in FIGS. 1B and 5B, access to driving interface 48 is provided from outside sleeve 26. Contracting mechanism 40 comprises longitudinal member 86 that is attached to the contracting mechanism 40 and passes out of the body of the subject, typically via sheath 104. In order to readily bring the rotation tool to driving interface 48, rotation tool 80 is guided over longitudinal member 86. In this application, rotation tool 80 comprises one or more tubes that pass over the longitudinal member, as described below.

As mentioned above, for some application longitudinal member comprises a wire, which may comprise metal. Because the wire is fairly stiff, the wire generally maintains its direction and orientation with respect to contracting mechanism 40. The wire thus readily guides the tubes to the contracting mechanism such that the tubes have a desired orientation and position with respect to the contracting mechanism.

Longitudinal member 86 is removably coupled to contracting mechanism 40, typically to a central portion of upper surface 50 of spool 46. For some applications, a distal portion 88 of longitudinal member 86 is shaped so as to define a screw thread 90. Distal portion 88 is screwed into a threaded opening 92 of upper surface 50, in order to removably couple longitudinal member 86 to contracting mechanism 40. Typically, the distal portion is initially coupled to the contracting mechanism before annuloplasty ring 22 is placed into an atrium of the patient. As described below, the distal portion is decoupled from the contracting mechanism after spool 46 has been rotated to tighten ring 22. For some applications, distal portion 88 comprises a discrete element that is fixed to longitudinal member 86, while for other application, distal portion 88 is integral with longitudinal member 86.

For some applications, rotation tool 80 comprises an inner (first) tube 98, an intermediate (second) tube 96, and, optionally, an outer (third) tube 94. Rotation of each of the tubes is independently controlled, such as using techniques described hereinbelow with reference to FIGS. 9A-C and/or 10A-D. For some applications, a distal portion of each of tubes 94, 96, and 98 that enters the patient's body comprises braided plastic, and a proximal portion of each of the tubes that does not enter the patient's body comprises a hard material, such as metal (not shown). For example, the distal and proximal portions may have lengths of between 50 and 100 cm and between 50 and 350 cm, respectively. Distal-most portions 94D, 96D, and 98D, respectively, of the distal portions typically comprise a hard material, such as metal, in order to engage other elements, as described immediately below. Typically, the distal-most portions comprise separate elements that are coupled to their respective tubes. For example, the distal-most portions may have lengths of between 1 and 10 mm.

Intermediate tube 96 is configured to rotate spool 46. To this end, intermediate tube 96 (such as distal-most portion 96D thereof) is configured to engage upper surface 50 of spool 46. To enable such engagement, the upper surface typically is shaped so as to define one or more indentations 99 (e.g., grooves), in which corresponding protrusions at the distal end of intermediate tube 96 are positioned, such as by gently rotating tube 96 (or all of the tubes) until such engagement occurs. (Springs 460, described hereinbelow with reference to FIGS. 9A-C and 10A-D, may be provided to assist with such engagement.) The radius of intermediate tube 96 is approximately equal to the distance of each of the indentations from a center of upper surface 50, so that the protrusions at the distal end of the tube are aligned with the indentations. Alternatively, the upper surface defines one or more protrusions, which engage indentations on the distal end of tube 96 (configuration not shown). Indentations 99 or the protrusions thus serve as driving interface 48.

Rotation of intermediate tube 96 causes corresponding rotation of spool 46, thereby winding contracting member 30 around the spool, and tightening the contracting member.

Outer tube 94, if provided, is configured to prevent rotation of spool housing 44 during rotation of spool 46. To this end, outer tube 94 (such as distal-most portion 94D thereof) is configured to engage an upper surface 160 of spool housing 44. To enable such engagement, the upper surface typically is shaped so as to define one or more indentations 162 (e.g., grooves), in which corresponding protrusions at the distal end of outer tube 94 are positioned, such as by gently rotating the tube (or all of the tubes) until such engagement occurs. (Springs 460, described hereinbelow with reference to FIGS. 9A-C and 10A-D, may be provided to assist with such engagement.) The radius of outer tube 94 is approximately equal to the distance of each of the indentations from a center of spool housing 44, so that the protrusions at the distal end of the tube are aligned with the indentations. Alternatively, the upper surface defines one or more protrusions, which engage indentations on the distal end of tube 94 (configuration not shown).

During rotation of intermediate tube 96 for rotating spool 46, outer tube 94 is held rotationally stationary, thereby stabilizing spool housing 44 and enabling spool 46 to rotate with respect to housing 44.

Inner tube 98 is configured to decouple longitudinal member 86 from spool 46 after contracting member 30 has been sufficiently wound around the spool, as described above. To this end, a distal portion of the inner tube (such as distal-most portion 98D thereof) is shaped so as to engage a distal portion of longitudinal member 86, which is typically shaped so as to couple with the distal portion of the inner tube.

Rotation of the inner tube, while intermediate tube 96 is prevented from rotating and thus prevents rotation of spool 46, causes corresponding rotation of longitudinal member 86, and unscrews the longitudinal member from spool 46.

Longitudinal member 86 and spool 46 are typically configured such that this unscrewing rotation is in the opposite direction of the rotation of the spool that tightens the contracting member. For example, clockwise rotation of the spool (looking down on the spool) may wind the contracting member around the spool, while counterclockwise rotation of longitudinal member 86 unscrews the longitudinal member from the spool. To enable the engagement of inner tube 98 with the distal portion of the longitudinal member, the distal portion may include a flat portion.

Figure 7:
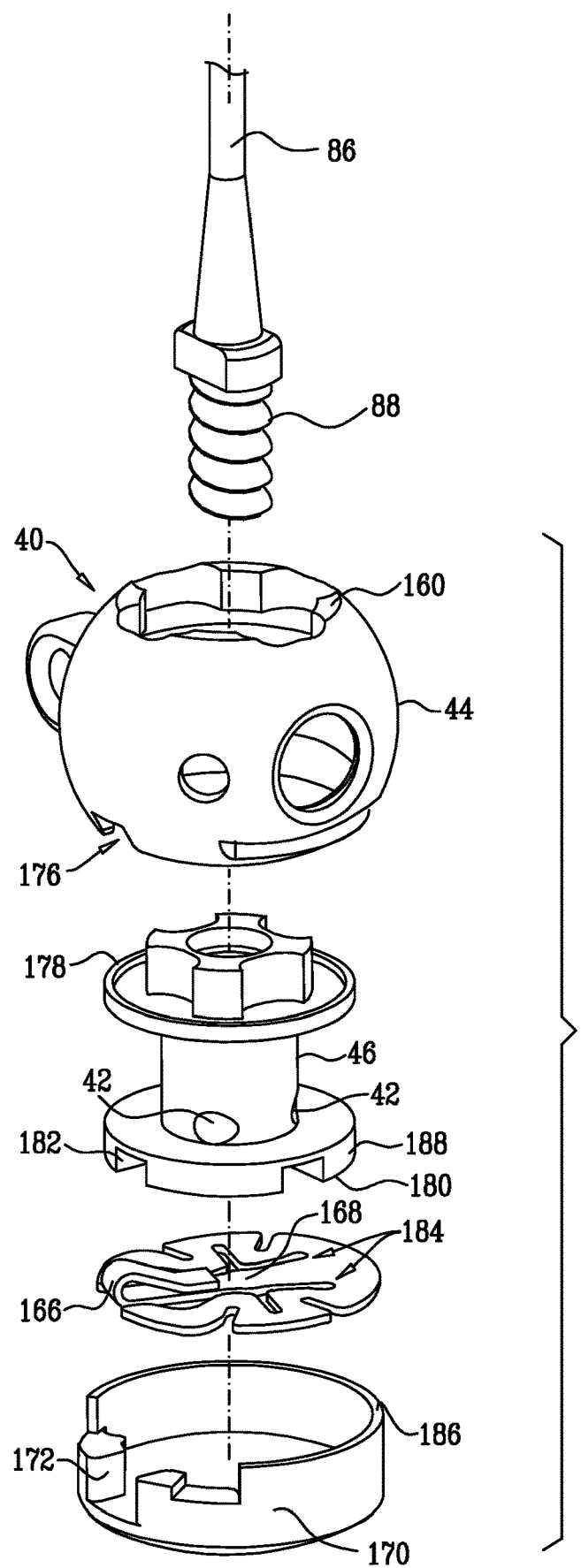
FIG. 7 shows a relationship among individual components of the contracting mechanism of FIGS. 6A and 6B, in accordance with an application of the present invention.

FIG. 7 shows a relationship among individual components of contracting mechanism 40, in accordance with an application of the present invention. Contracting mechanism 40 is shown as comprising spool housing 44 which defines an upper surface 160 and a recessed portion 176. Spool 46 is configured to be disposed within housing 44 and defines an upper surface 178, a lower surface 180 and a cylindrical body portion disposed vertically between surfaces 178 and 180.

Lower surface 180 of spool 46 is shaped to define one or more (e.g., a plurality, as shown) recesses 182 which define structural barrier portions 188 of lower surface 180. It is to be noted that any suitable number of recesses 182 may be provided, e.g., between 1 and 10 recesses, circumferentially with respect to lower surface 180 of spool 46.

For some applications, as mentioned above, spool 46 comprises a locking mechanism 164. For some applications, locking mechanism 164 is coupled, e.g., welded, at least in part to a lower surface of spool housing 44. Typically, locking mechanism 164 defines a mechanical element having a planar surface that defines slits 184. The surface of locking mechanism 164 may also be curved, and not planar. Locking mechanism 164 is shaped to provide a protrusion 166 which projects out of a plane defined by the planar surface of the mechanical element. The slits define a depressible portion 168 of locking mechanism 164 that is disposed in communication with and extends toward protrusion 166. Depressible portion 168 is moveable in response to a force applied thereto by a distal element 70 that extends in a distal direction from distal portion 88 of longitudinal member 86, beyond threaded opening 92 of upper surface 50, as shown in FIG. 6B.

It is to be noted that the planar, mechanical element of locking mechanism 164 is shown by way of illustration and not limitation and that any suitable mechanical element having or lacking a planar surface but shaped to define at least one protrusion may be used together with locking mechanism 164.

A cap 170 is provided that is shaped so as to define a planar surface and an annular wall having an upper surface 186 that is coupled to, e.g., welded to, a lower surface of spool housing 44. The annular wall of cap 170 is shaped so as to define a recessed portion 172 of cap 170 that is in alignment with recessed portion 176 of spool housing 44.

Figure 8:
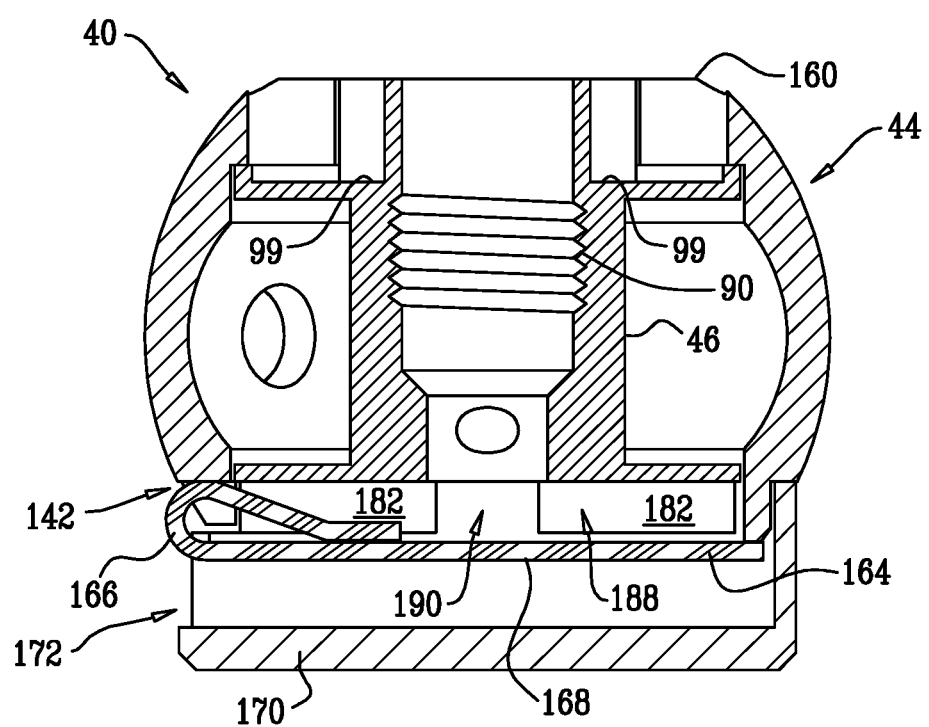
FIG. 8 is another cross-sectional illustration of the contracting mechanism of FIGS. 6A and 6B, in accordance with an application of the present invention.

Reference is again made to FIG. 6B, and is additionally made to FIG. 8, which is another cross-sectional illustration of contracting mechanism 40, in accordance with an application of the present invention. FIG. 6B shows contracting mechanism 40 in an unlocked state, while FIG. 8 shows the contracting mechanism in a locked state.

In the unlocked state shown in FIG. 6B, protrusion 166 of locking mechanism 164 is disposed within recessed portion 172 of cap 170. Longitudinal member 86 is shaped so as to define a distal force applicator 174 that extends distally, typically beyond screw thread 90. In the unlocked state, the force applicator extends through spool 46 and pushes against depressible portion 168 of locking mechanism 164. The depressible portion is thus pressed downward, as shown in FIG. 6B, freeing protrusion 166 from within a recess 190 defined by structural barrier portions 188 of the lower portion of spool 46. Additionally, protrusion 166 is freed from within recessed portion 176 provided by spool housing 44. As a result, contracting mechanism 40 is unlocked, and spool 46 may be rotated with respect to spool housing 44.

Cap 170 functions to restrict distal pushing of depressible portion 168 beyond a desired distance so as to inhibit deformation of locking mechanism 164. For applications in which contracting mechanism 40 is implanted in heart tissue, cap 170 also provides an interface between contracting mechanism 40 and the heart tissue. This prevents interference of heart tissue on contracting mechanism 40 during the locking and unlocking thereof. Additionally, cap 170 prevents damage to heart tissue by depressible portion 168 as it is pushed downward.

In the locked state shown in FIG. 8, protrusion 166 is positioned within a recess 190 of spool 46. Typically, the locked state is the resting state of locking mechanism 162. Depressible portion 168 is disposed in a horizontal position, in response to removal of distal force applicator 174 from within spool 46. Depressible portion 168 has a tendency to assume the horizontal position, as shown, and in the absence of a downward pushing force applied to depressible portion 168 by force applicator 174, depressible portion 168 returns to its horizontal position from its pushed-down state, as shown in FIG. 8. In this horizontal position, protrusion 166 of locking mechanism 164 is removed from recessed portion 172 of cap 170 and is returned within a recess 190 of spool 46 and thereby restricts movement of spool 46 and locks contracting mechanism 40. Additionally, protrusion 166 of locking mechanism 164 returns in part within recessed portion 176 of spool housing 44. Thus, recessed portion 176 of spool housing 44 provides supplemental locking of locking mechanism 164.

Reference is now made to FIGS. 9A-C and 10A-D, which are schematic cross-sectional and isometric illustrations, respectively, of a rotation handle 400, in accordance with an application of the present invention. For some applications, rotation handle 400 is used for controlling rotation tool 80, and thus the rotational positions of tubes 94, 96, and 98, described hereinabove with reference to FIGS. 6A-B. Alternatively, rotation handle 400 is used to rotate other tubes, such as for other medical applications.

Rotation handle 400 comprises a handle housing 410 and one or more knobs for controlling the rotation of the tubes. The housing is typically configured to be coupled to outer tube 94, such that the outer tube cannot rotate with respect to the housing. The handle may comprise a hollow coupling element 412, into which the outer tube is inserted and fixed. Intermediate tubes 96 and 98 are coupled to other elements of handle 400, as described below.

As mentioned above, for some applications handle 400 is used with rotation tool 80. For these applications, after annuloplasty ring 22 has been implanted, a proximal portion of longitudinal member 86 extends outside the patient's body, such as via sheath 104 (shown, for example, in FIGS. 2, 11C-I, and 12). Tubes 94, 96, and 98 are threaded over this proximal portion of the longitudinal member, such that the longitudinal member is directly within inner tube 98, which is in turn within intermediate tube 96, which is in turn within outer tube 94. The proximal end of longitudinal member 86 is threaded at least partially through the handle, such as entirely through the length of handle 400, from a distal end 414 thereof to a proximal end 416 thereof.

Longitudinal member 86 is coupled to the handle such that the longitudinal member is longitudinally fixed to the housing (i.e., cannot be withdrawn), but is allowed to rotate with respect to the housing. For some applications, handle 400 comprises a longitudinal member coupling assembly 418, for example positioned in a vicinity of proximal end 416 of the housing. Typically, longitudinal member coupling assembly 418 is configured to rotate with respect to the housing, thereby allowing longitudinal member 86 to rotate with respect to the housing. For some applications, longitudinal member coupling assembly 418 comprises a lever 452 that is biased by a spring 454 to pivot such that an end of the lever at a central longitudinal axis of handle 400 applies a force in a distal direction. The end of the level is shaped to allow longitudinal member 86 to be advanced toward proximal end 416 of handle 400, while preventing withdrawal of the longitudinal member in a distal direction.

For some applications, rotation handle 400 comprises an intermediate-tube (second-tube) rotation knob 430 and an inner-tube (first-tube) rotation knob 432. Optionally, intermediate-tube rotation knob 430 is positioned closer to distal end 414 of handle 400 than is inner-tube rotation knob 432. Intermediate-tube rotation knob 430 is coupled to intermediate tube 96 (e.g., using an adhesive), such that rotation of the knob rotates the tube. Inner-tube rotation knob 432 is coupled to inner tube 98 (e.g., using an adhesive), such that rotation of the knob rotates the tube. The two knobs thus enable convenient rotation of the tubes, either separately or together.

For some applications, rotation handle 400 further comprises a control knob 434, which, for some applications, is configured to slide longitudinally in distal and proximal directions over knobs 430 and 432. When control knob 434 is positioned in a first position (e.g., a first longitudinal position, such as a proximal position, as shown in FIGS. 9A and 9B), an inner surface of the control knob engages both knobs 430 and 432. Rotation of the control knob thus rotates both intermediate-tube rotation knob 430 (and thus intermediate tube 96) and inner-tube rotation knob 432, (and thus inner tube 98). The rotation of intermediate tube 96 rotates spool 46, as described hereinabove with reference to FIGS. 6A-B. The rotation of inner tube 98 rotates longitudinal member 86 at the same rate as the spool is rotated, such that longitudinal member 86 remains screwed into the spool. For some applications, the inner surface of the control knob is shaped so as to define ridges which matingly engage troughs defined by external surfaces of knobs 430 and 432.

Figure 9C:
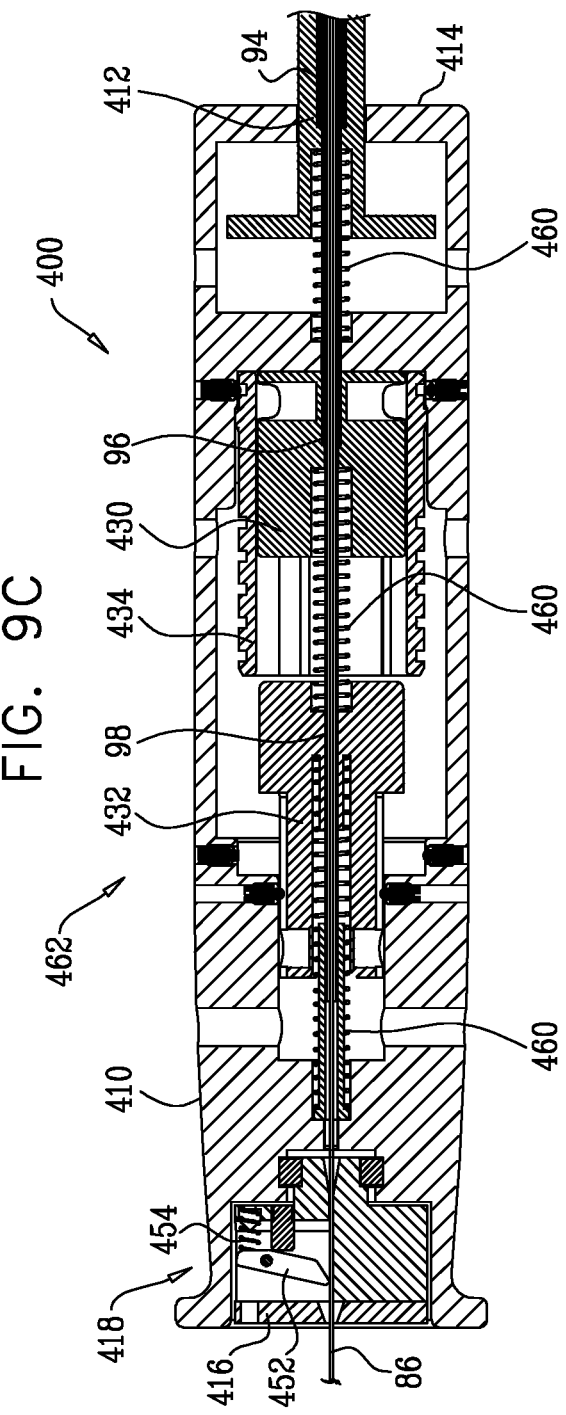

When control knob 434 is positioned in a second position (e.g., a second longitudinal position, such as a distal position, as shown in FIG. 9C), (a) an inner surface of control knob 434 engages intermediate-tube rotation knob 430 but not inner-tube rotation knob 432, leaving knob 432 free to rotate independently of control knob 434, and (b) an outer surface of control knob 434 engages housing 410, rotationally fixing the control knob, and thus intermediate-tube rotation knob 430, to the housing. Handle 400 thus prevents rotation of intermediate tube 96 and outer tube 94, while allowing rotation of inner tube 98. While intermediate tube 96 is prevented from rotating and thus prevents rotation of spool 46, rotation of inner tube 98 causes corresponding rotation of longitudinal member 86, and unscrews the longitudinal member from spool 46, as described hereinabove with reference to FIGS. 6A-B.

Figure 10C:
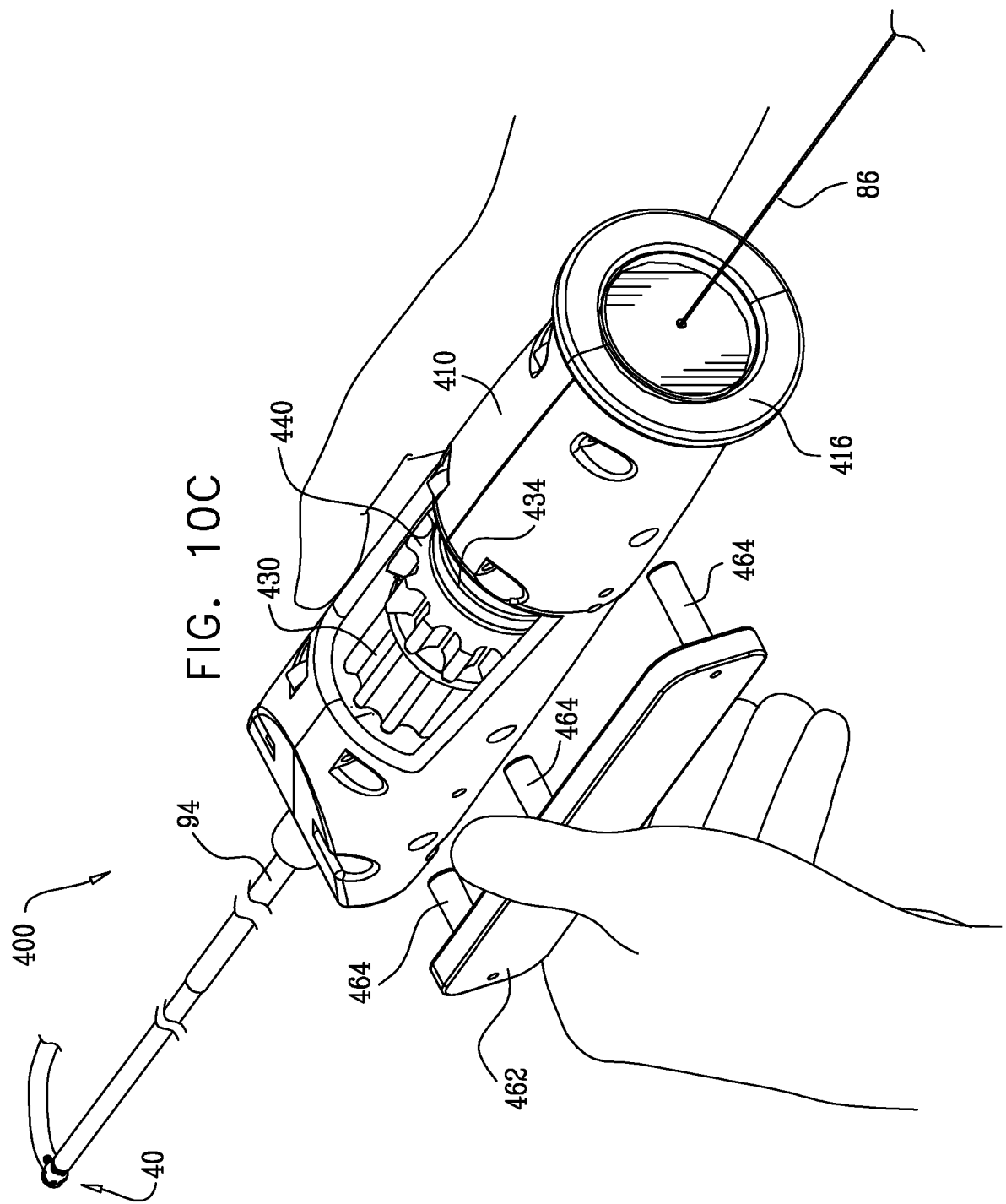
Figure 10D:
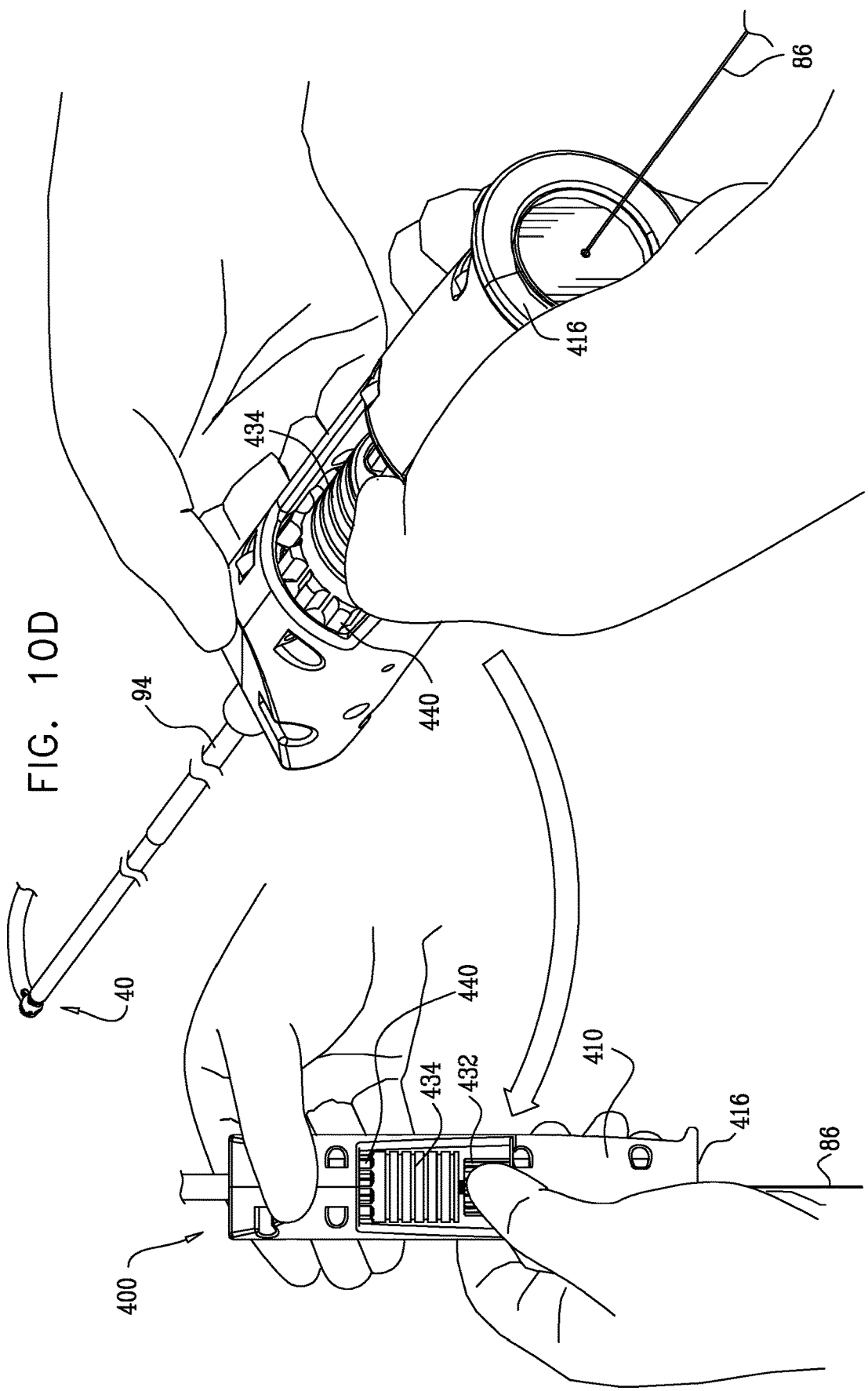

The outer surface of control knob 434 may be shaped so as to define ridges, protrusions 440 (as best seen in FIG. 10D), teeth, or other engagement surfaces, for engaging housing 410, an inner surface of which may define complementary engagement surfaces, such as troughs.

For some applications, when in the first position control knob 434 is closer to proximal end 416 of handle 400, as shown in FIGS. 9A and 9B, and when in the second position control knob 434 is closer to distal end 414 of handle 400, as shown in FIG. 9C.

For some applications, when control knob 434 is positioned in the first longitudinal position (such as a proximal position, as shown in FIGS. 9A, 9B, and 10A-C), the control knob at least partially (typically entirely) covers inner-tube rotation knob 432, thereby preventing access to knob 432 by the surgeon. When control knob 434 is subsequently positioned in the second longitudinal position (such as a distal position, as shown in FIGS. 9C and 10D), the control knob reveals (i.e., no longer covers) inner-tube rotation knob 432. The surgeon thus has convenient access to exposed knob 432, as best seen in FIG. 10D. Housing 410 is also shaped so as to enable such access, as can be seen, for example, in FIG. 10D.

For some applications, control knob 434 does not slide, and instead assumes the first and second positions in response to a non-sliding motion.

For some applications, handle 400 comprises one or more springs 460 that spring-load one or more of tubes 94, 96, and 98, pushing the tubes in a distal direction. Such spring-loading pushes the tubes against the respective elements of contracting mechanism 40, helping the tubes to engage the respective elements of the contracting mechanism, as described hereinabove with reference to FIGS. 6A-B.

For some applications, rotation handle 400 comprises a spring locking mechanism 462, which is configured to assume locking and released states. In the locking state, as shown in FIGS. 9A and 10A-B, the spring locking mechanism prevents one or more of tubes 94, 96, and 98 from advancing in a distal direction. For example, the mechanism may prevent tubes 94, 96, and 98 from advancing distally by preventing distal movement of coupling element 412, intermediate-tube rotation knob 430, and inner-tube rotation knob 432, respectively. Preventing such distal movement holds the springs in relatively compressed states, and prevents the springs from applying force to the tubes. The tubes are more easily coupled to the respective elements of contracting mechanism 40 when the tubes are not spring-loaded.

For some applications, spring locking mechanism 462 comprises one or more pins 464, such as three pins, which are configured to be inserted into housing 410 (e.g., into respective openings in the housing), and, when so inserted, to block the distal motion of respective elements of the rotation handle, such as coupling element 412, intermediate-tube rotation knob 430, and inner-tube rotation knob 432.

In the released state, as shown in FIGS. 9B-C and 10C-D, spring locking mechanism 462 does not prevent tubes 94, 96, and 98 from advancing in the distal direction. For example, the mechanism may not prevent distal movement of coupling element 412, intermediate-tube rotation knob 430, and inner-tube rotation knob 432. Releasing the tubes and/or these elements allows springs 460 to expand, thereby pushing the tubes in a distal direction, as best seen in FIG. 9B. Such spring-loading pushes the tubes against the respective elements of contracting mechanism 40, helping the tubes to engage the respective elements of the contracting mechanism, as described hereinabove with reference to FIGS. 6A-B. Typically, the springs distally advance the tubes 94, 96, and 98 by distally moving coupling element 412, intermediate-tube rotation knob 430, and inner-tube rotation knob 432, respectively, as shown in FIG. 9B.

Reference is still made to FIGS. 10A-D. FIG. 10A shows rotation handle 400 after the tubes have been coupled to respective elements of the handle, as described above, and as the surgeon pulls longitudinal member 86 through handle 400 and out of proximal end 416 thereof. As described above, longitudinal member coupling assembly 418 may be provided to prevent withdrawal of the longitudinal member in a distal direction after the longitudinal member has been drawn sufficiently through the handle. FIG. 10A also shows spring locking mechanism 462 in its locking state.

FIG. 10B shows rotation handle 400 after the initial coupling of the tubes to contracting mechanism 40. Because spring locking mechanism 462 is still in its locking state, springs 460 have not yet distally pushed the tubes, so the tubes have not yet fully engaged respective elements of the contracting mechanism.

FIG. 10C shows rotation handle 400 after spring locking mechanism 462 has been released to its released state. This release allows springs 460 to distally push the tubes against respective elements of contracting mechanism 40 until the tubes fully engage respective elements of the contracting mechanism. Control knob 434 is shown in its first (proximal) longitudinal position, in which an inner surface of the control knob engages both knobs 430 and 432 (not visible in FIG. 10C). Rotation of the control knob thus rotates both intermediate-tube rotation knob 430 (and thus intermediate tube 96) and inner-tube rotation knob 432 (and thus inner tube 98). The rotation of intermediate tube 96 rotates spool 46, as described hereinabove with reference to FIGS. 6A-B. The rotation of inner tube 98 rotates longitudinal member 86 at the same rate as the spool is rotated, such that longitudinal member 86 remains screwed into the spool.

FIG. 10D shows rotation handle 400 after control knob 434 has been is positioned in its second (distal) longitudinal position, in which (a) an inner surface of control knob 434 engages intermediate-tube rotation knob 430 (not visible in FIG. 10D) but not inner-tube rotation knob 432 (visible in FIG. 10D), leaving knob 432 free to rotate independently of control knob 434, and (b) an outer surface of control knob 434 engages housing 410, rotationally fixing the control knob, and thus intermediate-tube rotation knob 430, to the housing. Handle 400 thus prevents rotation of intermediate tube 96 and outer tube 94, while allowing rotation of inner tube 98. While intermediate tube 96 is prevented from rotating and thus prevents rotation of spool 46, rotation of inner tube 98 causes corresponding rotation of longitudinal member 86, and unscrews the longitudinal member from spool 46, as described hereinabove with reference to FIGS. 6A-B.

Reference is now made to FIGS. 11A-I, which are schematic illustrations of a procedure for implanting annuloplasty ring 22 to repair a mitral valve 130, in accordance with an application of the present invention. The procedure is typically performed with the aid of imaging, such as fluoroscopy, transesophageal echo, and/or echocardiography.

Figure 11A:
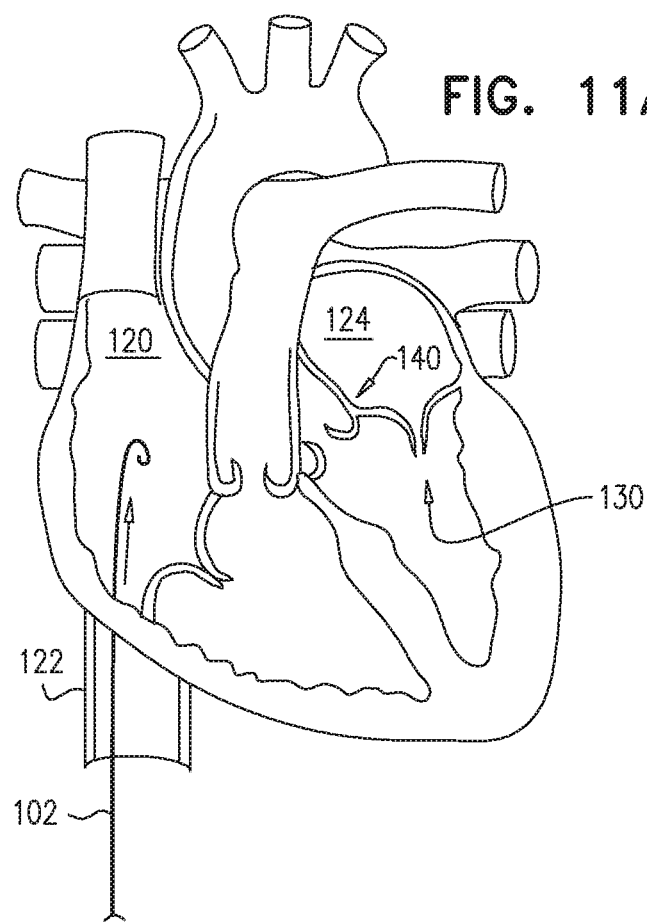

The procedure typically begins by advancing a semi-rigid guidewire 102 into a right atrium 120 of the patient, as shown in FIG. 11A.

Figure 11B:
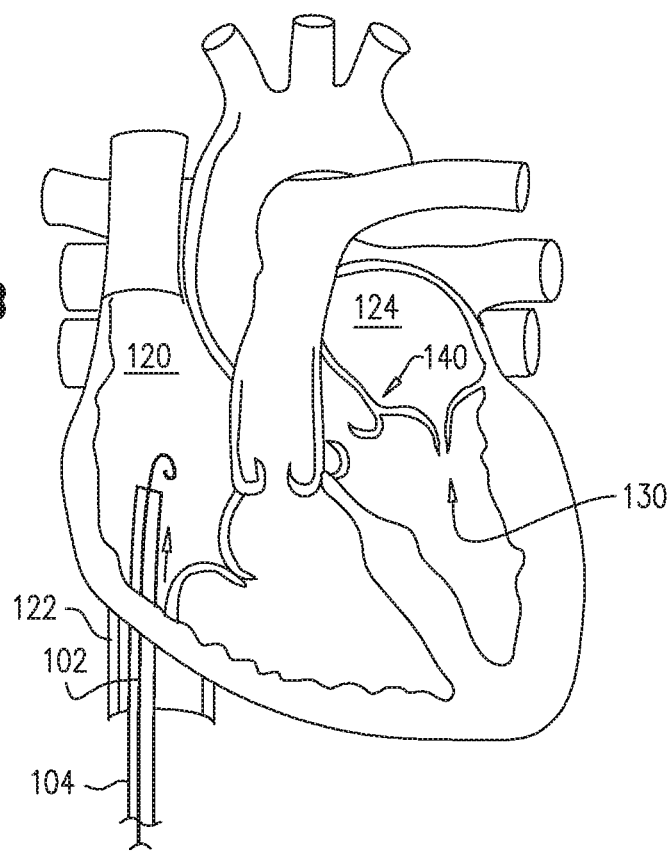
Figure 11C:
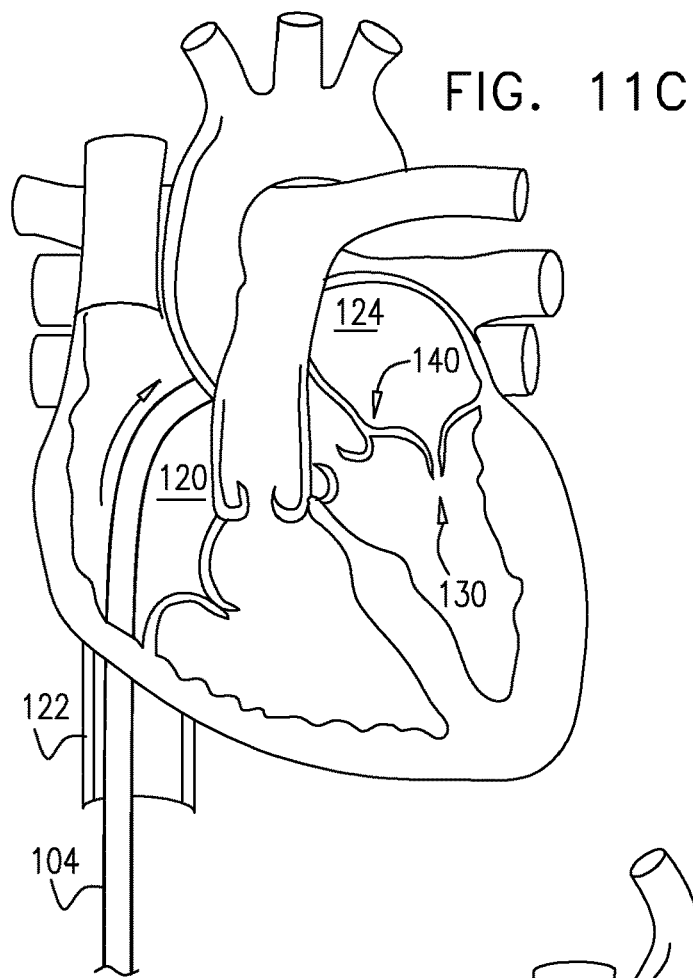

As show in FIG. 11B, guidewire 102 provides a guide for the subsequent advancement of a sheath 104 therealong and into the right atrium. Once sheath 104 has entered the right atrium, guidewire 102 is retracted from the patient's body. Sheath 104 typically comprises a 14-20 F sheath, although the size may be selected as appropriate for a given patient.

Sheath 104 is advanced through vasculature into the right atrium using a suitable point of origin typically determined for a given patient. For example:

- sheath 104 may be introduced into the femoral vein of the patient, through an inferior vena cava 122, into right atrium 120, and into a left atrium 124 transseptally, typically through the fossa ovalis;
- sheath 104 may be introduced into the basilic vein, through the subclavian vein to the superior vena cava, into right atrium 120, and into left atrium 124 transseptally, typically through the fossa ovalis; or
- sheath 104 may be introduced into the external jugular vein, through the subclavian vein to the superior vena cava, into right atrium 120, and into left atrium 124 transseptally, typically through the fossa ovalis.

For some applications of the present invention, sheath 104 is advanced through an inferior vena cava 122 of the patient (as shown) and into right atrium 120 using a suitable point of origin typically determined for a given patient.

Sheath 104 is advanced distally until the sheath reaches the interatrial septum.

Figure 11D:
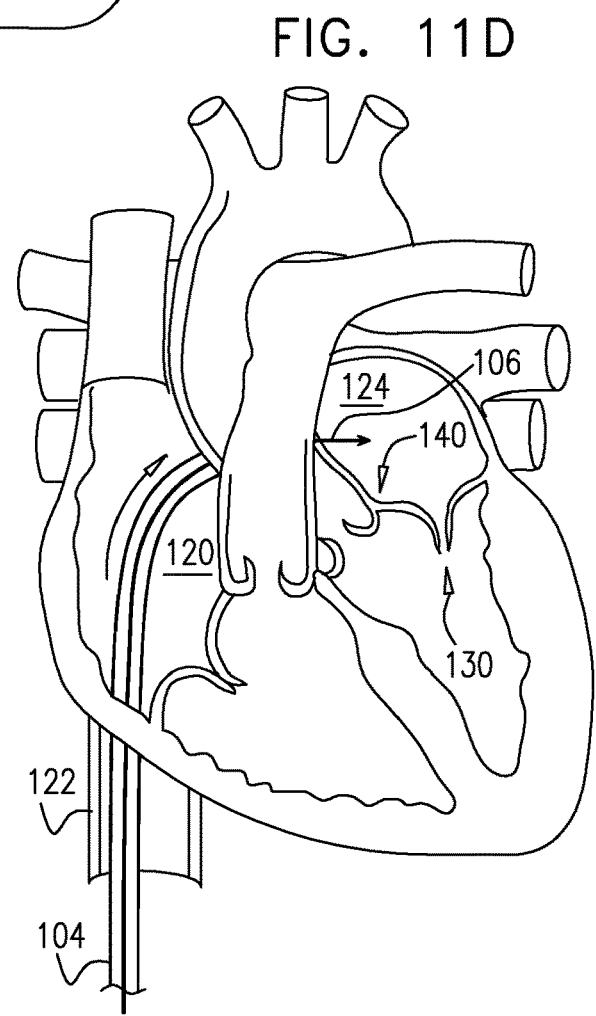

As shown in FIG. 11D, a resilient needle 106 and a dilator (not shown) are advanced through sheath 104 and into the heart. In order to advance sheath 104 transseptally into left atrium 124, the dilator is advanced to the septum, and needle 106 is pushed from within the dilator and is allowed to puncture the septum to create an opening that facilitates passage of the dilator and subsequently sheath 104 therethrough and into left atrium 124. The dilator is passed through the hole in the septum created by the needle. Typically, the dilator is shaped to define a hollow shaft for passage along needle 106, and the hollow shaft is shaped to define a tapered distal end. This tapered distal end is first advanced through the hole created by needle 106. The hole is enlarged when the gradually increasing diameter of the distal end of the dilator is pushed through the hole in the septum.

Figure 11E:
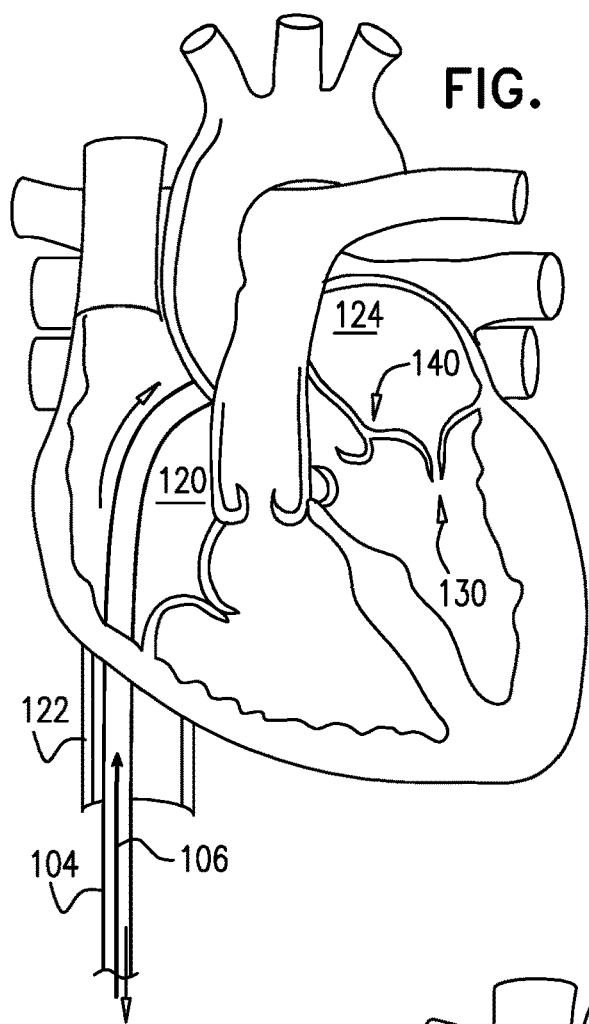

The advancement of sheath 104 through the septum and into the left atrium is followed by the extraction of the dilator and needle 106 from within sheath 104, as shown in FIG. 11E.

Figure 11F:
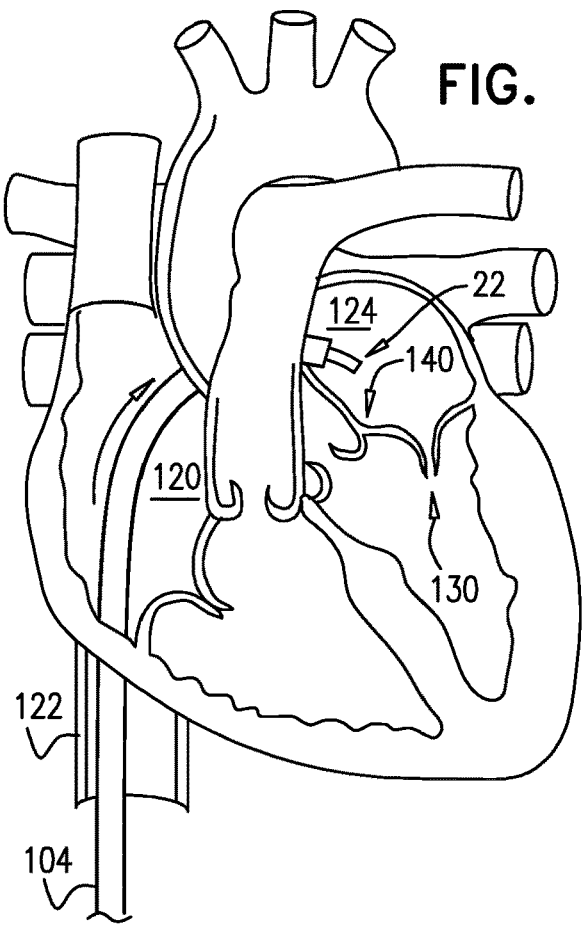

As shown in FIG. 11F, annuloplasty ring 22 (with anchor deployment manipulator 24 therein) is advanced through sheath 104 into left atrium 124.

As shown in FIG. 11G, distal end 51 of sleeve 26 is positioned in a vicinity of a left fibrous trigone 142 of an annulus 140 of mitral valve 130. (It is noted that for clarity of illustration, distal end 51 of sleeve 26 is shown schematically in the cross-sectional view of the heart, although left trigone 142 is in reality not located in the shown cross-sectional plane, but rather out of the page closer to the viewer.) Alternatively, the tip is positioned in a vicinity of a right fibrous trigone 144 of the mitral valve (configuration not shown). Further alternatively, the distal tip of the sleeve is not positioned in the vicinity of either of the trigones, but is instead positioned elsewhere in a vicinity of the mitral valve, such as in a vicinity of the anterior or posterior commissure. For some applications, outer tube 66 of anchor deployment manipulator 24 is steerable, as is known in the catheter art, while for other applications, a separate steerable tube is provided, as described hereinbelow with reference to FIG. 15 and FIG. 16. In either case, the steering functionality typically allows the area near the distal end of the deployment manipulator to be positioned with six degrees of freedom. Once positioned at the desired site near the selected trigone, deployment manipulator 24 deploys a first anchor 38 through the wall of sleeve 26 into cardiac tissue near the trigone.

As shown in FIG. 11H, deployment manipulator 24 is repositioned along annulus 140 to another site selected for deployment of a second anchor 38. Typically, the first anchor is deployed most distally in the sleeve (generally at or within a few millimeters of the distal tip of the sleeve), and each subsequent anchor is deployed more proximally, such that the sleeve is gradually pulled off (i.e., withdrawn from) the deployment manipulator in a distal direction during the anchoring procedure. The already-deployed first anchor 38 holds the anchored end of sleeve 26 in place, so that the sleeve is drawn from the site of the first anchor towards the site of the second anchor. Typically, as the sleeve is pulled off (i.e., withdrawn from) the deployment manipulator, the deployment manipulator is moved generally laterally along the cardiac tissue, as shown in FIG. 11H. Deployment manipulator 24 deploys the second anchor through the wall of the sleeve into cardiac tissue at the second site. Depending on the tension applied between the first and second anchor sites, the portion of sleeve 26 therebetween may remain tubular in shape, or may become flattened, which may help reduce any interference of the ring with blood flow.

For some applications, in order to provide the second and subsequent anchors, anchor driver 68 is withdrawn from the subject's body via sheath 104 (typically while leaving outer tube 66 of the deployment manipulator in place in the sleeve), provided with an additional anchor, and then reintroduced into the subject's body and into the outer tube. Alternatively, the entire deployment manipulator, including the anchor driver, is removed from the body and subsequently reintroduced upon being provided with another anchor. Further alternatively, deployment manipulator 24 is configured to simultaneously hold a plurality of anchors, and to deploy them one at a time at the selected sites.

As shown in FIG. 11I, the deployment manipulator is repositioned along the annulus to additional sites, at which respective anchors are deployed, until the last anchor is deployed in a vicinity of right fibrous trigone 144 (or left fibrous trigone 142 if the anchoring began at the right trigone). Alternatively, the last anchor is not deployed in the vicinity of a trigone, but is instead deployed elsewhere in a vicinity of the mitral valve, such as in a vicinity of the anterior or posterior commissure.

As described hereinabove with reference to FIGS. 1A and 1B and/or FIGS. 6A-8, rotation tool 80 or anchor driver 68 of deployment manipulator 24 is used to rotate spool 46 of contracting mechanism 40, in order to tighten ring 22. (For clarity of illustration, contracting member 30 of ring 22, although provided, is not shown in FIGS. 11A-I.) For some applications, rotation handle 400 is used to tighten the ring, such as described hereinabove with reference to FIGS. 9A-C and/or 10A-D. Alternatively, another technique is used to tighten the ring, such as described hereinabove.

For some applications, sleeve 26 is filled with a material (e.g., polyester, polytetrafluoroethylene (PTFE), polyethylene terephthalate (PET), or expanded polytetrafluoroethylene (ePTFE)) after being implanted. The material is packed within at least a portion, e.g., 50%, 75%, or 100%, of the lumen of sleeve 26. The filler material functions to prevent (1) formation within the lumen of sleeve 26 of clots or (2) introduction of foreign material into the lumen which could obstruct the sliding movement of contracting member 30.

For some applications, proximal end 49 of sleeve 26 is closed upon completion of the implantation procedure. Alternatively, the proximal end of the sleeve may have a natural tendency to close when not held open by deployment manipulator 24.

Figure 12:
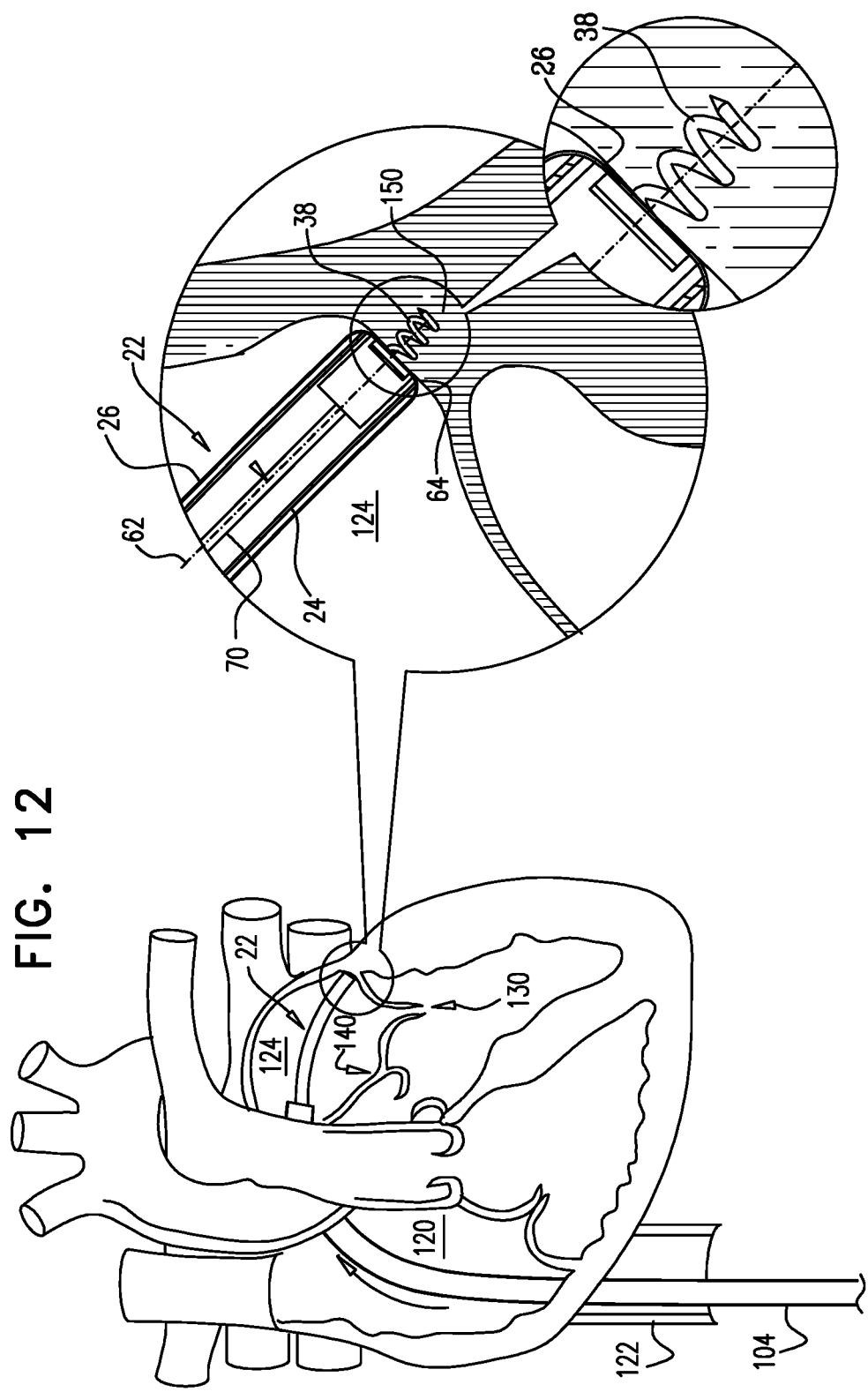
FIG. 12 is a schematic illustration of the deployment of an anchor into cardiac tissue, in accordance with an application of the present invention.

Reference is made to FIG. 12, which is a schematic illustration of the deployment of one of anchors 38 into cardiac tissue, in accordance with an application of the present invention. For these applications, one or more (such as all) of anchors 38 are deployed from left atrium 124, through tissue of the atrial wall, and into tissue of an upper region of the ventricular wall 150 near the atrium. Because the tissue of the upper region of ventricular wall is thicker than that of the atrial wall, deploying the anchors into the upper region of the ventricular wall generally provides more secure anchoring. In addition, because the anchors are not deployed laterally through the atrial wall, the risk of perforating the atrial wall is reduced.

Annuloplasty ring 22 may be advanced toward annulus 140 in any suitable procedure, e.g., a transcatheter procedure, a percutaneous procedure, a minimally invasive procedure, or an open heart procedure (in which case one or more elements of system 20 are typically rigid). Regardless of the approach, the procedure typically includes the techniques described hereinabove with reference to FIGS. 11G-I and 12.

For some applications, following initial contraction of annuloplasty ring 22 during the implantation procedure, the ring may be further contracted or relaxed at a later time after the initial implantation, such as between several weeks and several months after the initial implantation. Using real-time monitoring, tactile feedback and optionally in combination with fluoroscopic imaging, a rotation tool or anchor driver 68 of deployment manipulator 24 is reintroduced into the heart and used to contract or relax annuloplasty ring 22.

Reference is now made to FIG. 13, which is a schematic illustration of system 10 comprising a flexible pusher element 200, in accordance with an application of the present invention. Pusher element 200 aids with accurately positioning successive anchors 38 during an implantation procedure, such as described hereinabove with reference to FIGS. 11H and 11I. For some applications, pusher element 200 is positioned partially within tube 66 of deployment manipulator 24 such that a distal portion 204 of pusher element 200 extends distally out of tube 66, through an opening 206 in a vicinity of a distal end of the tube (e.g., that is within 3 mm of the distal end, such as within 2 mm of the distal end). A proximal portion 202 of pusher element 200 passes through outer tube 66 from opening 206 to the proximal end of tube 66. Opening 206 is provided either through a wall of the tube (as shown in FIG. 13), or through the distal end of the tube (configuration not shown). Alternatively, pusher element 200 is positioned within sleeve 26, but outside of tube 66 (configuration not shown). Typically, the pusher element is elongated, and is as least as long as sleeve 26.

Pusher element 200 helps move the distal end of deployment manipulator 24 from a first site of the annulus at which the deployment manipulator has already deployed a first anchor (e.g., anchor 38A in FIG. 13) to a second site for deployment of a second anchor (e.g., anchor 38B), in a direction indicated schematically by an arrow 210. Pusher element 200 is pushed distally out of opening 206 of tube 66, so that a distal end 212 of pusher element 200 engages and pushes against an interior surface of sleeve 26, in a direction indicated schematically by an arrow 214. The interior surface of the sleeve may be distal end 51 of the sleeve (as shown), or the wall of the sleeve at a location between distal end 51 and opening 206 (not shown). As a result, the distal end of deployment manipulator 24 moves in the opposite direction, i.e., as indicated by arrow 210, toward a subsequent anchoring site. The movement in the direction of arrow 210 is generally along a line or curve defined by the portion of pusher element 200 already extended between the anchors that have already been deployed.

For some applications, as deployment manipulator 24 is positioned at successive deployment sites of the cardiac tissue, pusher element 200 is extended respective distances through opening 206, each of which distances is successively greater. For other applications, after deployment manipulator 24 is positioned at each successive deployment site, the pusher element is pulled back in a proximal direction, and again extended a desired distance in a distal direction, such that the pusher element pushes again the wall of the sleeve (at a different location on the wall for each successive relocation of deployment manipulator 24).

This technique thus aids in locating each subsequent anchoring site for deployment manipulator 24. The pusher element may also help control the distance between adjacent anchoring sites, because they surgeon may push the pusher element a known distance after deploying each anchor.

Pusher element 200 typically comprises a strip, wire, ribbon, or band, and has a cross-section that is circular, elliptical, or rectangular. Pusher element 200 typically comprises a flexible and/or superelastic material, such as a metal such as nitinol, stainless steel, or cobalt chrome. Distal end 212 of pusher element 200 is dull, so that it does not penetrate sleeve 26. For example, the distal end may be folded back, as shown in FIG. 13.

FIG. 14 is a schematic illustration of a pusher tube 250 applied to proximal end 49 of sleeve 26, in accordance with an application of the present invention. As shown in FIG. 14, outer tube 66 is removably positioned partially within the lumen of sleeve 26, such that outer tube 66 extends out of proximal end 49 of sleeve 26 (proximal end 49 can be seen in FIG. 1B). Pusher tube 250 is configured to pass over outer tube 66, such that a distal end of the pusher tube comes in contact with proximal end 49 of sleeve 26. The pusher tube 250 is held in place against proximal end 49 of sleeve 26, typically by an external control handle, such as external control handle 346, described hereinbelow with reference to FIG. 17, or external control handle 490, described hereinbelow with reference to FIG. 19. As the sleeve is pulled off (i.e., withdrawn from) outer tube 66 of the deployment manipulator in a distal direction, pusher tube 250 pushes sleeve 26 distally with respect to outer tube 66, helping withdraw the sleeve from the outer tube. If the pusher tube were not provided, the wall of sleeve 26 might snag on outer tube 66 (as mentioned above, the sleeve may comprise braided or woven fabric). In addition, if such snagging occurs, gentle pushing with the pusher tube in the distal direction may help free the snag. For some applications, the techniques of this application are practiced in combination with those of the application described hereinbelow with reference to FIG. 17.

FIG. 15 is a schematic illustration of system 10 comprising a steerable tube 300, in accordance with an application of the present invention. For this application, outer tube 66 of deployment manipulator 24 is not steerable. Instead, to provide steering functionality, deployment manipulator 24 comprises a separate steering tube 300, which is positioned around at least a portion of outer tube 66. Outer tube 66, because it does not provide this steering functionality, may have a smaller diameter than in the application described hereinabove with reference to FIG. 3. Because outer tube 66 has a smaller diameter, sleeve 26 may also have a smaller diameter than in the application described hereinabove with reference to FIG. 3. For some applications, the techniques of this application are practiced in combination with those of the application described hereinabove with reference to FIG. 14. (Although in the application described with reference to FIG. 15, system 10 typically comprises contracting member 30, for clarity of illustration the contracting member is not shown in the figure.)

FIG. 16 is a schematic illustration of system 10 comprising a steerable tube 320, in accordance with an application of the present invention. For this application, outer tube 66 of deployment manipulator 24 is not steerable. Steering functionality is instead provided by separate steering tube 320, which is positioned around at least a portion of shaft 70 of anchor driver 68, and within outer tube 66. For some applications, the techniques of this application are practiced in combination with those of the application described hereinabove with reference to FIG. 14. (Although in the application described with reference to FIG. 16, system 10 typically comprises contracting member 30, for clarity of illustration the contracting member is not shown in the figure.)

Figure 17:
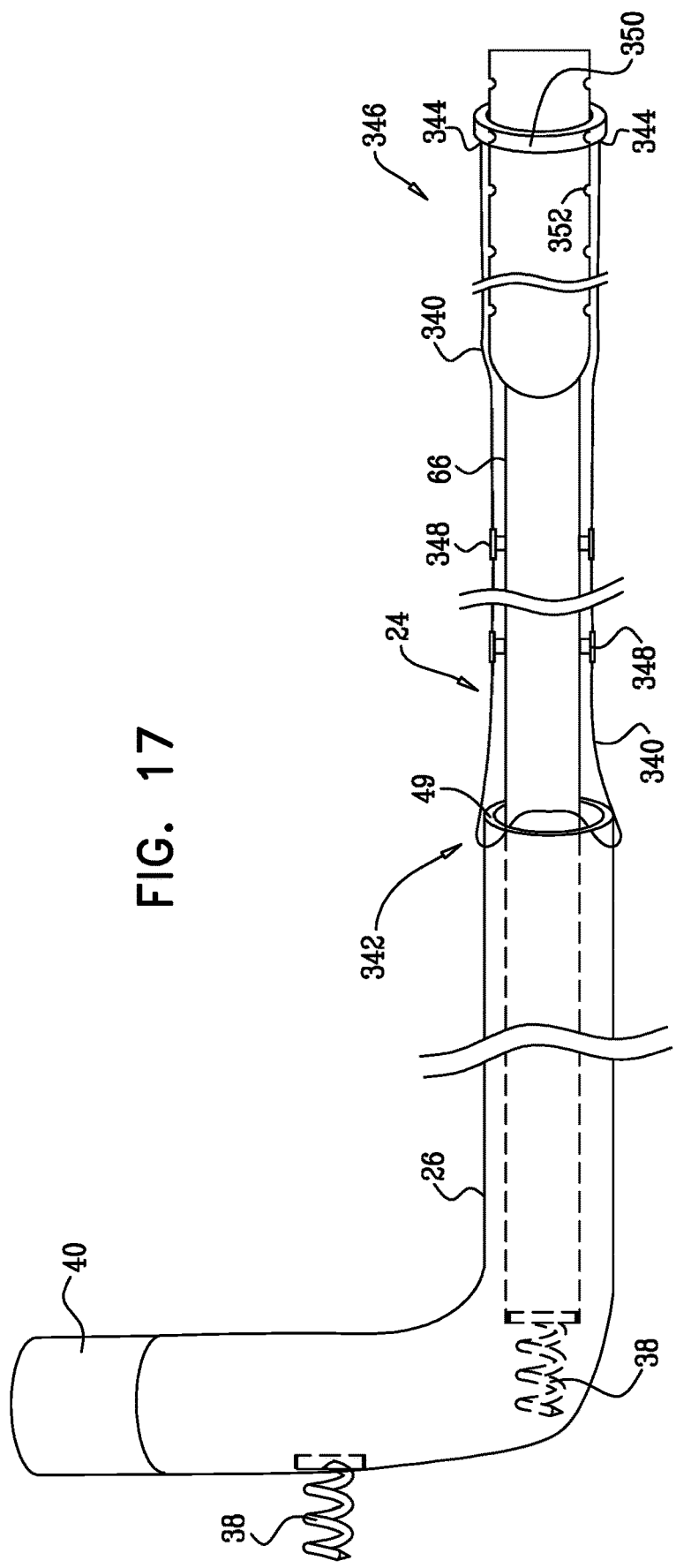
FIG. 17 is a schematic illustration of the system of FIGS. 1-4 comprising a pulling wire, in accordance with an application of the present invention.

FIG. 17 is a schematic illustration of system 10 comprising a pulling wire 340, in accordance with an application of the present invention. A distal portion 342 of pulling wire 340 is coupled to proximal end 49 of sleeve 26, such as by passing through one or more holes near the proximal end. One or more proximal portions 344 of the pulling wire are coupled to an external control handle 346 of system 10, which is manipulated by the surgeon outside of the subject's body. External control handle 346 is coupled to a proximal portion of outer tube 66, such as a proximal end of the outer tube. Optionally, a portion of deployment manipulator 24 (e.g., a portion of outer tube 66) which is never inserted in sleeve 26 comprises one or more coupling elements 348, such as loops or tubes, through which pulling wire 340 passes in order to hold the pulling wire close to the external surface of the deployment manipulator. (Although in the application described with reference to FIG. 17, system 10 typically comprises contracting member 30, for clarity of illustration the contracting member is not shown in the figure.)

Pulling wire 340 holds sleeve 26 surrounding deployment manipulator 24. The pulling wire is released in a distal direction as sleeve 26 is withdrawn from outer tube 66 of deployment manipulator 24 in a distal direction. The release of the sleeve allows the sleeve to gradually be withdrawn from the outer tube 66 of deployment manipulator 24, in a controlled manner. In FIG. 17, the sleeve is shown partially withdrawn from outer tube 66, including the portion of the sleeve through which one of anchors 38 has been deployed.

For some applications, control handle 346 is configured to release pulling wire 340 incrementally in the distal direction, such that each time the wire is further released by respective set distances (typically, the distances are equal to one another). As a result, the sleeve is withdrawn from outer tube 66 of the deployment manipulator by this set distance (or respective distances), and subsequently-deployed anchors are approximately this set distance (or respective set distances) apart from one another. For example, the set distances may be between 2 mm and 15 mm, such as 4.5 mm. For some applications, the handle comprises a control ring 350 that is coupled to proximal portions 344 of the wire, and removably engages slots 352 on the handle that are spaced apart by this set distance. The slots thus set discrete positions for the ring and the wire. For some applications, control handle 346 is configured to allow control ring 350 to move only in the distal direction during a surgical procedure. Upon completion of the implantation procedure, in order to detach the pulling wire from the sleeve, one end of the wire may be cut or released, and the wire detached from the sleeve by pulling on the other end of the wire.

FIGS. 18A and 18B are schematic illustrations of another configuration of pusher tube 250, described hereinabove with reference to FIG. 14, in accordance with an application of the present invention. As described hereinabove with reference to FIG. 14, pusher tube 250 passes over outer tube 66, and pushes gently in a distal direction on proximal end 49 of sleeve 26. The pusher tube is held in place against proximal end 49 of sleeve 26, typically by an external control handle, such as external control handle 346, described hereinabove with reference to FIG. 17. As the sleeve is pulled off (i.e., withdrawn from) outer tube 66 of the deployment manipulator, pusher tube 250 pushes sleeve 26 distally with respect to outer tube 66, helping withdraw the sleeve from the outer tube. If the pusher tube were not provided, the wall of sleeve 26 might snag on outer tube 66 (as mentioned above, the sleeve may comprise braided or woven fabric). In addition, if such snagging occurs, gentle pushing with the pusher tube in the distal direction may help free the snag.

In the configuration shown in FIG. 18A, pusher tube 250 comprises one or more coupling elements 456 (such as exactly one coupling element or exactly two coupling elements). The coupling elements are configured to removably couple proximal end 49 of sleeve 26 to a distal end 458 of pusher tube 250, thereby allowing sleeve 26 from moving distally with respect to outer tube 66 of deployment manipulator 24 only to the extent that pusher tube 250 is released in the distal direction, such as using external control handle 490, described hereinbelow with reference to FIG. 19.

For some applications, coupling elements 456 have a natural tendency to flex inwards (toward a central longitudinal axis of sleeve 26 that passes through the proximal end of the sleeve). Outer tube 66, when positioned within the sleeve in a vicinity of the coupling elements, pushes the coupling elements outwards (away from the central longitudinal axis), causing the coupling elements to engage the sleeve. For example, the coupling elements may be curved to define outwardly-directed ends that push against or pierce the sleeve. Such pushing against or piercing engages the sleeve, which, as mentioned above, may comprise braided or woven fabric.

FIG. 18B shows sleeve 26 released from coupling elements 456. Proximal withdrawal of outer tube 66 from sleeve 26 (into or through pusher tube 250) allows coupling elements 456 to assume their natural inwardly-flexed position, thereby releasing sleeve 26 from the coupling elements, and decoupling the sleeve from the pusher tube. As described hereinabove, sleeve 26 is gradually pulled off (i.e., withdrawn from) deployment manipulator 24, including outer tube 66, in a distal direction during the anchoring procedure. Outer tube 66 of deployment manipulator 24 is proximally withdrawn completely from the sleeve at the conclusion of the anchoring procedure. The flexing of the coupling elements releases the sleeve at the conclusion of the procedure.

FIG. 19 is a schematic illustration of system 10 comprising an external control handle 490, in accordance with an application of the present invention. External control handle 490 is configured to be used with pusher tube 250, as described hereinabove with reference to FIGS. 14 and/or 18A-B. The handle is manipulated by the surgeon outside of the subject's body. External control handle 490 is coupled to a proximal portion of outer tube 66, such a proximal end of the outer tube. For some applications, coupling elements 456 of pusher tube 250 couple proximal end 49 of sleeve 26 to distal end 458 of pusher tube 250, as described hereinabove with reference to FIGS. 18A-B (proximal end 49 can be seen in FIG. 18B). A proximal end of pusher tube 250 is coupled to handle 490. (Although in the application described with reference to FIG. 19, system 10 typically comprises contracting member 30, for clarity of illustration the contracting member is not shown in the figure.)

External control handle 490 is configured to release pusher tube 250 in a distal direction as sleeve 26 is withdrawn from outer tube 66 of deployment manipulator 24. The release of pusher tube 250 releases sleeve 26, and allows the sleeve to gradually be withdrawn from outer tube 66, in a controlled manner. In FIG. 19, the sleeve is shown partially withdrawn from outer tube 66, including the portion of the sleeve through which one of anchors 38 has been deployed.

For some applications, control handle 490 is configured to release pusher tube 250 incrementally in the distal direction, such that each time the pusher tube is further released by respective set distances (typically, the distances are equal to one another). As a result, the sleeve is withdrawn from outer tube 66 of the deployment manipulator by this set distance (or respective distances), and subsequently-deployed anchors are approximately this set distance (or respective distances) apart from one another. For example, the set distances may be between 2 mm and 15 mm, such as 4.5 mm. For some applications, the handle comprises control ring 350 that is coupled to a proximal end of pusher tube 250, and removably engages slots 352 on the handle that are spaced apart by this set distance. The slots thus set discrete positions for the ring and the pusher tube. For some applications, control handle 490 is configured to allow control ring 350 to move only in the distal direction during a surgical procedure. For some applications, upon completion of the implantation procedure, in order to detach the pusher tube from the sleeve, outer tube 66 of deployment manipulator 24 is proximally withdrawn completely from the sleeve, thereby causing the coupling elements to release the sleeve, such as described hereinabove with reference to FIG. 18B.

Although annuloplasty ring 22 has been described hereinabove as comprising a partial annuloplasty ring, for some applications of the present invention, the ring instead comprises a full annuloplasty ring.

Reference is made to FIGS. 20A-E, which are schematic cross-sectional and isometric illustrations of a configuration of driver head 72 of anchor driver 68, in accordance with an application of the present invention.

Anchor driver 68 is described hereinabove, for example, with reference to FIG. 2. Driver head 72 comprises an inner mating component 470, which is coupled to a distal end 472 of flexible shaft 70, such as by welding, such that inner mating component 470 is rotationally fixed to shaft 70. (In this context, "inner" means closer to a longitudinal axis 473 of driver head 72.) As shown in FIGS. 20B and 20D, a distal end of inner mating component 470 is shaped so as to define one or more (e.g., two) mechanical coupling elements, such as protrusions 474. Coupling head 74 of anchor 38 is shaped so as to define corresponding mating elements, such as slots 476, also shown in FIG. 20B. Before implantation of anchor 38, coupling head 74 is removably coupled to inner mating component 470 by the coupling and mating elements.

Driver head 72 further comprises an outer element 478, which at least partially surrounds inner mating component 470 and extends in a distal direction beyond a distal end of inner mating component 470. (In this context, "outer" means further from longitudinal axis 473 of driver head 72.) Typically, outer element 478 is free to rotate with respect to inner mating component 470. Outer element 478 is typically longitudinally fixed to the inner mating component. For example, the inner mating component may be shaped so as to define at least one lateral protrusion 480, and the outer element may be shaped to define at least one corresponding recess 482. Alternatively, one or more of inner mating component 470, distal end 472 of flexible shaft 70, and outer element 478 are welded together, or comprise a single element.

An outer surface of coupling head 74 of anchor 38 is typically shaped so as to define a screw thread 484. The screw thread is initially screwed into a flexible ring 486 that is coupled to an inner surface of outer element 478. The ring is sized to tightly engage the screw thread. The ring may comprise, for example, silicone, rubber, or a springy metal. For some applications, a distal portion of coupling head 74 (such as the portion that defines screw thread 484) is conical.

During deployment of anchor 38 into tissue, such as described hereinabove with reference to FIGS. 2, 3, 11G-H, 12, 13, 14, 15, and/or 16, rotation of shaft 70 and inner mating component 470 causes corresponding rotation of anchor 38. As tissue coupling element 76 of anchor 38 rotates, the tissue coupling element screws itself into the tissue, thereby advancing itself in a distal direction (to the right in FIG. 20C) into the tissue. This rotation and distal advancement of the anchor unscrews screw thread 484 from flexible ring 486, and, at the same time, separates the mating elements of coupling head 74 of the anchor from the coupling elements of inner mating component 470 of driver head 72.

This configuration of driver head 72 and anchor 38 thus enables the anchor to self-disconnect from the driver head.

For some applications, anchor 38 is coupled to driver head 72 (typically during manufacture) by:
 aligning protrusions 474 with slots 476;
 holding inner mating component 470 and tissue coupling element 76 rotationally stationary; and
 rotating outer element 478, which causes flexible ring 486 to screw in screw thread 484 of coupling head 74. As the coupling head is screwed into driver head 72, protrusions 474 enter slots 476.

Figure 21:
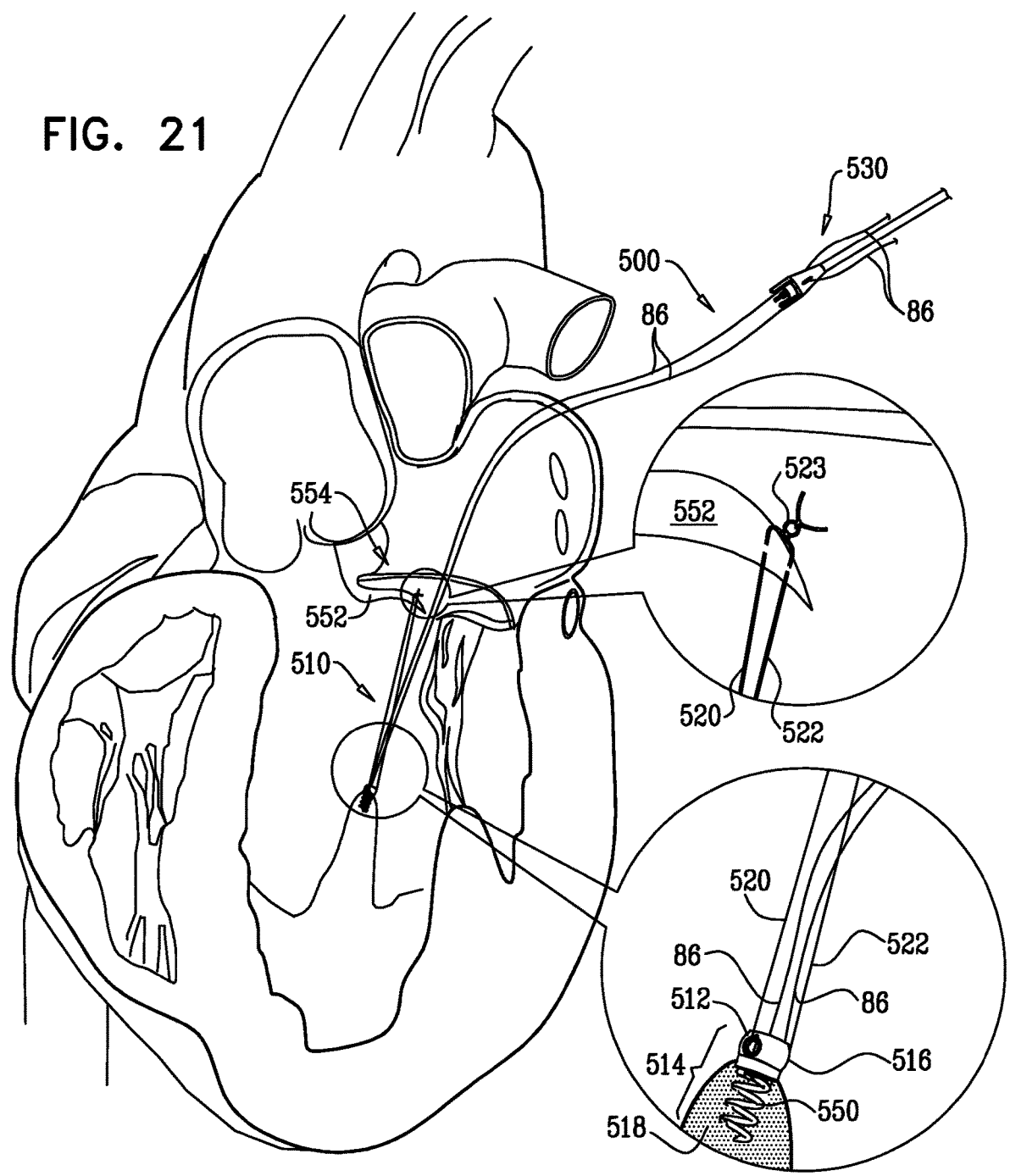
FIG. 21 is a schematic illustration of an implant structure comprising repair chords, in accordance with an application of the present invention.

Reference is now made to FIG. 21, which is a schematic illustration of an implant structure 500 comprising repair chords 510, in accordance with an application of the present invention. In this application, repair chords 510 function as artificial chordae tendineae, and comprise one or more longitudinal members 520 and 522, e.g., sutures, wires, or elongate tensioning coils, which are coupled at respective first end portions thereof to a contracting mechanism 512. Respective second end portions of the longitudinal members are coupled (e.g., tied, sutured, clipped, or otherwise fastened) to a second portion of tissue which faces and surrounds the ventricle, such as a leaflet 552 of an atrioventricular valve 554 (e.g., a mitral valve or a tricuspid valve). Longitudinal members 520 and 522 are knotted together using at least one suture knot 523, and excess portions of longitudinal members 520 and 522 are cut away from the knot. Alternatively, any suitable anchor may be used instead of the knot. For example, longitudinal member 520 may comprise a male clip at its free end and longitudinal member 522 may comprise a female clip at its free end. In this case, longitudinal members 520 and 522 are clipped at their free ends to the leaflet. For some applications, anchors or clips may be used that are described in U.S. patent application Ser. No. 12/548,991, filed Aug. 27, 2009, which published as US Patent Application Publication 2010/0161042 and is incorporated herein by reference, such as with reference to one or more of FIGS. 9A-18D and 22A-23I thereof.

Implant structure 500 comprises a contracting mechanism assembly 514, which comprises contracting mechanism 512 and a tissue anchor 550. The tissue anchor facilitates implantation of the contracting mechanism assembly in a first portion of tissue of the heart which faces and surrounds the ventricular lumen, such as a papillary muscle 518. Tissue anchor 550 is shown as a helical anchor by way of illustration and not limitation, and may comprise staples, clips, spring-loaded anchors, or other tissue anchors known in the art. Alternatively, contracting mechanism assembly 514 does not include tissue anchor 50 and is, instead, sutured to a portion of tissue of a ventricle wall which faces a ventricular lumen of a heart of a patient.

For some applications, contracting mechanism 512 comprises a rotatable structure, such as a spool (not visible in FIG. 21, but typically similar to spool 46, described hereinabove with reference to FIGS. 5A-B, 6A-B, 7, and 8), and, typically, a housing 516, which houses the spool. First end portions of the longitudinal members are coupled to contracting mechanism 512, typically to spool 46.

Implant structure 500 comprises one or more longitudinal members 86, which are coupled to contracting mechanism 512, such as to housing 516 or to the spool. A rotation tool 530 is configured to pass over longitudinal members 86, engage the spool of contracting mechanism 512, and rotate the spool, thereby tightening the contracting mechanism, and shortening and tensioning longitudinal members 520 and 522.

For some applications, implant structure 500 utilizes techniques described hereinabove with reference to FIGS. 5A-B, 6A-B, 7, 8, 9A-C, and/or 10A-D. For some applications, implant structure 500 utilizes techniques described in U.S. patent application Ser. No. 12/548,991, filed Aug. 27, 2009, which is incorporated herein by reference, such as with reference to one or more of FIGS. 3-18D and 22A-23I thereof.

Figure 22A:
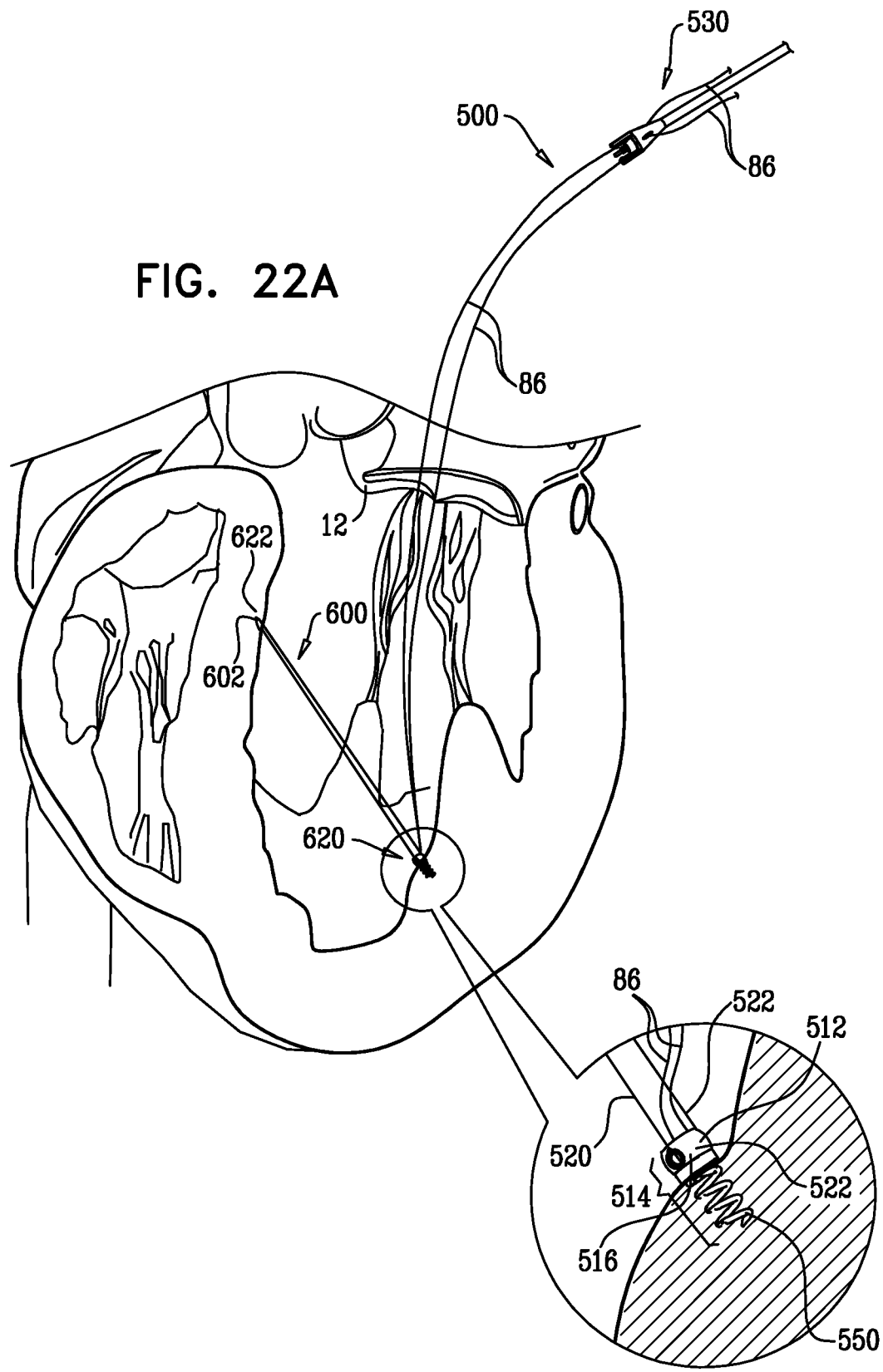
FIGS. 22A and 22B are schematic illustrations of another implant structure comprising repair chords, in accordance with respective applications of the present invention.
Figure 22B:
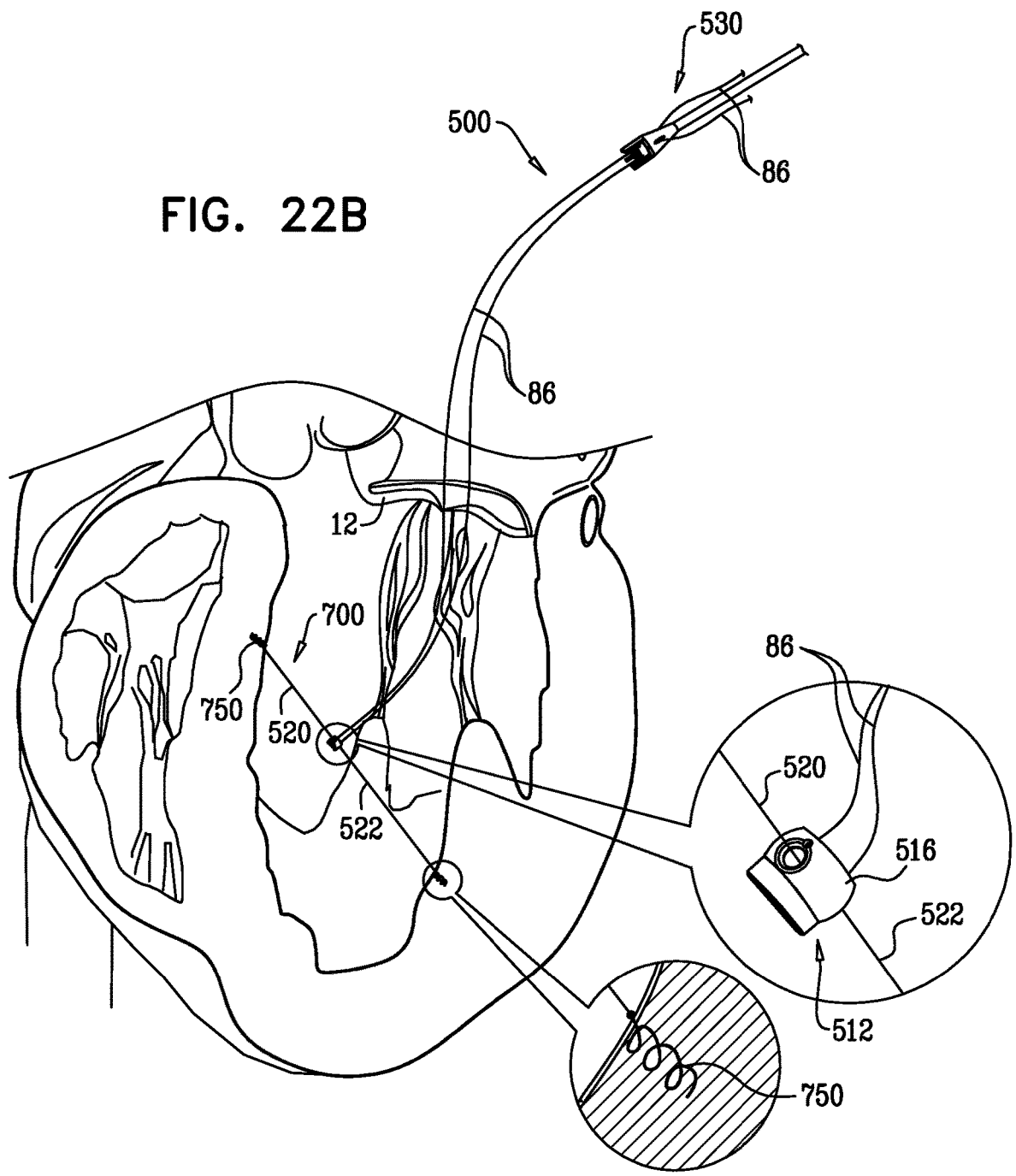

Reference is made to FIGS. 22A and 22B, which are schematic illustrations of another implant structure 600 comprising repair chords 510, in accordance with respective applications of the present invention. In these application, repair chords 510 are used to adjust a distance between two portions of the ventricular wall.

FIG. 22A shows implant structure 600 comprising contracting mechanism assembly 514 implanted at a first portion 620 of heart tissue which faces and surrounds the left ventricle of the heart. The free ends of longitudinal members 520 and 522 are coupled to a second portion 622 of heart tissue which faces and surrounds the left ventricle, e.g., at the septum, by way of illustration and not limitation. The free ends of longitudinal members 520 and 522 are coupled to the heart tissue using any suitable attachment means 602, e.g., sutures, knotting, or tissue anchors such as helical anchors.

Implant structure 600 comprises contracting mechanism assembly 514, described hereinabove with reference to FIG. 20. Implant structure 600 comprises one or more longitudinal members 86, which are coupled to contracting mechanism 512, such as to housing 516 or to the spool. Rotation tool 530 is configured to pass over longitudinal members 86, engage the spool of contracting mechanism 512, and rotate the spool, thereby tightening the contracting mechanism, and shortening and tensioning longitudinal members 520 and 522. In response to the shortening of longitudinal members 520 and 522, first and second portions 620 and 622 of the heart tissue are pulled toward one another. Consequently, the dimensions of the heart wall are restored to physiological dimensions, and the leaflets are drawn toward one another.

FIG. 22B shows implant structure 700 for adjusting a distance between two portions of a heart wall of the left ventricle of the patient. Longitudinal members 520 and 522 are coupled at first portions thereof to a rotatable structure, e.g., a spool, of contracting mechanism 512. Respective free ends of each member 520 and 522 are coupled to opposing first and second portions of the heart wall which faces and surrounds the ventricular lumen of the heart. The free end of longitudinal member 522 is coupled to first implantation site using a first helical anchor 750 by way of illustration and not limitation. For example, the free end of longitudinal member 522 is coupled to the first implantation site using sutures, knots, or any tissue anchor known in the art. The free end of longitudinal member 520 is coupled to a second implantation site using a second helical anchor 750 by way of illustration and not limitation. For example, the free end of longitudinal member 520 is coupled to the second implantation site using sutures, knots, or any tissue anchor known in the art. In such a configuration, contracting mechanism 512 is disposed between longitudinal members 520 and 522 and is not directly coupled to heart tissue.

Following the attaching of longitudinal members 520 and 522 to the first and second implantation sites, respectively, rotation tool 530 is passed over longitudinal members 86, and used to rotate the spool of contracting mechanism 512, such as described hereinabove. As described hereinabove, using tool 530, the spool of contracting mechanism 512 is rotated in order to adjust a distance between the first and second implantation sites. Responsively, the first and second portions of the ventricle wall are drawn together. Consequently, the dimensions of the heart wall are restored to physiological dimensions, and the leaflets are drawn toward one another.

For some applications, implant structure 500 utilizes techniques described hereinabove with reference to FIGS. 5A-B, 6A-B, 7, 8, 9A-C, and/or 10A-D. For some applications, implant structure 500 utilizes techniques described in U.S. patent application Ser. No. 12/548,991, filed Aug. 27, 2009, which is incorporated herein by reference, such as with reference to one or more of FIGS. 19-21 thereof.

Figure 23:
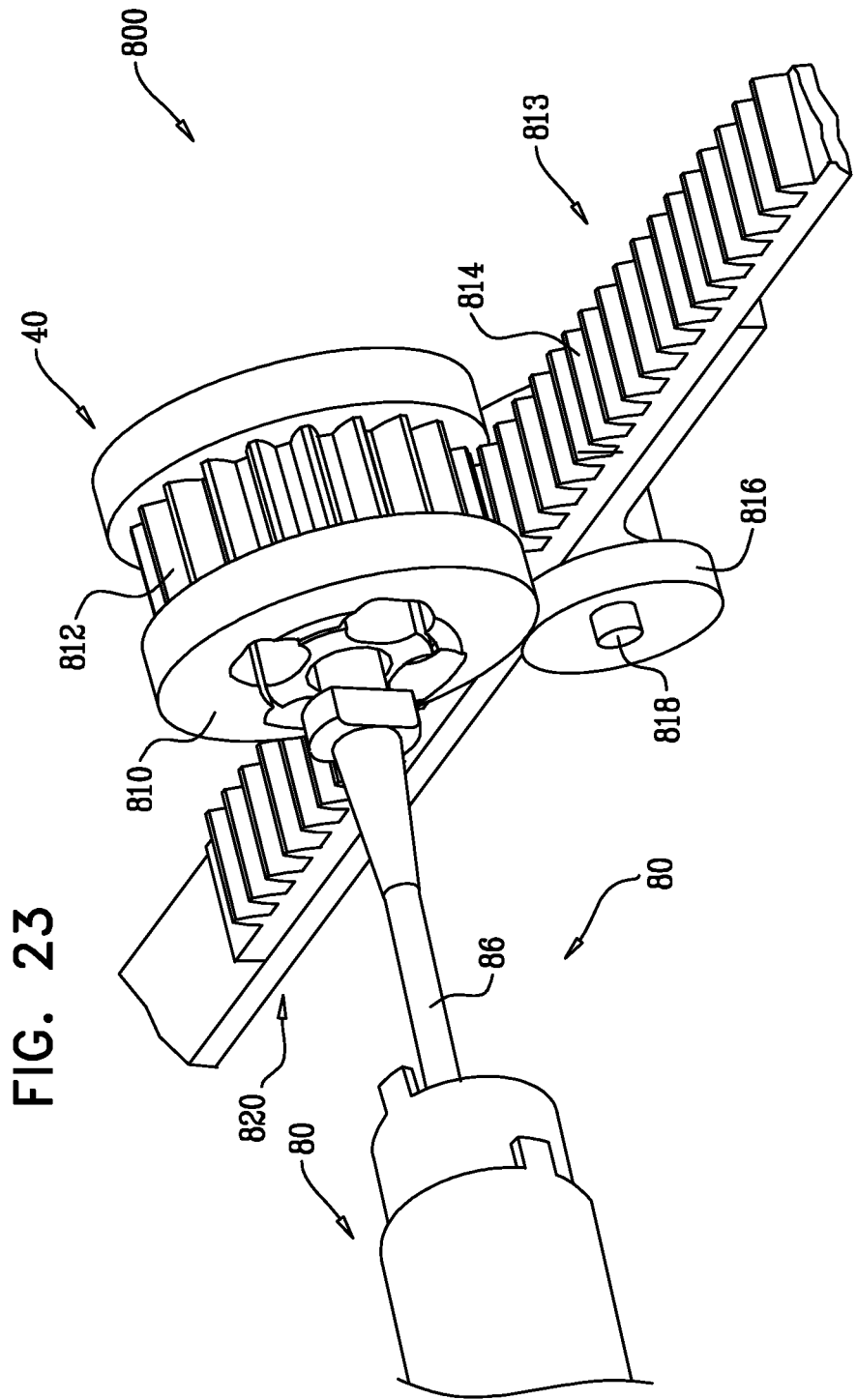
FIG. 23 is a schematic illustration of another configuration of a contracting mechanism and an implant structure, in accordance with an application of the present invention.

Reference is made to FIG. 23, which is a schematic illustration of another configuration of contracting mechanism 40 and an implant structure 800, in accordance with an application of the present invention. In this application, contracting mechanism 40 is used to adjust a length or circumference of implant structure 800, which may comprise, for example, a partial or a full annuloplasty ring, such as ring 22, or another implant structure. In this application, a first rotatable structure 810 is shaped so as to define a pinion 812, and a first portion 813 of implant structure 800 is shaped so as to define a rack 814. Geared teeth of pinion 812 matingly engage teeth of rack 814, such that first portion 813 passes between first rotatable structure 810 and a second rotatable structure 816 that rotates on an axel 818 that is coupled to a second portion 820 of implant structure 800. The first and second rotatable structures 810 and 816 are maintained at an appropriate distance from each other using a housing or bracket. (For clarity of illustration, the housing or bracket is not shown in the figure, because the housing or bracket is typically positioned on the further side of the rotatable structures that is not visible in the figure.) For example, the housing or bracket may connect the axels of the rotatable structures on the sides thereof opposite the sides shown in FIG. 23. Alternatively, for some applications, second rotatable structure 816 is not provided, and first rotatable structure 810 is coupled directly to second portion 820 of implant structure 800.

For applications in which implant structure 800 comprises a full band, such as a full annuloplasty ring, the first and second portions 813 and 820 of implant structure 800 are opposite ends of the same continuous structure. For applications in which implant structure comprises a partial band, such as a partial annuloplasty ring, the respective portions of first and second portions 813 and 820 are coupled near respective ends of a sleeve, or themselves define the ring.

Implant structure 800 comprises longitudinal member 86, which is coupled to contracting mechanism 40. Rotation tool 80 is provided for rotating first rotatable structure 810. The tool is configured to be guided over the longitudinal member, to engage the rotatable structure, and to rotate the rotatable structure in response to a rotational force applied to the tool, such as using techniques described hereinabove with reference to FIGS. 5A-B, 6A-B, 7, 8, 9A-C, and/or 10A-D.

Figure 24A:
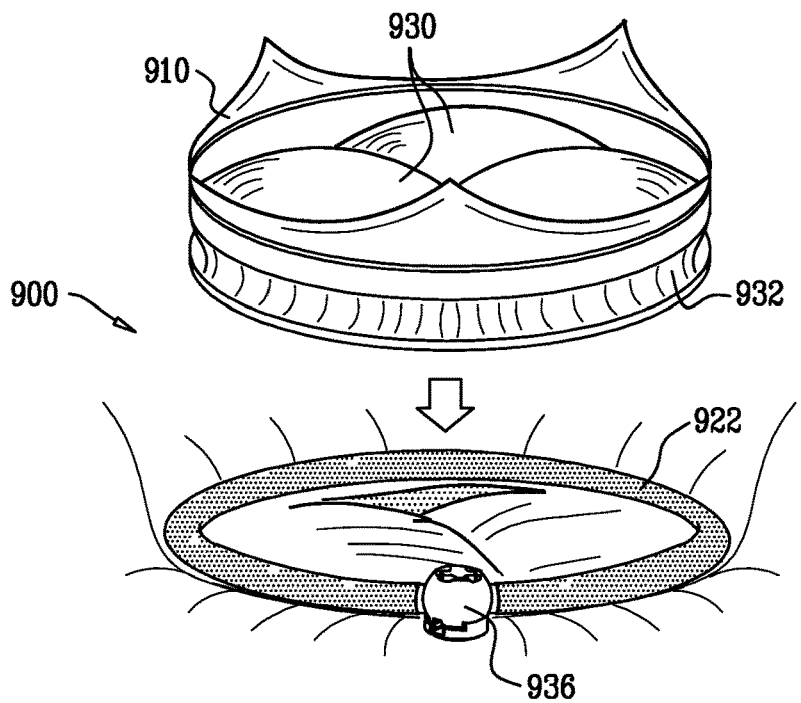
FIGS. 24A-B and 25 are schematic illustrations of a valve prosthesis assembly, in accordance with an application of the present invention.
Figure 24B:
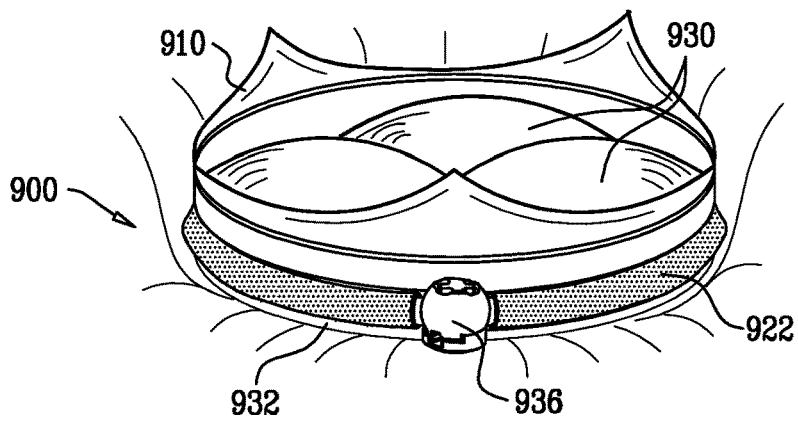
Figure 25:
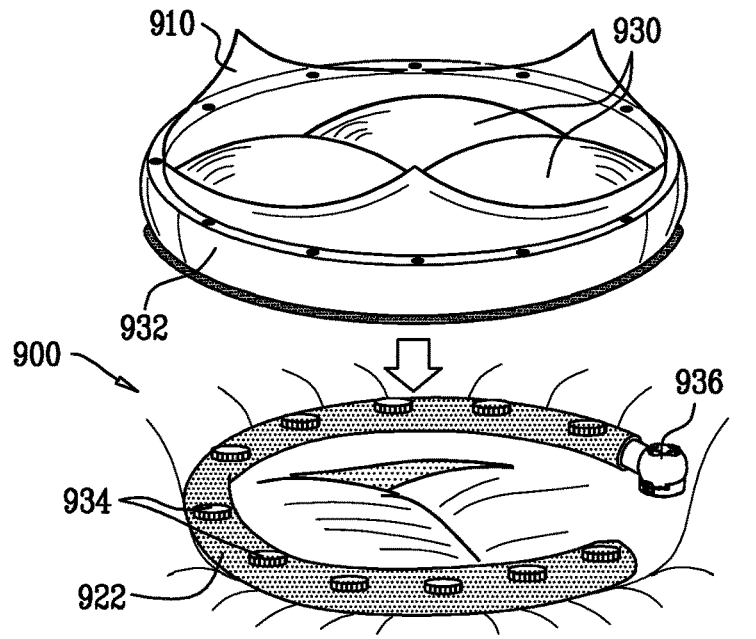

Reference is made to FIGS. 24A-B and 25, which are schematic illustrations of a valve prosthesis assembly 900, in accordance with an application of the present invention. Valve prosthesis assembly 900 comprises a prosthetic heart valve 910 that is couplable to a base ring 922. Prosthetic heart valve 910 is used to replace a native diseased heart valve. Valve 910 comprises a plurality of artificial leaflets 930, which comprise a pliant material. Valve 910 may implement techniques known in the artificial valve art, such as described, for example, in US Patent Application Publication 2007/0255400 to Parravicini et al., US Patent Application Publication 2004/0122514 to Fogarty et al., US Patent Application Publication 2007/0162111 to Fukamachi et al., and/or US Patent Application Publication 2008/0004697 to Lichtenstein et al., all of which are incorporated herein by reference.

Valve 910 further comprises an annular base 932, to which artificial leaflets 930 are coupled. Annular base 932 is configured to be couplable to base ring 922 during an implantation procedure. For example, as show in FIG. 25, base ring 922 may comprise one or more coupling elements 934, such as clips or magnets, which are configured to be coupled to corresponding coupling elements on a lower surface of annular base 932 (not visible in the figures). Alternatively or additionally, annular base 932 may be configured to be placed within the opening defined by base ring 922, as shown in FIG. 24A. To hold the annular base coupled to the base ring, the base ring is tightened around the annular base, as shown in FIG. 24B, typically using one or more of the techniques described hereinabove for contracting implant structures. Typically, valve prosthesis assembly 900, such as annular base 932 thereof, is configured to push and hold open the intact diseased native leaflets.

Base ring 922 implements one or more of the techniques of annuloplasty ring 22 described hereinabove. In particular, base ring 922 may be coupled to the annulus of the native diseased valve using the anchoring techniques described hereinabove. In addition, base ring 922 typically comprises a rotatable structure 936, such as a spool, which is typically implemented using techniques described herein. The rotatable structure is arranged such that rotation thereof contracts base ring 922, typically using techniques described herein. Such tightening may serve to couple base ring 922 to annular base 932, as shown in FIG. 24B. Alternatively or additionally, such tightening sets the desired dimensions of the base ring, in order to align the coupling elements of the base ring with those of valve 910, thereby enabling tight coupling, such as for the applications described with reference to FIG. 25.

For some applications, base ring 922 comprises a partial ring, as shown in FIG. 25, while for other applications, the base ring comprises a full ring, as shown in FIGS. 24A-B.

Valve prosthesis assembly 900 is typically implanted in a minimally invasive transcatheter or percutaneous procedure. The procedure begins with the introduction and implantation of base ring 922 into the heart, such as using techniques for implanting annuloplasty ring 22, described hereinabove with reference to FIGS. 11A-I. Prosthetic heart valve 910 is subsequently introduced into the heart and coupled to base ring 922, as described above. Valve prosthesis assembly 900 is typically used for replacement of a diseased native mitral valve, aortic valve, tricuspid valve, or pulmonary valve.

For some applications of the present invention, system 20 is used to treat an atrioventricular valve other than the mitral valve, i.e., the tricuspid valve. For these applications, annuloplasty ring 22 and other components of system 20 described hereinabove as being placed in the left atrium are instead placed in the right atrium. Although annuloplasty ring 22 is described hereinabove as being placed in an atrium, for some application the ring is instead placed in either the left or right ventricle.

For some applications, techniques described herein are practiced in combination with techniques described in one or more of the references cited in the Background section of the present patent application.

Additionally, the scope of the present invention includes applications described in the following applications, which are incorporated herein by reference. In an application, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007, which published as PCT Publication WO 08/068756;

U.S. patent application Ser. No. 11/950,930 to Gross et al., entitled, "Segmented ring placement," filed on Dec. 5, 2007, which published as US Patent Application Publication 2008/0262609;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008, which published as US Patent Application Publication 2010/0161047;

U.S. Provisional Patent Application 61/207,908 to Miller et al., entitled, "Actively-engageable movement-restriction mechanism for use with an annuloplasty structure," filed on Feb. 17, 2009;

U.S. patent application Ser. No. 12/435,291 to Maisano et al., entitled, "Adjustable repair chords and spool mechanism therefor," filed on May 4, 2009, which published as US Patent Application Publication 2010/0161041;

U.S. patent application Ser. No. 12/437,103 to Zipory et al., entitled, "Annuloplasty ring with intra-ring anchoring," filed on May 7, 2009, which published as US Patent Application Publication 2010/0286767;

PCT Patent Application PCT/IL2009/000593 to Gross et al., entitled, "Annuloplasty devices and methods of delivery therefor," filed on Jun. 15, 2009 which published as PCT Publication WO 10/004546;

U.S. patent application Ser. No. 12/548,991 to Maisano et al., entitled, "Implantation of repair chords in the heart," filed on Aug. 27, 2009, which published as US Patent Application Publication 2010/0161042;

U.S. patent application Ser. No. 12/608,316 to Miller et al., entitled, "Tissue anchor for annuloplasty ring," filed on Oct. 29, 2009, which published as US Patent Application Publication 2011/0106247;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabiri et al., entitled, "Adjustable annuloplasty devices and mechanisms therefor," filed on Dec. 22, 2009, which published as PCT Publication WO 10/073246;

U.S. patent application Ser. No. 12/689,635 to Zipory et al., entitled, "Over-wire rotation tool," filed on Jan. 19, 2010, which published as US Patent Application Publication 2010/0280604;

U.S. patent Ser. No. 12/689,693 to Hammer et al., entitled, "Deployment techniques for annuloplasty ring," filed on Jan. 19, 2010, which published as US Patent Application Publication 2010/0280605; and/or U.S. patent application Ser. No. 12/706,868 to Miller et al., entitled, "Actively-engageable movement-restriction mechanism for use with an annuloplasty structure," filed on Feb. 17, 2010, which published as US Patent Application Publication 2010/0211166.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus comprising:
an implant structure, which comprises a contracting mechanism, which comprises (a) a rotatable structure, arranged such that rotation of the rotatable structure contracts the implant structure, and (b) a locking mechanism;
a rotation tool, which is configured to engage the rotatable structure, and to rotate the rotatable structure in response to a rotational force applied to the rotation tool; and
a longitudinal guide member, which is (a) removably coupled to the contracting mechanism, (b) configured to guide the rotation tool to the rotatable structure, and (c) comprises a distal force applicator, wherein the rotation tool and the longitudinal guide member are arranged such that the rotation tool is axially moveable with respect to the longitudinal guide member, and wherein the contracting mechanism is arranged such that:
the locking mechanism is unlocked when the longitudinal guide member is coupled to the contracting mechanism in a first state, thereby allowing the rotatable structure to rotate,
the locking mechanism is locked when the longitudinal guide member is coupled to the contracting mechanism in a second state, thereby restricting the rotation of the rotatable structure, and
the locking mechanism is locked when the longitudinal guide member is not coupled to the contracting mechanism, thereby restricting the rotation of the rotatable structure.

2. The apparatus according to claim 1, wherein the contracting mechanism is arranged such that:
when in the first state, the longitudinal guide member is coupled to the contracting mechanism at a first level of distal advancement with respect to the contracting mechanism, thereby allowing the rotatable structure to rotate, and
when in the second state, the longitudinal guide member is coupled to the contracting mechanism at a second level of distal advancement with respect to the contracting mechanism, thereby restricting the rotation of the rotatable structure, the second level of distal advancement being less than the first level of distal advancement.

3. The apparatus according to claim 2, wherein the rotation tool comprises one or more tubes that are configured to pass over the longitudinal guide member, such that the longitudinal guide member is radially within the one or more tubes.

4. The apparatus according to claim 2, wherein an upper surface of the rotatable structure is shaped so as to define a threaded opening, and wherein a distal portion of the longitudinal guide member is shaped so as to define a screw thread that is removably screwed into the threaded opening.

5. The apparatus according to claim 4, wherein, when the longitudinal guide member is coupled to the contracting mechanism at the second level of distal advancement, the distal portion of the longitudinal guide member is in a state of being partially unscrewed from the threaded opening.

6. The apparatus according to claim 4, wherein the distal force applicator extends distally beyond the screw thread, and is configured to unlock the locking mechanism when the longitudinal guide member is coupled to the contracting mechanism at the first level of distal advancement.

7. The apparatus according to claim 2,
wherein the locking mechanism is shaped to provide a protrusion and a depressible portion,
wherein a lower surface of the rotatable structure is shaped to define one or more recesses, and
wherein the contracting mechanism is arranged such that:
when the longitudinal guide member is coupled to the contracting mechanism at the second level of distal advancement or the longitudinal guide member is not coupled to the contracting mechanism, the protrusion is positioned with one of the recesses, thereby locking the locking mechanism, and
when the longitudinal guide member is coupled to the contracting mechanism at the first level of distal advancement, the force applicator pushes against the depressible portion, thereby freeing the protrusion from the recess and unlocking the locking mechanism.

8. The apparatus according to claim 2, wherein the rotatable structure comprises a spool.

9. The apparatus according to claim 8,
wherein the locking mechanism is shaped to provide a protrusion and a depressible portion,
wherein a lower surface of the spool is shaped to define one or more recesses, and
wherein the contracting mechanism is arranged such that:
when the longitudinal guide member is coupled to the contracting mechanism at the second level of distal advancement or the longitudinal guide member is not coupled to the contracting mechanism, the protrusion is positioned with one of the recesses, thereby locking the locking mechanism, and
when the longitudinal guide member is coupled to the contracting mechanism at the first level of distal advancement, the force applicator pushes against the depressible portion, thereby freeing the protrusion from the recess and unlocking the locking mechanism.

10. The apparatus according to claim 2, wherein the longitudinal guide member has a diameter of between 0.1 and 1 mm.

11. The apparatus according to claim 2, wherein the contracting mechanism comprises a housing that houses the rotatable structure, and wherein the contracting mechanism is arranged such that when unlocked, the locking mechanism allows the rotatable structure to rotate with respect to the housing.

12. The apparatus according to claim 2, wherein the implant structure further comprises a flexible elongated contracting member separate and distinct from the longitudinal guide member, and wherein the contracting mechanism is configured to contract the implant structure by pulling on the contracting member.

13. The apparatus according to claim 12,
wherein the rotatable structure comprises a spool,
wherein the contracting member has a first portion wound around the spool, and a second portion that extends at least along a portion of the implant structure,
wherein the spool is arranged such that the rotation of the spool contracts the implant structure by winding the contracting member around the spool, and
wherein the rotation tool is configured to increase a number of times the contracting member is wound around the spool by rotating the rotatable structure in response to the rotational force applied to the rotation tool.

14. The apparatus according to claim 1, wherein an upper surface of the rotatable structure is shaped so as to define a threaded opening, and wherein a distal portion of the longitudinal guide member is shaped so as to define a screw thread that is removably screwed into the threaded opening.

15. The apparatus according to claim 1,
wherein the locking mechanism is shaped to provide a protrusion and a depressible portion,
wherein a lower surface of the rotatable structure is shaped to define one or more recesses, and
wherein the contracting mechanism is arranged such that:
when the longitudinal guide member is coupled to the contracting mechanism in the second state or the longitudinal guide member is not coupled to the contracting mechanism, the protrusion is positioned with one of the recesses, thereby locking the locking mechanism, and when the longitudinal guide member is coupled to the contracting mechanism in the first state, the force applicator pushes against the depressible portion, thereby freeing the protrusion from the recess and unlocking the locking mechanism.

16. The apparatus according to claim 1, wherein the implant structure comprises a sleeve.

17. The apparatus according to claim 1, wherein the implant structure comprises a plurality of tissue anchors.

18. An apparatus comprising:
an implant structure, which comprises (a) a flexible elongated contracting member and (b) a contracting mechanism, which (i) is configured to contract the implant structure by pulling on the contracting member, and (ii) comprises a locking mechanism;
a rotation tool, which is configured to engage the contracting mechanism, and to actuate the contracting mechanism to pull on the contracting member; and
a longitudinal guide member, which (a) is separate and distinct from the flexible elongated contracting member (b) is removably coupled to the contracting mechanism, (c) is configured to guide the rotation tool to the contracting mechanism, and (d) comprises a distal force applicator,
wherein the rotation tool and the longitudinal guide member are arranged such that the rotation tool is axially moveable with respect to the longitudinal guide member, and
wherein the contracting mechanism is arranged such that:
the locking mechanism is unlocked when the longitudinal guide member is coupled to the contracting mechanism in a first state, thereby allowing actuation of the contracting mechanism,
the locking mechanism is locked when the longitudinal guide member is coupled to the contracting mechanism in a second state, thereby locking the contracting mechanism, and
the locking mechanism is locked when the longitudinal guide member is not coupled to the contracting mechanism, thereby locking the contracting mechanism.

19. The apparatus according to claim 18, wherein the contracting mechanism is arranged such that:
when in the first state, the longitudinal guide member is coupled to the contracting mechanism at a first level of distal advancement with respect to the contracting mechanism, thereby allowing actuation of the contracting mechanism, and
when in the second state, the longitudinal guide member is coupled to the contracting mechanism at a second level of distal advancement with respect to the contracting mechanism, thereby locking the contracting mechanism, the second level of distal advancement being less than the first level of distal advancement.

20. The apparatus according to claim 19, wherein the rotation tool comprises one or more tubes that are configured to pass over the longitudinal guide member, such that the longitudinal guide member is radially within the one or more tubes.

21. The apparatus according to claim 19, wherein an upper surface of the contracting mechanism is shaped so as to define a threaded opening, and wherein a distal portion of the longitudinal guide member is shaped so as to define a screw thread that is removably screwed into the threaded opening.

22. The apparatus according to claim 21, wherein, when the longitudinal guide member is coupled to the contracting mechanism at the second level of distal advancement, the distal portion of the longitudinal guide member is in a state of being partially unscrewed from the threaded opening.

23. The apparatus according to claim 21, wherein the distal force applicator extends distally beyond the screw thread, and is configured to unlock the locking mechanism when the longitudinal guide member is coupled to the contracting mechanism at the first level of distal advancement.

24. The apparatus according to claim 19, wherein the contracting mechanism comprises a housing.

25. The apparatus according to claim 19,
wherein the contracting mechanism comprises a rotatable structure, arranged such that rotation of the rotatable structure contracts the implant structure by pulling on the contracting member, and
wherein the rotation tool is configured to engage the rotatable structure, and to rotate the rotatable structure in response to a rotational force applied to the rotation tool.

26. The apparatus according to claim 25, wherein the contracting mechanism comprises a housing that houses the rotatable structure.

27. The apparatus according to claim 26, wherein the contracting mechanism is arranged such that when unlocked, the locking mechanism allows the rotatable structure to rotate with respect to the housing.

28. The apparatus according to claim 25, wherein the rotatable structure comprises a spool.

29. The apparatus according to claim 28,
wherein the contracting member has a first portion wound around the spool, and a second portion that extends at least along a portion of the implant structure,
wherein the spool is arranged such that the rotation of the spool contracts the implant structure by winding the contracting member around the spool, and
wherein the rotation tool is configured to increase a number of times the contracting member is wound around the spool by rotating the rotatable structure in response to the rotational force applied to the rotation tool.

30. The apparatus according to claim 19, wherein the longitudinal guide member has a diameter of between 0.1 and 1 mm.

31. The apparatus according to claim 18, wherein an upper surface of the contracting mechanism is shaped so as to define a threaded opening, and wherein a distal portion of the longitudinal guide member is shaped so as to define a screw thread that is removably screwed into the threaded opening.

32. The apparatus according to claim 18, wherein the implant structure comprises a sleeve.

33. The apparatus according to claim 18, wherein the implant structure comprises a plurality of tissue anchors.

34. An apparatus comprising:
an implant structure, which comprises (a) a flexible elongated contracting member configured to contract the implant structure when the contracting member is tightened, and (b) a locking mechanism configured to restrict tightening of the contracting member;
a rotation tool, which is configured to engage the implant structure and to tighten the contracting member; and a longitudinal guide member, which (a) is separate and distinct from the flexible elongated contracting member, (b) is removably coupled to the implant structure, (c) is configured to guide the rotation tool to the implant structure, and (d) comprises a distal force applicator, wherein the rotation tool and the longitudinal guide member are arranged such that the rotation tool is axially moveable with respect to the longitudinal guide member, and wherein the locking mechanism is arranged such that:
- the locking mechanism is unlocked when the longitudinal guide member is coupled to the implant structure in a first state, thereby allowing the tightening of the contracting member,
- the locking mechanism is locked when the longitudinal guide member is coupled to the implant structure in a second state, thereby restricting the tightening of the contracting member, and
- the locking mechanism is locked when the longitudinal guide member is not coupled to the implant structure, thereby restricting the tightening of the contracting member.

35. The apparatus according to claim 34, wherein the contracting mechanism is arranged such that:
- when in the first state, the longitudinal guide member is coupled to the implant structure at a first level of distal advancement with respect to the locking mechanism, thereby allowing tightening of the contracting member, and
- when in the second state, the longitudinal guide member is coupled to the implant structure at a second level of distal advancement with respect to the locking mechanism, thereby restricting the tightening of the contracting member, the second level of distal advancement being less than the first level of distal advancement.

36. The apparatus according to claim 35, wherein the locking mechanism is configured to reversibly restrict the tightening of the contracting member.

* * * * *